(12) United States Patent
Siu et al.

(10) Patent No.: US 12,201,985 B2
(45) Date of Patent: *Jan. 21, 2025

(54) SYSTEM AND METHOD FOR STORAGE

(71) Applicant: ILLUMINA, INC., San Diego, CA (US)

(72) Inventors: Merek Siu, Alameda, CA (US); Ali Agah, Menlo Park, CA (US); Stanley Hong, Palo Alto, CA (US); Tarun Khurana, Fremont, CA (US); Aathavan Karunakaran, Berkeley, CA (US); Craig Ciesla, Mountain View, CA (US); Amirali Kia, San Mateo, CA (US)

(73) Assignee: Illumina, Inc., San Diego, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/103,625

(22) Filed: Jan. 31, 2023

(65) Prior Publication Data

US 2023/0285974 A1 Sep. 14, 2023

Related U.S. Application Data

(63) Continuation of application No. 17/254,462, filed as application No. PCT/US2020/034517 on May 26, 2020, now Pat. No. 11,590,505.

(Continued)

(51) Int. Cl.
*B01L 3/00* (2006.01)
*C12Q 1/6869* (2018.01)
(Continued)

(52) U.S. Cl.
CPC .......... *B01L 3/50855* (2013.01); *G11C 13/02* (2013.01); *G16B 50/30* (2019.02);
(Continued)

(58) Field of Classification Search
CPC ......... B01L 3/50855; B01L 2300/0645; B01L 2300/0829; G16B 50/30; G16B 30/10; G11C 13/02; G11C 13/04; C12Q 1/6869
See application file for complete search history.

(56) References Cited

U.S. PATENT DOCUMENTS

| | | |
|---|---|---|
| 5,787,032 A | 7/1998 | Heller et al. |
| 7,414,116 B2 | 8/2008 | Milton et al. |

(Continued)

FOREIGN PATENT DOCUMENTS

| | | |
|---|---|---|
| EP | 2714935 B1 | 3/2017 |
| WO | WO 2014/150522 A1 | 9/2014 |
| WO | WO 2018/094115 A1 | 5/2018 |

OTHER PUBLICATIONS

International Search Report and Written Opinion dated Jul. 14, 2020, for International Application No. PCT/US2020/034517, 6 pages.

*Primary Examiner* — Jill A Warden
(74) *Attorney, Agent, or Firm* — Frost Brown Todd LLP

(57) ABSTRACT

Devices, systems, and methods for non-volatile storage include a well activation device operable to modify one or more wells from a plurality of wells of a flow cell to provide a set of readable wells. Readable wells are configured to allow exposure of a well to substances from nucleotide sequencing fluids, and prevent exposure to other substances and fluids, such as nucleotide synthesizing fluids. The well activation device may also modify wells to provide a set of writeable wells. This set of wells is configured to allow exposure to the nucleotide synthesizing fluids and substances; and prevent exposure to the nucleotide sequencing fluids and substances. There may also be provisions made for risk mitigation for data errors such as generating commands to write specified data to a nucleotide sequence associated with a particular location in a storage device, (Continued)

reading the nucleotide sequence and performing a comparison.

12 Claims, 16 Drawing Sheets

Related U.S. Application Data

(60) Provisional application No. 62/855,610, filed on May 31, 2019, provisional application No. 62/855,682, filed on May 31, 2019.

(51) Int. Cl.
    *G11C 13/02*     (2006.01)
    *G11C 13/04*     (2006.01)
    *G16B 50/30*     (2019.01)
    *G16B 30/10*     (2019.01)

(52) U.S. Cl.
    CPC ............... *B01L 2300/0645* (2013.01); *B01L 2300/0829* (2013.01); *C12Q 1/6869* (2013.01); *G11C 13/04* (2013.01); *G16B 30/10* (2019.02)

(56) References Cited

U.S. PATENT DOCUMENTS

| | | |
|---|---|---|
| 8,906,320 B1 | 12/2014 | Eltoukhy et al. |
| 9,012,022 B2 | 4/2015 | George et al. |
| 9,453,258 B2 | 9/2016 | Kain et al. |
| 9,512,422 B2 | 12/2016 | Barnard et al. |
| 10,254,225 B2 | 4/2019 | Zhong et al. |
| 11,590,505 B2 | 2/2023 | Siu et al. |
| 2014/0274747 A1 | 9/2014 | Kain et al. |
| 2015/0261664 A1 | 9/2015 | Goldman et al. |
| 2016/0110499 A1 | 4/2016 | Donnet |
| 2016/0273032 A1 | 9/2016 | Esfandyarpour et al. |
| 2016/0356715 A1 | 12/2016 | Zhong et al. |
| 2018/0117587 A1 | 5/2018 | Lemoine et al. |
| 2018/0327829 A1 | 11/2018 | Mir |
| 2019/0136307 A1* | 5/2019 | Predki ............... C12Q 1/6869 |
| 2019/0362814 A1* | 11/2019 | Roquet ............. G11C 13/0019 |
| 2019/0383788 A1* | 12/2019 | Predki ............... C12Q 1/6869 |

* cited by examiner

SYSTEM AND METHOD FOR STORAGE

RELATED APPLICATIONS

This application is a continuation of U.S. patent application Ser. No. 17/254,462, entitled "System and Method for Storage," filed on Dec. 21, 2020, issued as U.S. Pat. No. 11,590,505 on Feb. 28, 2023, which is a national stage entry of International Patent Application No. PCT/US2020/034517, entitled "System and Method for Storage," filed on May 26, 2020, which claims priority to U.S. Provisional Patent App. No. 62/855,610, entitled "System and Method for Non-Volatile Polynucleotide Storage," filed on May 31, 2019, which is incorporated by reference herein in its entirety. International Patent Application No. PCT/US2020/034517 also claims priority to U.S. Provisional Patent App. No. 62/855,682, entitled "DNA Storage Device with In-Situ Quality Control," filed on May 31, 2019, which is incorporated by reference herein in its entirety.

BACKGROUND

Computer systems have used various different mechanisms to store data, including magnetic storage, optical storage, and solid-state storage. Such forms of data storage may present drawbacks in the form of read-write speed, duration of data retention, power usage, or data density.

Just as naturally occurring DNA may be read, machine-written DNA may also be read. Pre-existing DNA reading techniques may include an array-based, cyclic sequencing assay (e.g., sequencing-by-synthesis (SBS)), where a dense array of DNA features (e.g., template nucleic acids) are sequenced through iterative cycles of enzymatic manipulation. After each cycle, an image may be captured and subsequently analyzed with other images to determine a sequence of the machine-written DNA features. In another biochemical assay, an unknown analyte having an identifiable label (e.g., fluorescent label) may be exposed to an array of known probes that have predetermined addresses within the array. Observing chemical reactions that occur between the probes and the unknown analyte may help identify or reveal properties of the analyte.

SUMMARY

Described herein are devices, systems, and methods for polynucleotide storage of data including features for per-well activation, simultaneous read-write caching, and multi-volume management for simultaneous read-write capabilities, as well as for mitigating the risk of errors in such storage, such as by including quality control measures in the processes used for reading and writing data encoded in polynucleotides.

An implementation relates to a system for non-volatile storage comprising: a storage controller comprising a processor and a memory; a storage device comprising: a flow cell comprising a plurality of wells with open sides accessible from a first surface of the flow cell, wherein the wells are adapted to contain polynucleotides, a fluidics interface, and a sequencing interface; a fluidics device to provide one or more fluids to the first surface of the flow cell, wherein the one or more fluids comprise a nucleotide writing reagent and a nucleotide reading reagent; a sequencing device to sequence polynucleotides within the plurality of wells via the sequencing interface and determine nucleotides; and a well activation device to: modify one or more wells from the plurality of wells to provide a set of readable wells, wherein the set of readable wells allow exposure to the nucleotide reading reagent and prevent exposure to other reagents from the fluidics device, and modify one or more wells from the plurality of wells to provide a set of writeable wells, wherein the set of writeable wells allow exposure to the nucleotide writing reagent and prevent exposure to other reagents from the fluidics device.

Variations on any one or more of the above implementations exist, wherein the well activation device comprises a plurality of electrodes, and wherein: at least one electrode of the plurality of electrodes is positioned proximately to each well of the plurality of wells, a control interface of the storage device is coupled with the plurality of electrodes and provides a set of control signals from the storage controller to the plurality of electrodes, each of the plurality of electrodes produce a voltage based upon the set of control signals, the voltage comprising a first voltage or a second voltage, and the first voltage produced by an electrode of the plurality of electrodes modifies a well of the plurality of wells proximate to the electrode producing the first voltage as a readable well and the second voltage produced by an electrode of the plurality of electrodes modifies a well of the plurality of wells proximate to the electrode producing the second voltage as a writeable well.

Variations on any one or more of the above implementations exist, wherein the at least one electrode is positioned on a sidewall of each well of the plurality of wells.

Variations on any one or more of the above implementations exist, wherein the at least one electrode is positioned on the first surface at a perimeter of each well of the plurality of wells.

Variations on any one or more of the above implementations exist, wherein the at least one electrode is positioned at the bottom of each well of the plurality of wells, and wherein the at least one electrode comprises a ring shape that allows light to pass from a second surface of the flow cell, opposite the first surface, through the ring shape and into the well of the plurality of wells in which the at least one electrode is positioned.

Variations on any one or more of the above implementations exist, wherein the second voltage causes hybridization of an inhibitor of an enzyme for the well of the plurality of wells proximate to the electrode producing the second voltage and binds a desired nucleotide to the well of the plurality of wells proximate to the electrode producing the second voltage.

Variations on any one or more of the above implementations exist, wherein: the well activation device comprises a plurality of pH control devices, each pH control device corresponding to a well of the plurality of wells, and each of the pH control devices produce a voltage that controls pH of a voltage sensitive functionalized fluid provided by the fluidics device to modify the well of the plurality of wells corresponding to the pH control device as either a readable well or a writeable well.

Variations on any one or more of the above implementations exist, wherein: the well activations device comprises a spatial light modulator (SLM) to emit light into one or more wells of the plurality of wells, and the emitted light modifies each of the one or more wells as either a readable well or a writeable well.

Variations on any one or more of the above implementations exist, wherein the storage controller, during a sequencing operation: receive a set of address data that describes nucleotides of polynucleotides in an address well of the plurality of wells, from the sequencing device, determine a set of target wells from the plurality of wells based on the set of address data, and cause the fluidic device to provide the nucleotide reading reagent only to the set of target wells.

Variations on any one or more of the above implementations exist, wherein the storage controller, during the sequencing operation, controls localization of enzymes of the nucleotide reading reagent by causing the fluidic device to strip enzymes from the plurality of wells, and causing the well activation device to provide charged tags.

Variations on any one or more of the above implementations exist, wherein the well activation device comprises: an electrical release mechanism to produce a voltage to modify a well as a writeable well, and a photonic release mechanism to produce photonic energy to modify a well as a writeable well, and wherein the set of writeable wells comprises wells modified by the electrical release mechanism and wells modified by the photonic release mechanism.

Variations on any one or more of the above implementations exist, wherein: the well activation device comprises an electro-wetting device proximate to the first surface of the flow cell, the electro-wetting device to deliver fluid from the fluidic device to any well of the plurality of wells, and the storage controller, during a simultaneous sequencing and synthesis operation: provides a droplet of the nucleotide reading reagent to a first well of the plurality of wells, provides a droplet of the nucleotide writing reagent to a second well of the plurality of wells, wherein the first well and the second well are adjacent.

Variations on any one or more of the above implementations exist, wherein each of the plurality of wells comprises: a polarization feature to reduce cross-talk between nearby wells, and an optical waveguide feature to reduce cross talk between nearby wells.

Variations on any one or more of the above implementations exist, wherein the storage controller is to, during a synthesis operation: convert a set of data into a set of nucleotides, synthesize a first polynucleotide strand in a first well of the set of writeable wells based on the set of nucleotides, and synthesize a second polynucleotide strand in a second well of the set of writeable wells based on the set of nucleotides, wherein the first polynucleotide strand and the second polynucleotide strand are identical when correctly synthesized.

Variations on any one or more of the above implementations exist, wherein the storage controller sequences the first polynucleotide strand and the second polynucleotide strand with the sequencing device and, where they are not identical, provides an indication of a synthesis error.

Variations on any one or more of the above implementations exist, further comprising a spatial light modulator to project optical patterns onto the flow cell via the sequencing interface, wherein the storage controller operates the spatial light modulator to project an identical optical pattern into the first well and the second well to synthesize the first polynucleotide strand and the second polynucleotide strand.

Variations on any one or more of the above implementations exist, wherein the storage controller is to, during a synthesis operation: convert a set of data into a set of nucleotides, synthesize a first polynucleotide strand in a first well of the set of writeable wells based on a first portion of the set of nucleotides, and in parallel with synthesis of the first polynucleotide strand, synthesize a second polynucleotide strand in a second well of the set of writeable wells based on a second portion of the set of nucleotides, wherein the first polynucleotide strand and the second polynucleotide strand collectively represent the entirety of the set of nucleotides.

Variations on any one or more of the above implementations exist, wherein the storage controller is to, during a synthesis operation: convert a set of data into a set of nucleotides, synthesize a first polynucleotide strand in a first well of the set of writeable wells based on the set of nucleotides, synthesize a second polynucleotide strand in the first well based on the set of nucleotides, wherein the first polynucleotide strand and the second polynucleotide strand are identical when correctly synthesized, and produce a strand hash value based on the set of nucleotides, and synthesize the first polynucleotide strand and the second polynucleotide strand to add the strand hash value.

Variations on any one or more of the above implementations exist, wherein the storage controller is to, during a sequencing operation: sequence the first polynucleotide strand and the second polynucleotide strand in the first well with the sequencing device to determine a sequenced set of nucleotides and a sequenced hash value for each, where the sequenced set of nucleotides for the first polynucleotide strand and the second polynucleotide strand are not identical, provide an indication of a synthesis error, and, where the sequenced hash value for either the first polynucleotide strand or the second polynucleotide strand does not match a subsequent hash value of the sequenced set of nucleotides, provide an indication of a hash value mismatch.

Another implementation relates to a method for non-volatile polynucleotide storage comprising: mounting a storage device, the storage device comprising: a flow cell comprising a plurality of wells with open sides accessible from a first surface of the flow cell, wherein the wells are adapted to contain polynucleotides, a fluidics interface, and a sequencing interface; performing a synthesis operation to produce polynucleotides in the plurality of wells by operating a fluidics device to provide a nucleotide writing reagent to the first surface; performing a sequencing operation with a sequencing device and a nucleotide reading reagent from the fluidics device to determine nucleotides of polynucleotides in the plurality of wells; and using a well activation device prior to the synthesis operation and the sequencing operation to: modify one or more wells from the plurality of wells to provide a set of readable wells, wherein the set of readable wells allow exposure to the nucleotide reading reagent and prevent exposure to other reagent fluids from the fluidics device, and modify one or more wells from the plurality of wells to provide a set of writeable wells, wherein the set of writeable wells allow exposure to the nucleotide writing reagent and prevent exposure to other reagent fluids from the fluidics device.

Variations on any one or more of the above implementations exist, wherein using the well activation device comprises operating a plurality of electrodes of the well activation device, and wherein: at least one electrode of the plurality of electrodes is positioned proximately to each well of the plurality of wells, a control interface of the storage device is coupled with the plurality of electrodes and provides a set of control signals to the plurality of electrodes, each of the plurality of electrodes produce a voltage based upon the set of control signals, the voltage comprising a first voltage or a second voltage, and the first voltage modifies a well of the plurality of wells proximate to the electrode producing the first voltage as a readable well and the second voltage produced by an electrode of the plurality of electrodes modifies a well of the plurality of wells proximate to the electrode producing the second voltage as a writeable well.

Variations on any one or more of the above implementations exist, wherein operating the plurality of electrodes comprises operating at least one electrode positioned on a sidewall of a well of the plurality of wells.

Variations on any one or more of the above implementations exist, wherein operating the plurality of electrodes comprises operating at least one electrode positioned on the first surface at a perimeter of a well of the plurality of wells.

Variations on any one or more of the above implementations exist, wherein operating the plurality of electrodes comprises operating at least one electrode positioned at the bottom of a well of the plurality of wells, and wherein the at least one electrode comprises a ring shape that allows light to pass from a second surface of the flow cell, opposite the first surface, through the ring shape and into the well of the plurality of wells in which the at least one electrode is positioned.

Variations on any one or more of the above implementations exist, further comprising configuring the second voltage to cause hybridization of an inhibitor of an enzyme for the well of the plurality of wells proximate to the electrode producing the second voltage and bind a desired nucleotide to the well of the plurality of wells proximate to the electrode producing the second voltage.

Variations on any one or more of the above implementations exist, wherein using the well activation device comprises operating a plurality of pH control devices of the well activation device, and wherein: each pH control device corresponds to a well of the plurality of wells, and each of the pH control devices produce a voltage that controls pH of a voltage sensitive functionalized fluid provided by the fluidics device to modify the well of the plurality of wells corresponding to the pH control device as either a readable well or a writeable well.

The method of any one or more of the above implementations, wherein operating the well activation device comprises operating a spatial light modulator (SLM) to emit light into one or more wells of the plurality of wells, and wherein the emitted light modifies each of the one or more wells as either a readable well or a writeable well.

Variations on any one or more of the above implementations exist, further comprising, during the sequencing operation: receiving a set of address data from the sequencing device that describes nucleotides of sequenced polynucleotides from an address well of the plurality of wells, determining a set of target wells from the plurality of wells based on the set of address data, and causing the fluidic device to provide the nucleotide reading reagent only to the set of target wells.

Variations on any one or more of the above implementations exist, further comprising controlling localization of enzymes of the nucleotide reading reagent by causing the fluidic device to strip unneeded enzymes from the plurality of wells, and causing the well activation device to provide charged tags.

Variations on any one or more of the above implementations exist, wherein using the well activation device comprises: using an electrical release mechanism of the well activation device to produce a voltage to modify a well as a writeable well, and using a photonic release mechanism of the well activation device to produce photonic energy to modify a well as a writeable well, and wherein the set of writeable wells comprises wells modified by the electrical release mechanism and wells modified by the photonic release mechanism.

Variations on any one or more of the above implementations exist, wherein operating the well activation device comprises: operating an electro-wetting device of the well activation device to deliver fluid from the fluidic device to the plurality of wells, and during a simultaneous sequencing and synthesis operation: providing a droplet of the nucleotide reading reagent to a first well of the plurality of wells, and providing a droplet of the nucleotide writing reagent to a second well of the plurality of wells, wherein the first well and the second well are adjacent.

Variations on any one or more of the above implementations exist, further comprising, during the synthesis operation: converting a set of data into a set of nucleotides, synthesizing a first polynucleotide strand in a first well of the set of writeable wells based on the set of nucleotides, and synthesizing a second polynucleotide strand in a second well of the set of writeable wells based on the set of nucleotides, wherein the first polynucleotide strand and the second polynucleotide strand are identical when correctly synthesized.

Variations on any one or more of the above implementations exist, further comprising sequencing the first polynucleotide strand and the second polynucleotide strand with the sequencing device and, where they are not identical, providing an indication of a synthesis error.

Variations on any one or more of the above implementations exist, further comprising operating a spatial light modulator to project an identical optical pattern onto the first well and the second well via the sequencing interface, wherein the identical optical pattern is to synthesize the first polynucleotide strand and the second polynucleotide strand in parallel.

Variations on any one or more of the above implementations exist, further comprising, during the synthesis operation: converting a set of data into a set of nucleotides, synthesizing a first polynucleotide strand in a first well of the set of writeable wells based on a first portion of the set of nucleotides, and in parallel with synthesizing the first polynucleotide strand, synthesizing a second polynucleotide strand in a second well of the set of writeable wells based on a second portion of the set of nucleotides, wherein the first polynucleotide strand and the second polynucleotide strand collectively represent the entirety of the set of nucleotides.

Variations on any one or more of the above implementations exist, further comprising, during the synthesis operation: converting a set of data into a set of nucleotides, synthesizing a first polynucleotide strand in a first well of the set of writeable wells based on the set of nucleotides, synthesizing a second polynucleotide strand in the first well based on the set of nucleotides, wherein the first polynucleotide strand and the second polynucleotide strand are identical when correctly synthesized, and producing a strand hash value based on the set of nucleotides and synthesizing the first polynucleotide strand and the second polynucleotide strand to add the strand hash value.

Variations on any one or more of the above implementations exist, further comprising, during the sequencing operation: sequencing the first polynucleotide strand and the second polynucleotide strand in the first well with the sequencing device to determine a sequenced set of nucleotides and a sequenced hash value for each, where the sequenced set of nucleotides for the first polynucleotide strand and the second polynucleotide strand are not identical, providing an indication of a synthesis error, determine a subsequent hash value for each of the first polynucleotide strand and the second polynucleotide strand based on the sequenced set of nucleotides, and where the sequenced hash value for either the first polynucleotide strand or the second polynucleotide strand does not match the subsequent hash value of the sequenced set of nucleotides, provide an indication of a hash value mismatch.

Yet another implementation relates to a system for non-volatile polynucleotide storage comprising: a storage controller comprising a processor and a memory; a storage device comprising: a flow cell comprising a plurality of wells with open sides accessible from a first surface of the flow cell, wherein the wells are adapted to contain polynucleotides, a fluidics interface, and a sequencing interface; a fluidics device to provide one or more fluids to the first surface of the flow cell, wherein the one or more fluids comprise a nucleotide writing reagent and a nucleotide reading reagent; a sequencing device to sequence polynucleotides within the plurality of wells via the sequencing interface and determine nucleotides; and a cache memory comprising an electronic memory to store data that is queued to be encoded into a set of nucleotides and synthesized into polynucleotides in the plurality of wells.

Variations on any one or more of the above implementations exist, wherein the cache memory is positioned in the storage device, and wherein the storage device is a removable storage device.

Variations on any one or more of the above implementations exist, wherein the cache memory stores one or more of: a set of file indexes describing the name and location of data stored as polynucleotides within the plurality of wells, and a set of checksum values usable to verify the integrity of data stored as polynucleotides within the plurality of wells.

Variations on any one or more of the above implementations exist, wherein the storage controller: receives a set of input data to be written to the storage device as polynucleotides in the plurality of wells, receives a request for output data to be read from polynucleotides stored in the plurality of wells, determines whether the storage device is in a write-mode or a read-mode based upon whether it has most recently received the nucleotide writing reagent or the nucleotide reading reagent from the fluidics device, where the storage device is in the write-mode, writes the set of input data prior to reading the output data, and where the storage device is in the read-mode, stores the set of input data on the cache memory and read the output data prior to writing the set of input data.

Variations on any one or more of the above implementations exist, further comprising an electro-wetting device positioned proximately to the first surface and to deliver fluid from the fluidics device to any well of the plurality of wells, wherein the storage controller: operates the electro-wetting device to provide a droplet of the nucleotide reading reagent to a first well of the plurality of wells to enable sequencing the polynucleotides stored therein, while providing the droplet of the nucleotide reading reagent to the first well, identifies a second well, based upon a plurality of requests for output data, that is most proximately located to the first well, and operates the electro-wetting device to provide a portion of the droplet of the nucleotide reading reagent to the second well of the plurality of wells to enable sequencing of the polynucleotides stored therein.

Variations on any one or more of the above implementations exist, wherein the storage controller: determines a subset of the plurality of wells that are most frequently sequenced based upon past requests for output data, operate the sequencing device to sequence the subset of the plurality of wells and produce a set of nucleotides describing the polynucleotides stored in the subset of the plurality of wells, convert the set of nucleotides into a set of digital data, store the set of digital data in the cache memory, and provide the set of digital data from the cache memory in response to subsequent requests.

Yet another implementation relates to a system for non-volatile polynucleotide storage comprising: a storage controller comprising a processor and a memory; a storage device comprising: a first flow cell comprising a first plurality of wells, wherein the first plurality of wells are adapted to contain polynucleotides, a second flow cell comprising a second plurality of wells, wherein the second plurality of wells are adapted to contain polynucleotides, a fluidics interface, and a sequencing interface; a fluidics device to provide one or more fluids to the first plurality of wells and the second plurality of wells, wherein the one or more fluids comprise a nucleotide writing reagent and a nucleotide reading reagent; and a sequencing device to sequence polynucleotides within the first plurality of wells and the second plurality of wells via the sequencing interface and determine nucleotides wherein the storage controller, when in a mirroring mode: converts a set of data into a set of nucleotides, and operates the fluidics device to create identical polynucleotides in the first plurality of wells and the second plurality of wells based on the set of data.

Variations on any one or more of the above implementations exist, further comprising a spatial light modulator to project optical patterns onto the first flow cell and the second flow cell via the sequencing interface, wherein the storage controller operates the spatial light modulator to project an identical optical pattern into a first well of the first plurality of wells and a second well of the second plurality of wells to synthesize a first polynucleotide strand and a second polynucleotide strand.

Variations on any one or more of the above implementations exist, wherein the storage controller, when in a dedicated mode: converts the set of data into a set of nucleotides, designates the first plurality of wells for writing of data and designates the second plurality of wells for reading of data, operates the fluidics device to create polynucleotides in the first plurality of wells based on the set of data, and operates the fluidics device and the sequencing device to sequence polynucleotides in the second plurality of wells based upon an output request.

Variations on any one or more of the above implementations exist, wherein the storage controller: determines that there are no current output requests, and switches from the dedicate mode to the mirroring mode.

Another implementation relates to a method for risk mitigation for errors in a storage device. In such an implementation, the method may comprise generating one or more commands to write specified data to a polynucleotide associated with a particular location in the storage device. The method may also comprise reading the polynucleotide and performing a comparison. In such implementations, the comparison may compare the polynucleotide stored in the storage device with a particular quality control value stored in a non-nucleotide memory. In some such implementations, based on that comparison, the method may include determining if the particular location in the storage device is to be treated as having corrupted data.

Variations on any one or more of the above implementations exist wherein reading the polynucleotide, performing the comparison, and determining if the particular location in the storage device is to be treated as having corrupted data are performed automatically based on receiving a command to write to the storage device.

Variations on any one or more of the above implementations exist wherein the method may comprise determining that the particular location in the storage device is to be treated as having corrupted data. In some such implementation, the method may comprise, based on determining that the particular location in the storage device is to be treated as having corrupted data, writing a new polynucleotide encoding uncorrupted data to the particular location in the storage device.

Variations on any one or more of the above implementations exist wherein the method may comprise generating the uncorrupted data based on reading information from one or more other locations in the storage device.

Variations on any one or more of the above implementations exist wherein the method may comprise, based on determining that the particular location in the storage device is to be treated as having corrupted data, and before writing the new polynucleotide encoding uncorrupted data to the particular location in the storage device, updating an index for the storage device to indicate that the particular location in the storage device has corrupted data. In some such implementations, the method may comprise, after writing the new polynucleotide encoding uncorrupted data to the particular location in the storage device, updating the index for the storage device to indicate that the particular location in the storage device does not have corrupted data.

Variations on any one or more of the above implementations exist wherein the method may comprise generating the particular quality control value based on the specified data.

Variations on any one or more of the above implementations exist wherein the storage device may comprise a plurality of addressable locations. In some such implementations, the particular location may be comprised by the plurality of addressable locations. In some such implementations, the non-nucleotide memory may store a plurality of quality control values. In some such implementations, the particular quality control value is comprised by the plurality of quality control values. In some such implementations, each quality control value from the plurality of quality control values is associated with a corresponding addressable location from the plurality of addressable locations.

Variations on any one or more of the above implementations exist wherein the polynucleotide may comprise a check portion. In some such implementations, the method may comprise generating the check portion based on the specified data.

Variations on any one or more of the above implementations exist wherein the check portion may be a parity bit.

Variations on any one or more of the above implementations exist wherein the check portion may comprise a methylation or other information preserving modification of a nucleobase in the polynucleotide.

Variations on any one or more of the above implementations exist wherein the check portion may encode data matching the particular quality control value.

Variations on any one or more of the above implementations exist wherein a second polynucleotide may be stored in the storage device, and the second polynucleotide may comprise a second check portion identical to the check portion comprised by the polynucleotide. In some such implementations, the method may comprise, based on identifying a difference between the first polynucleotide and the second polynucleotide, determining that the particular location in the storage device is to be treated as having corrupted data.

Variations on any one or more of the above implementations exist wherein the particular quality control value may be the specified data. In some such implementations, the comparison may comprise checking if there are any differences between data stored in the polynucleotide and the specified data.

Variations on any one or more of the above implementations exist wherein the method may comprise determining that the particular location in the storage device should not be treated as having corrupted data. In some such implementations, the method may comprise, based on determining that the particular location in the storage device should not be treated as having corrupted data, deleting the particular quality control value stored in the non-nucleotide memory.

Another implementation relates to a system comprising a storage device with one or more non-transitory computer readable media storing instructions for the storage device to perform a method. In some such implementations, the method may comprise generating one or more commands to write specified data to a polynucleotide associated with a particular location in a storage device. In some such implementations, the method may comprise reading the polynucleotide and performing a comparison. In some such implementations, the comparison may compare the polynucleotide stored in the storage device with a particular quality control value stored in a non-nucleotide memory. In some such implementations, the method may comprise, based on the comparison, determining if the particular location in the storage device is to be treated as having corrupted data.

Variations on any one or more of the above implementations exist wherein the method may comprise reading the polynucleotide, performing the comparison, and determining if the particular location in the storage device is to be treated as having corrupted data automatically based on receiving a command to write to the storage device.

Variations on any one or more of the above implementations exist wherein the method may comprise determining that the particular location in the storage device is to be treated as having corrupted data. In some such implementations, the method may comprise, based on determining that the particular location in the storage device is to be treated as having corrupted data, writing a new polynucleotide encoding uncorrupted data to the particular location in the storage device.

Variations on any one or more of the above implementations exist wherein the method may comprise generating the uncorrupted data based on reading information from one or more other locations in the storage device.

Variations on any one or more of the above implementations exist wherein the method may comprise, based on determining that the particular location in the storage device is to be treated as having corrupted data, and before writing the new polynucleotide encoding uncorrupted data to the particular location in the storage device, updating an index for the storage device to indicate that the particular location in the storage device has corrupted data. In some such implementations, the method may comprise, after writing the new polynucleotide encoding uncorrupted data to the particular location in the storage device, updating the index for the storage device to indicate that the particular location in the storage device does not have uncorrupted data.

Variations on any one or more of the above implementations exist wherein the method may comprise generating the particular quality control value based on the specified data.

Variations on any one or more of the above implementations exist wherein the storage device may comprise a plurality of addressable locations. In some such implementations, the particular location may be comprised by the plurality of addressable locations. In some such implementations, the non-nucleotide memory may store a plurality of quality control values. In some such implementations, the particular quality control value is comprised by the plurality of quality control values. In some such implementations, each quality control value from the plurality of quality control values is associated with a corresponding addressable location from the plurality of addressable locations.

Variations on any one or more of the above implementations exist wherein the polynucleotide may comprise a check portion. In some such implementations, the method may comprise generating the check portion based on the specified data.

Variations on any one or more of the above implementations exist wherein the check portion may be a parity bit.

Variations on any one or more of the above implementations exist wherein the check portion may comprise a methylation or other information preserving modification of a nucleobase in the polynucleotide.

Variations on any one or more of the above implementations exist wherein the check portion may encode data matching the particular quality control value.

Variations on any one or more of the above implementations exist wherein a second polynucleotide may be stored in the storage device, and the second polynucleotide may comprise a second check portion identical to the check portion comprised by the polynucleotide. In some such implementations, the method may comprise, based on identifying a difference between the first polynucleotide and the second polynucleotide, determining that the particular location in the storage device is to be treated as having corrupted data.

Variations on any one or more of the above implementations exist wherein the particular quality control value may be the specified data. In some such implementations, the comparison may comprise checking if there are any differences between data stored in the polynucleotide and the specified data.

Variations on any one or more of the above implementations exist wherein the method may comprise determining that the particular location in the storage device should not be treated as having corrupted data. In some such implementations, the method may comprise, based on determining that the particular location in the storage device should not be treated as having corrupted data, deleting the particular quality control value stored in the non-nucleotide memory.

Yet another implementation relates to one or more non-transitory computer readable media storing instructions for a storage device to perform a method. In some such implementations, the method may comprise generating one or more commands to write specified data to a polynucleotide associated with a particular location in a storage device. In some such implementations, the method may comprise reading the polynucleotide and performing a comparison. In some such implementations, the comparison may compare the polynucleotide stored in the storage device with a particular quality control value stored in a non-nucleotide memory. In some such implementations, the method may comprise, based on the comparison, determining if the particular location in the storage device is to be treated as having corrupted data.

Variations on any one or more of the above implementations exist wherein the method may comprise reading the polynucleotide, performing the comparison, and determining if the particular location in the storage device is to be treated as having corrupted data automatically based on receiving a command to write to the storage device.

Variations on any one or more of the above implementations exist wherein the method may comprise determining that the particular location in the storage device is to be treated as having corrupted data. In some such implementations, the method may comprise, based on determining that the particular location in the storage device is to be treated as having corrupted data, writing a new polynucleotide encoding uncorrupted data to the particular location in the storage device.

Variations on any one or more of the above implementations exist wherein the method may comprise generating the uncorrupted data based on reading information from one or more other locations in the storage device.

Variations on any one or more of the above implementations exist wherein the method may comprise, based on determining that the particular location in the storage device is to be treated as having corrupted data, and before writing the new polynucleotide encoding uncorrupted data to the particular location in the storage device, updating an index for the storage device to indicate that the particular location in the storage device has corrupted data. In some such implementations, the method may comprise, after writing the new polynucleotide encoding uncorrupted data to the particular location in the storage device, updating the index for the storage device to indicate that the particular location in the storage device does not have uncorrupted data.

Variations on any one or more of the above implementations exist wherein the method may comprise generating the particular quality control value based on the specified data.

Variations on any one or more of the above implementations exist wherein the storage device may comprise a plurality of addressable locations. In some such implementations, the particular location may be comprised by the plurality of addressable locations. In some such implementations, the non-nucleotide memory may store a plurality of quality control values. In some such implementations, the particular quality control value is comprised by the plurality of quality control values. In some such implementations, each quality control value from the plurality of quality control values is associated with a corresponding addressable location from the plurality of addressable locations.

Variations on any one or more of the above implementations exist wherein the polynucleotide may comprise a check portion. In some such implementations, the method may comprise generating the check portion based on the specified data.

Variations on any one or more of the above implementations exist wherein the check portion may be a parity bit.

Variations on any one or more of the above implementations exist wherein the check portion may comprise a methylation or other or other information preserving modification of a nucleobase in the polynucleotide.

Variations on any one or more of the above implementations exist wherein the check portion may encode data matching the particular quality control value.

Variations on any one or more of the above implementations exist wherein a second polynucleotide may be stored in the storage device, and the second polynucleotide may comprise a second check portion identical to the check portion comprised by the polynucleotide. In some such implementations, the method may comprise, based on identifying a difference between the first polynucleotide and the second polynucleotide, determining that the particular location in the storage device is to be treated as having corrupted data.

Variations on any one or more of the above implementations exist wherein the particular quality control value may be the specified data. In some such implementations, the comparison may comprise checking if there are any differences between data stored in the polynucleotide and the specified data.

Variations on any one or more of the above implementations exist wherein the method may comprise determining that the particular location in the storage device should not be treated as having corrupted data. In some such implementations, the method may comprise, based on determining that the particular location in the storage device should not be treated as having corrupted data, deleting the particular quality control value stored in the non-nucleotide memory.

It should be appreciated that all combinations of the foregoing concepts and additional concepts discussed in greater detail below (provided such concepts are not mutually inconsistent) are contemplated as being part of the inventive subject matter disclosed herein and to achieve the benefits/advantages as described herein. In particular, all combinations of claimed subject matter appearing at the end of this disclosure are contemplated as being part of the inventive subject matter disclosed herein.

BRIEF DESCRIPTION OF THE DRAWINGS

The details of one or more implementations are set forth in the accompanying drawings and the description below. Other features, aspects, and advantages will become apparent from the description, the drawings, and the claims, in which:

Figure 1:
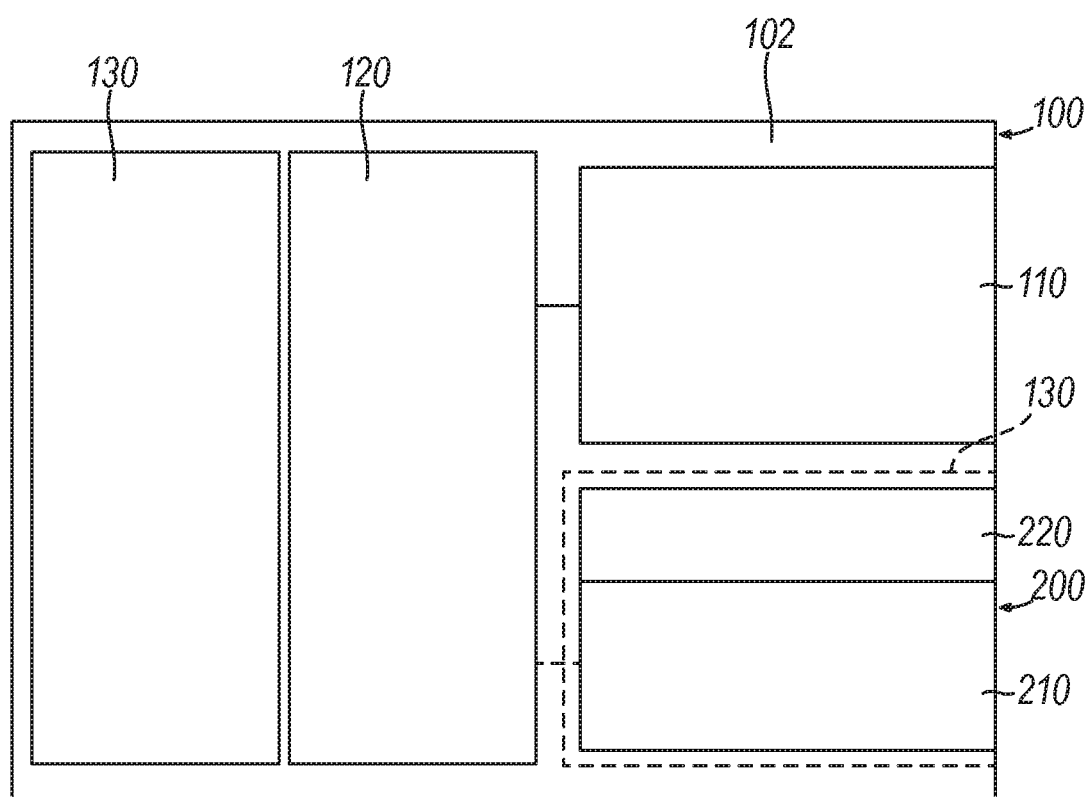
FIG. 1 depicts a block schematic view of an example of a system that may be used to conduct biochemical processes.

It will be recognized that some or all of the figures are schematic representations for purposes of illustration. The figures are provided for the purpose of illustrating one or more implementations with the explicit understanding that they will not be used to limit the scope or the meaning of the claims.

DETAILED DESCRIPTION

In some aspects, methods and systems are disclosed herein for providing selective activation of storage wells, simultaneous well reading and writing, and mitigation of data errors in a DNA storage device containing machine-written DNA, as well as for synthesizing DNA (or other biological material) to store data or other information; and/or reading machine-written DNA (or other biological material) to retrieve the machine-written data or other information. Machine-written DNA may provide an alternative to traditional forms of data storage (e.g., magnetic storage, optical storage, and solid-state storage). Machine-written DNA may provide faster read-write speeds, longer data retention, reduced power usage, and higher data density. While examples described herein refer to a "DNA storage system" or a "DNA storage device," it should be understood that this is only one example of polynucleotide storage. The teachings herein may be readily applied to storage systems and devices that utilize polynucleotides that are not necessarily in the form of DNA. The invention is thus not limited to using DNA as the only kind of polynucleotides for storage as described herein. Moreover, polynucleotides are only one example of biological material that may be used for storage as described herein.

Examples of how digital information may be stored in DNA are disclosed in U.S. Pub. No. 2015/0261664, entitled "High-Capacity of Storage of Digital Information in DNA," published Sep. 17, 2015, which is incorporated by reference herein in its entirety. For example, methods from code theory to enhance the recoverability of the encoded messages from the DNA segment, including forbidding DNA homopolymers (i.e. runs of more than one identical base)

that are known to be associated with higher error rates in existing high throughput technologies may be used. Further, an error-detecting component, analogous to a parity-check bit, may be integrated into the indexing information in the code. More complex schemes, including but not limited to error-correcting codes and, indeed, substantially any form of digital data security (e.g., RAID-based schemes) currently employed in informatics, may be implemented in future developments of the DNA storage scheme. The DNA encoding of information may be computed using software. The bytes comprising each computer file may be represented by a DNA sequence with no homopolymers by an encoding scheme to produce an encoded file that replaces each byte by five or six bases forming the DNA sequence.

The code used in the encoding scheme may be constructed to permit a straightforward encoding that is close to the optimum information capacity for a run length-limited channel (e.g., no repeated nucleotides), though other encoding schemes may be used. The resulting in silico DNA sequences may be too long to be readily produced by standard oligonucleotide synthesis and may be split into overlapping segments of a length of 100 bases with an overlap of 75 bases. To reduce the risk of systematic synthesis errors introduced to any particular run of bases, alternate ones of the segments may be converted to their reverse complement, meaning that each base may be "written" four times, twice in each direction. Each segment may then be augmented with an indexing information that permits determination of the computer file from which the segment originated and its location within that computer file, plus simple error-detection information. This indexing information may also be encoded in as non-repeating DNA nucleotides and appended to the information storage bases of the DNA segments. The division of the DNA segments into lengths of 100 bases with an overlap of 75 bases is purely arbitrary and illustrative, and it is understood that other lengths and overlaps may be used and is not limiting.

Other encoding schemes for the DNA segments may be used, for example to provide enhanced error-correcting properties. The amount of indexing information may be increased in order to allow more or larger files to be encoded. One extension to the coding scheme in order to avoid systematic patterns in the DNA segments may be to add change the information. One way may use the "shuffling" of information in the DNA segments, where the information may be retrieved if one knows the pattern of shuffling. Different patterns of shuffles may be used for different ones of the DNA segments. A further way is to add a degree of randomness into the information in each one of the DNA segments. A series of random digits may be used for this, using modular addition of the series of random digits and the digits comprising the information encoded in the DNA segments. The information may be retrieved by modular subtraction during decoding if one knows the series of random digits used. Different series of random digits may be used for different ones of the DNA segments The data-encoding component of each string may contain Shannon information at 5.07 bits per DNA base, which is close to the theoretical optimum of 5.05 bits per DNA base for base-4 channels with run length limited to one. The indexing implementation may permit $3^{14}=4782969$ unique data locations. Increasing the number of indexing trits (and therefore bases) used to specify file and intra-file location by just two, to 16, gives $3^{16}=43046721$ unique locations, in excess of the 16.8M that is the practical maximum for the Nested Primer Molecular Memory (NPMM) scheme.

The DNA segment designs may be synthesized in three distinct runs (with the DNA segments randomly assigned to runs) to create approx. $1.2 \times 10^7$ copies of each DNA segment design. Phosphoramidite chemistry may be used, and inkjet printing and flow cell reactor technologies in an in-situ microarray synthesis platform may be employed. The inkjet printing within an anhydrous chamber may allow the delivery of very small volumes of phosphoramidites to a confined coupling area on a 2D planar surface, resulting in the addition of hundreds of thousands of bases in parallel. Subsequent oxidation and detritylation may be carried out in a flow cell reactor. Once DNA synthesis is completed, the oligonucleotides may then be cleaved from the surface and deprotected.

Adapters may then be added to the DNA segments to enable a plurality of copies of the DNA segments to be made. A DNA segment with no adapter may require additional chemical processes to "kick start" the chemistry for the synthesis of the multiple copies by adding additional groups onto the ends of the DNA segments. Oligonucleotides may be amplified using polymerase chain reaction (PCR) methods and paired-end PCR primers, followed by bead purification and quantification. Oligonucleotides may then be sequenced to produce reads of 104 bases. The digital information decoding may then be carried out via sequencing of the central bases of each oligo from both ends and rapid computation of full-length oligos and removal of sequence reads inconsistent with the designs. Sequence reads may be decoded using computer software that exactly reverses the encoding process. Sequence reads for which the parity-check trit indicates an error or that may be unambiguously decoded or assigned to a reconstructed computer file may be discarded. Locations within every decoded file may be detected in multiple different sequenced DNA oligos, and simple majority voting may be used to resolve any discrepancies caused by the DNA synthesis or the sequencing errors.

While several examples herein are provided in the context of machine-written DNA, it is contemplated that the principles described herein may be applied to other kinds of machine-written biological material.

As used herein, the term "machine-written DNA" shall be read to include one or more strands of polynucleotides that are generated by a machine, or otherwise modified by a machine, to store data or other information. One example of the polynucleotide herein is a DNA. It is noted that while the term "DNA" in the context of DNA being read or written is used throughout this disclosure, the term is used only as a representative example of a polynucleotide and may encompass the concept of a polynucleotide. "Machine," as used herein in reference to "machine-written," may include an instrument or system specially designed for writing DNA as described in greater detail herein. The system may be non-biological or biological. In one example, the biological system may comprise, or is, a polymerase. For example, the polymerase may be terminal deoxynucleotidyl transferase (TdT). In a biological system, the process may be additionally controlled by a machine hardware (e.g., processor) or an algorithm. "Machine-written DNA" may include any polynucleotide having one or more base sequences written by a machine. While machine-written DNA is used herein as an example, other polynucleotide strands may be substituted for machine-written DNA described herein. "Machine-written DNA" may include natural bases and modifications of natural bases, including but not limited to bases modified with methylation or other chemical tags; an artificially synthesized polymer that is similar to DNA, such as peptide nucleic acid (PNA); or Morpholino DNA. "Machine-written DNA" may also include DNA strands or other polynucleotides that are formed by at least one strand of bases originating from nature (e.g., extracted from a naturally occurring organism), with a machine-written strand of bases secured thereto either in a parallel fashion or in an end-to-end fashion. In other implementations, "machine-written DNA" may be written by a biological system (e.g., enzyme) in lieu of, or in addition to, a non-biological system (e.g., the electrode machine) writing of DNA described herein. In other words, "machine-written DNA" may be written directly by a machine; or by an enzyme (e.g., polymerase) that is controlled by an algorithm and/or machine.

"Machine-written DNA" may include data that have been converted from a raw form (e.g., a photograph, a text document, etc.) into a binary code sequence using known techniques, with that binary code sequence then being converted to a DNA base sequence using known techniques, and with that DNA base sequence then being generated by a machine in the form of one or more DNA strands or other polynucleotides. Alternatively, "machine-written DNA" may be generated to index or otherwise track pre-existing DNA, to store data or information from any other source and for any suitable purpose, without necessarily requiring an intermediate step of converting raw data to a binary code.

As described in greater detail below, machine-written DNA may be written to and/or read from a reaction site. As used herein, the term "reaction site" is a localized region where at least one designated reaction may occur. A reaction site may include support surfaces of a reaction structure or substrate where a substance may be immobilized thereon. For instance, the reaction site may be a discrete region of space where a discrete group of DNA strands or other polynucleotides are written. The reaction site may permit chemical reactions that are isolated from reactions that are in adjacent reaction sites. Devices that provide machine-writing of DNA may include flow cells with wells having writing features (e.g., electrodes) and/or reading features. In some instances, the reaction site may include a surface of a reaction structure (which may be positioned in a channel of a flow cell) that already has a reaction component thereon, such as a colony of polynucleotides thereon. In some flow cells, the polynucleotides in the colony have the same sequence, being for example, clonal copies of a single stranded or double stranded template. However, in some flow cells a reaction site may contain only a single polynucleotide molecule, for example, in a single stranded or double stranded form.

A plurality of reaction sites may be randomly distributed along the reaction structure of the flow cells or may be arranged in a predetermined manner (e.g., side-by-side in a matrix, such as in microarrays). A reaction site may also include a reaction chamber, recess, or well that at least partially defines a spatial region or volume configured to compartmentalize the designated reaction. As used herein, the term "reaction chamber" or "reaction recess" includes a defined spatial region of the support structure (which is often fluidically coupled with a flow channel). A reaction recess may be at least partially separated from the surrounding environment or other spatial regions. For example, a plurality of reaction recesses may be separated from each other by shared walls. As a more specific example, the reaction recesses may be nanowells comprising an indent, pit, well, groove, cavity or depression defined by interior surfaces of a detection surface and have an opening or aperture (i.e., be open-sided) so that the nanowells may be fluidically coupled with a flow channel.

A plurality of reaction sites may be randomly distributed along the reaction structure of the flow cells or may be arranged in a predetermined manner (e.g., side-by-side in a matrix, such as in microarrays). A reaction site may also include a reaction chamber, recess, or well that at least partially defines a spatial region or volume configured to compartmentalize the designated reaction. As used herein, the term "reaction chamber" or "reaction recess" includes a defined spatial region of the support structure (which is often fluidically coupled with a flow channel). A reaction recess may be at least partially separated from the surrounding environment or other spatial regions. For example, a plurality of reaction recesses may be separated from each other by shared walls. As a more specific example, the reaction recesses may be nanowells comprising an indent, pit, well, groove, cavity or depression defined by interior surfaces of a detection surface and have an opening or aperture (i.e., be open-sided) so that the nanowells may be fluidically coupled with a flow channel.

To read the machine-written DNA, one or more discrete detectable regions of reaction sites may be defined. Such detectable regions may be imageable regions, electrical detection regions, or other types of regions that may have a measurable change in a property (or absence of change in the property) based on the type of nucleotide present during the reading process.

As used herein, the term "pixel" refers to a discrete imageable region. Each imageable region may include a compartment or discrete region of space where a polynucleotide is present. In some instances, a pixel may include two or more reaction sites (e.g., two or more reaction chambers, two or more reaction recesses, two or more wells, etc.). In some other instances, a pixel may include just one reaction site. Each pixel is detected using a corresponding detection device, such as an image sensor or other light detection device. The light detection device may be manufactured using integrated circuit manufacturing processes, such as processes used to manufacture charged-coupled devices circuits (CCD) or complementary-metal-oxide semiconductor (CMOS) devices or circuits. The light detection device may thereby include, for example, one or more semiconductor materials, and may take the form of, for example, a CMOS light detection device (e.g., a CMOS image sensor) or a CCD image sensor, another type of image sensor. A CMOS image sensor may include an array of light sensors (e.g. photodiodes). In one implementation, a single image sensor may be used with an objective lens to capture several "pixels," during an imaging event. In some other implementations, each discrete photodiode or light sensor may capture a corresponding pixel. In some implementations, light sensors (e.g., photodiodes) of one or more detection devices may be associated with corresponding reaction sites. A light sensor that is associated with a reaction site may detect light emissions from the associated reaction site. In some implementations, the detection of light emissions may be done via at least one light guide when a designated reaction has occurred at the associated reaction site. In some implementations, a plurality of light sensors (e.g., several pixels of a light detection or camera device) may be associated with a single reaction site. In some implementations, a single light sensor (e.g. a single pixel) may be associated with a single reaction site or with a group of reaction sites.

As used herein, the term "synthesis" shall be read to include processes where DNA is generated by a machine to store data or other information. Thus, machine-written DNA may constitute synthesized DNA. As used herein, the terms "consumable cartridge," "reagent cartridge," "removeable cartridge," and/or "cartridge" refer to the same cartridge and/or a combination of components making an assembly for a cartridge or cartridge system. The cartridges described herein may be independent of the element with the reaction sites, such as a flow cell having a plurality of wells. In some instances, a flow cell may be removably inserted into a cartridge, which is then inserted into an instrument. In some other implementations, the flow cell may be removably inserted into the instrument without a cartridge. As used herein, the term "biochemical analysis" may include at least one of biological analysis or chemical analysis.

The term "based on" should be understood to mean that something is determined at least in part by the thing it is indicated as being "based on." To indicate that something must necessarily be completely determined by something else, it is described as being based exclusively on whatever it is completely determined by.

The term "non-nucleotide memory" should be understood to refer to an object, device or combination of devices capable of storing data or instructions in a form other than nucleotides that may be retrieved and/or processed by a device. Examples of "non-nucleotide memory" include solid state memory, magnetic memory, hard drives, optical drives and combinations of the foregoing (e.g., magneto-optical storage elements).

The term "DNA storage device" should be understood to refer to an object, device, or combination of devices configured to store data or instructions in the form of sequences of polynucleotides such as machine-written DNA. Examples of "DNA storage devices" include flow cells having addressable wells as described herein, systems comprising multiple such flow cells, and tubes or other containers storing nucleotide sequences that have been cleaved from the surface on which they were synthesized. As used herein, the term "nucleotide sequence" or "polynucleotide sequence" should be read to include a polynucleotide molecule, as well as the underlying sequence of the molecule, depending on context. A sequence of a polynucleotide may contain (or encode) information indicative of certain physical characteristics.

Implementations set forth herein may be used to perform designated reactions for consumable cartridge preparation and/or biochemical analysis and/or synthesis of machine-written DNA.

I. System Overview

FIG. 1 is a schematic diagram of a system 100 that is configured to conduct biochemical analysis and/or synthesis. The system 100 may include a base instrument 102 that is configured to receive and separably engage a removable cartridge 200 and/or a component with one or more reaction sites. The base instrument 102 and the removable cartridge 200 may be configured to interact with each other to transport a biological material to different locations within the system 100 and/or to conduct designated reactions that include the biological material in order to prepare the biological material for subsequent analysis (e.g., by synthesizing the biological material), and, optionally, to detect one or more events with the biological material. In some implementations, the base instrument 102 may be configured to detect one or more events with the biological material directly on the removable cartridge 200. The events may be indicative of a designated reaction with the biological material. The removable cartridge 200 may be constructed according to any of the cartridges described herein.

Although the following is with reference to the base instrument 102 and the removable cartridge 200 as shown in FIG. 1, it is understood that the base instrument 102 and the removable cartridge 200 illustrate only one implementation of the system 100 and that other implementations exist. For example, the base instrument 102 and the removable cartridge 200 include various components and features that, collectively, execute several operations for preparing the biological material and/or analyzing the biological material. Moreover, although the removable cartridge 200 described herein includes an element with the reaction sites, such as a flow cell having a plurality of wells, other cartridges may be independent of the element with the reaction sites and the element with the reaction sites may be separately insertable into the base instrument 102. That is, in some instances a flow cell may be removably inserted into the removable cartridge 200, which is then inserted into the base instrument 102. In some other implementations, the flow cell may be removably inserted directly into the base instrument 102 without the removable cartridge 200. In still further implementations, the flow cell may be integrated into the removable cartridge 200 that is inserted into the base instrument 102.

In the illustrated implementation, each of the base instrument 102 and the removable cartridge 200 are capable of performing certain functions. It is understood, however, that the base instrument 102 and the removable cartridge 200 may perform different functions and/or may share such functions. For example, the base instrument 102 is shown to include a detection assembly 110 (e.g., an imaging device) that is configured to detect the designated reactions at the removable cartridge 200. In alternative implementations, the removable cartridge 200 may include the detection assembly and may be communicatively coupled to one or more components of the base instrument 102. As another example, the base instrument 102 is a "dry" instrument that does not provide, receive, or exchange liquids with the removable cartridge 200. That is, as shown, the removable cartridge 200 includes a consumable reagent portion 210 and a flow cell receiving portion 220. The consumable reagent portion 210 may contain reagents used during biochemical analysis and/or synthesis. The flow cell receiving portion 220 may include an optically transparent region or other detectible region for the detection assembly 110 to perform detection of one or more events occurring within the flow cell receiving portion 220. In alternative implementations, the base instrument 102 may provide, for example, reagents or other liquids to the removable cartridge 200 that are subsequently consumed (e.g., used in designated reactions or synthesis procedures) by the removable cartridge 200.

As used herein, the biological material may include one or more biological or chemical substances, such as nucleosides, nucleotides, nucleic acids, polynucleotides, oligonucleotides, proteins, enzymes, peptides, oligopeptides, polypeptides, antibodies, antigens, ligands, receptors, polysaccharides, carbohydrates, polyphosphates, nanopores, organelles, lipid layers, cells, tissues, organisms, and/or biologically active chemical compound(s), such as analogs or mimetics of the aforementioned species. In some instances, the biological material may include whole blood, lymphatic fluid, serum, plasma, sweat, tear, saliva, sputum, cerebrospinal fluid, amniotic fluid, seminal fluid, vaginal excretion, serous fluid, synovial fluid, pericardial fluid, peritoneal fluid, pleural fluid, transudates, exudates, cystic fluid, bile, urine, gastric fluid, intestinal fluid, fecal samples, liquids containing single or multiple cells, liquids containing organelles, fluidized tissues, fluidized organisms, viruses including viral pathogens, liquids containing multi-celled organisms, biological swabs and biological washes. In some instances, the biological material may include a set of synthetic sequences, including but not limited to machine-written DNA, which may be fixed (e.g., attached in specific wells in a cartridge) or unfixed (e.g., stored in a tube).

In some implementations, the biological material may include an added material, such as water, deionized water, saline solutions, acidic solutions, basic solutions, detergent solutions and/or pH buffers. The added material may also include reagents that will be used during the designated assay protocol to conduct the biochemical reactions. For example, added liquids may include material to conduct multiple polymerase-chain-reaction (PCR) cycles with the biological material. In other aspects, the added material may be a carrier for the biological material such as cell culture media or other buffered and/or pH adjusted and/or isotonic carrier that may allow for or preserve the biological function of the biological material.

It should be understood, however, that the biological material that is analyzed may be in a different form or state than the biological material loaded into or created by the system 100. For example, a biological material loaded into the system 100 may include whole blood or saliva or cell population that is subsequently treated (e.g., via separation or amplification procedures) to provide prepared nucleic acids. The prepared nucleic acids may then be analyzed (e.g., quantified by PCR or sequenced by SBS) by the system 100. Accordingly, when the term "biological material" is used while describing a first operation, such as PCR, and used again while describing a subsequent second operation, such as sequencing, it is understood that the biological material in the second operation may be modified with respect to the biological material prior to or during the first operation. For example, sequencing (e.g. SBS) may be carried out on amplicon nucleic acids that are produced from template nucleic acids that are amplified in a prior amplification (e.g. PCR). In this case the amplicons are copies of the templates and the amplicons are present in higher quantity compared to the quantity of the templates.

In some implementations, the system 100 may automatically prepare a sample for biochemical analysis based on a substance provided by the user (e.g., whole blood or saliva or a population of cells). However, in other implementations, the system 100 may analyze biological materials that are partially or preliminarily prepared for analysis by the user. For example, the user may provide a solution including nucleic acids that were already isolated and/or amplified from whole blood; or may provide a virus sample in which the RNA or DNA sequence is partially or wholly exposed for processing.

As used herein, a "designated reaction" includes a change in at least one of a chemical, electrical, physical, or optical property (or quality) of an analyte-of-interest. In particular implementations, the designated reaction is an associative binding event (e.g., incorporation of a fluorescently labeled biomolecule with the analyte-of-interest). The designated reaction may be a dissociative binding event (e.g., release of a fluorescently labeled biomolecule from an analyte-of-interest). The designated reaction may be a chemical transformation, chemical change, or chemical interaction. The designated reaction may also be a change in electrical properties. For example, the designated reaction may be a change in ion concentration within a solution. Some reactions include, but are not limited to, chemical reactions such as reduction, oxidation, addition, elimination, rearrangement, esterification, amidation, etherification, cyclization, or substitution; binding interactions in which a first chemical binds to a second chemical; dissociation reactions in which two or more chemicals detach from each other; fluorescence; luminescence; bioluminescence; chemiluminescence; and biological reactions, such as nucleic acid replication, nucleic acid amplification, nucleic acid hybridization, nucleic acid ligation, phosphorylation, enzymatic catalysis, receptor binding, or ligand binding. The designated reaction may also be addition or removal of a proton, for example, detectable as a change in pH of a surrounding solution or environment. An additional designated reaction may be detecting the flow of ions across a membrane (e.g., natural or synthetic bilayer membrane). For example, as ions flow through a membrane, the current is disrupted, and the disruption may be detected. Field sensing of charged tags may also be used; as may thermal sensing and other suitable analytical sensing techniques.

In particular implementations, the designated reaction includes the incorporation of a fluorescently labeled molecule to an analyte. The analyte may be an oligonucleotide and the fluorescently labeled molecule may be a nucleotide. The designated reaction may be detected when an excitation light is directed toward the oligonucleotide having the labeled nucleotide, and the fluorophore emits a detectable fluorescent signal. In alternative implementations, the detected fluorescence is a result of chemiluminescence and/or bioluminescence. A designated reaction may also increase fluorescence (or Forster) resonance energy transfer (FRET), for example, by bringing a donor fluorophore in proximity to an acceptor fluorophore, decrease FRET by separating donor and acceptor fluorophores, increase fluorescence by separating a quencher from a fluorophore or decrease fluorescence by co-locating a quencher and fluorophore.

As used herein, a "reaction component" includes any substance that may be used to obtain a designated reaction. For example, reaction components include reagents, catalysts such as enzymes, reactants for the reaction, samples, products of the reaction, other biomolecules, salts, metal cofactors, chelating agents, and buffer solutions (e.g., hydrogenation buffer). The reaction components may be delivered, individually in solutions or combined in one or more mixture, to various locations in a fluidic network. For instance, a reaction component may be delivered to a reaction chamber where the biological material is immobilized. The reaction components may interact directly or indirectly with the biological material. In some implementations, the removable cartridge 200 is preloaded with one or more of the reaction components involved in carrying out a designated assay protocol. Preloading may occur at one location (e.g. a manufacturing facility) prior to receipt of the cartridge 200 by a user (e.g. at a customer's facility). For example, the one or more reaction components or reagents may be preloaded into the consumable reagent portion 210. In some implementations, the removable cartridge 200 may also be preloaded with a flow cell in the flow cell receiving portion 220.

In some implementations, the base instrument 102 may be configured to interact with one removable cartridge 200 per session. After the session, the removable cartridge 200 may be replaced with another removable cartridge 200. In other implementations, the base instrument 102 may be configured to interact with more than one removable cartridge 200 per session. As used herein, the term "session" includes performing at least one of sample preparation and/or biochemical analysis protocol. Sample preparation may include synthesizing the biological material; and/or separating, isolating, modifying, and/or amplifying one or more components of the biological material so that the prepared biological material is suitable for analysis. In some implementations, a session may include continuous activity in which a number of controlled reactions are conducted until (a) a designated number of reactions have been conducted, (b) a designated number of events have been detected, (c) a designated period of system time has elapsed, (d) signal-to-noise has dropped to a designated threshold; (e) a target component has been identified; (f) system failure or malfunction has been detected; and/or (g) one or more of the resources for conducting the reactions has depleted. Alternatively, a session may include pausing system activity for a period of time (e.g., minutes, hours, days, weeks) and later completing the session until at least one of (a)-(g) occurs.

An assay protocol may include a sequence of operations for conducting the designated reactions, detecting the designated reactions, and/or analyzing the designated reactions. Collectively, the removable cartridge 200 and the base instrument 102 may include the components for executing the different operations. The operations of an assay protocol may include fluidic operations, thermal-control operations, detection operations, and/or mechanical operations.

A fluidic operation includes controlling the flow of fluid (e.g., liquid or gas) through the system 100, which may be actuated by the base instrument 102 and/or by the removable cartridge 200. In one example, the fluid is in liquid form. For example, a fluidic operation may include controlling a pump to induce flow of the biological material or a reaction component into a reaction chamber.

A thermal-control operation may include controlling a temperature of a designated portion of the system 100, such as one or more portions of the removable cartridge 200. By way of example, a thermal-control operation may include raising or lowering a temperature of a polymerase chain reaction (PCR) zone where a liquid that includes the biological material is stored.

A detection operation may include controlling activation of a detector or monitoring activity of the detector to detect predetermined properties, qualities, or characteristics of the biological material. As one example, the detection operation may include capturing images of a designated area that includes the biological material to detect fluorescent emissions from the designated area. The detection operation may include controlling a light source to illuminate the biological material or controlling a detector to observe the biological material.

A mechanical operation may include controlling a movement or position of a designated component. For example, a mechanical operation may include controlling a motor to move a valve-control component in the base instrument 102 that operably engages a movable valve in the removable cartridge 200. In some cases, a combination of different operations may occur concurrently. For example, the detector may capture images of the reaction chamber as the pump controls the flow of fluid through the reaction chamber. In some cases, different operations directed toward different biological materials may occur concurrently. For instance, a first biological material may be undergoing amplification (e.g., PCR) while a second biological material may be undergoing detection.

Similar or identical fluidic elements (e.g., channels, ports, reservoirs, etc.) may be labeled differently to more readily distinguish the fluidic elements. For example, ports may be referred to as reservoir ports, supply ports, network ports, feed port, etc. It is understood that two or more fluidic elements that are labeled differently (e.g., reservoir channel, sample channel, flow channel, bridge channel) do not require that the fluidic elements be structurally different. Moreover, the claims may be amended to add such labels to more readily distinguish such fluidic elements in the claims.

A "liquid," as used herein, is a substance that is relatively incompressible and has a capacity to flow and to conform to a shape of a container or a channel that holds the substance. A liquid may be aqueous-based and include polar molecules exhibiting surface tension that holds the liquid together. A liquid may also include non-polar molecules, such as in an oil-based or non-aqueous substance. It is understood that references to a liquid in the present application may include a liquid comprising the combination of two or more liquids. For example, separate reagent solutions may be later combined to conduct designated reactions.

One or more implementations may include retaining the biological material (e.g., template nucleic acid) at a designated location where the biological material is analyzed. As used herein, the term "retained," when used with respect to a biological material, includes attaching the biological material to a surface or confining the biological material within a designated space. As used herein, the term "immobilized," when used with respect to a biological material, includes attaching the biological material to a surface in or on a solid support. Immobilization may include attaching the biological material at a molecular level to the surface. For example, a biological material may be immobilized to a surface of a substrate using adsorption techniques including non-covalent interactions (e.g., electrostatic forces, van der Waals, and dehydration of hydrophobic interfaces) and covalent binding techniques where functional groups or linkers facilitate attaching the biological material to the surface. Immobilizing a biological material to a surface of a substrate may be based upon the properties of the surface of the substrate, the liquid medium carrying the biological material, and the properties of the biological material itself. In some cases, a substrate surface may be functionalized (e.g., chemically or physically modified) to facilitate immobilizing the biological material to the substrate surface. The substrate surface may be first modified to have functional groups bound to the surface. The functional groups may then bind to the biological material to immobilize the biological material thereon. In some cases, a biological material may be immobilized to a surface via a gel.

In some implementations, nucleic acids may be immobilized to a surface and amplified using bridge amplification. Another useful method for amplifying nucleic acids on a surface is rolling circle amplification (RCA), for example, using methods set forth in further detail below. In some implementations, the nucleic acids may be attached to a surface and amplified using one or more primer pairs. For example, one of the primers may be in solution and the other primer may be immobilized on the surface (e.g., 5'-attached). By way of example, a nucleic acid molecule may hybridize to one of the primers on the surface followed by extension of the immobilized primer to produce a first copy of the nucleic acid. The primer in solution then hybridizes to the first copy of the nucleic acid which may be extended using the first copy of the nucleic acid as a template. Optionally, after the first copy of the nucleic acid is produced, the original nucleic acid molecule may hybridize to a second immobilized primer on the surface and may be extended at the same time or after the primer in solution is extended. In any implementation, repeated rounds of extension (e.g., amplification) using the immobilized primer and primer in solution may be used to provide multiple copies of the nucleic acid. In some implementations, the biological material may be confined within a predetermined space with reaction components that are configured to be used during amplification of the biological material (e.g., PCR).

One or more implementations set forth herein may be configured to execute an assay protocol that is or includes an amplification (e.g., PCR) protocol. During the amplification protocol, a temperature of the biological material within a reservoir or channel may be changed in order to amplify a target sequence or the biological material (e.g., DNA of the biological material). By way of example, the biological material may experience (1) a pre-heating stage of about 95° C. for about 75 seconds; (2) a denaturing stage of about 95° C. for about 15 seconds; (3) an annealing-extension stage of about of about 59° C. for about 45 seconds; and (4) a temperature holding stage of about 72° C. for about 60 seconds. Implementations may execute multiple amplification cycles. It is noted that the above cycle describes only one particular implementation and that alternative implementations may include modifications to the amplification protocol.

The methods and systems set forth herein may use arrays having features at any of a variety of densities including, for example, at least about 10 features/cm$^2$, about 100 features/cm$^2$, about 500 features/cm$^2$, about 1,000 features/cm$^2$, about 5,000 features/cm$^2$, about 10,000 features/cm$^2$, about 50,000 features/cm$^2$, about 100,000 features/cm$^2$, about 1,000,000 features/cm$^2$, about 5,000,000 features/cm$^2$, or higher. The methods and apparatus set forth herein may include detection components or devices having a resolution that is at least sufficient to resolve individual features at one or more of these densities.

The base instrument 102 may include a user interface 130 that is configured to receive user inputs for conducting a designated assay protocol and/or configured to communicate information to the user regarding the assay. The user interface 130 may be incorporated with the base instrument 102. For example, the user interface 130 may include a touchscreen that is attached to a housing of the base instrument 102 and configured to identify a touch from the user and a location of the touch relative to information displayed on the touchscreen. Alternatively, the user interface 130 may be located remotely with respect to the base instrument 102.

II. Cartridge

The removable cartridge 200 is configured to separably engage or removably couple to the base instrument 102 at a cartridge chamber 140. As used herein, when the terms "separably engaged" or "removably coupled" (or the like) are used to describe a relationship between a removable cartridge 200 and a base instrument 102. The term is intended to mean that a connection between the removable cartridge 200 and the base instrument 102 are separable without destroying the base instrument 102. Accordingly, the removable cartridge 200 may be separably engaged to the base instrument 102 in an electrical manner such that the electrical contacts of the base instrument 102 are not destroyed. The removable cartridge 200 may be separably engaged to the base instrument 102 in a mechanical manner such that features of the base instrument 102 that hold the removable cartridge 200, such as the cartridge chamber 140, are not destroyed. The removable cartridge 200 may be separably engaged to the base instrument 102 in a fluidic manner such that the ports of the base instrument 102 are not destroyed. The base instrument 102 is not considered to be "destroyed," for example, if only a simple adjustment to the component (e.g., realigning) or a simple replacement (e.g., replacing a nozzle) is required. Components (e.g., the removable cartridge 200 and the base instrument 102) may be readily separable when the components may be separated from each other without undue effort or a significant amount of time spent in separating the components. In some implementations, the removable cartridge 200 and the base instrument 102 may be readily separable without destroying either the removable cartridge 200 or the base instrument 102.

In some implementations, the removable cartridge 200 may be permanently modified or partially damaged during a session with the base instrument 102. For instance, containers holding liquids may include foil covers that are pierced to permit the liquid to flow through the system 100. In such implementations, the foil covers may be damaged such that the damaged container is to be replaced with another container. In particular implementations, the removable cartridge 200 is a disposable cartridge such that the removable cartridge 200 may be replaced and optionally disposed after a single use. Similarly, a flow cell of the removable cartridge 200 may be separately disposable such that the flow cell may be replaced and optionally disposed after a single use.

In other implementations, the removable cartridge 200 may be used for more than one session while engaged with the base instrument 102 and/or may be removed from the base instrument 102, reloaded with reagents, and re-engaged to the base instrument 102 to conduct additional designated reactions. Accordingly, the removable cartridge 200 may be refurbished in some cases such that the same removable cartridge 200 may be used with different consumables (e.g., reaction components and biological materials). Refurbishing may be carried out at a manufacturing facility after the cartridge 200 has been removed from a base instrument 102 located at a customer's facility.

The cartridge chamber 140 may include a slot, mount, connector interface, and/or any other feature to receive the removable cartridge 200 or a portion thereof to interact with the base instrument 102.

The removable cartridge 200 may include a fluidic network that may hold and direct fluids (e.g., liquids or gases) therethrough. The fluidic network may include a plurality of interconnected fluidic elements that are capable of storing a fluid and/or permitting a fluid to flow therethrough. Non-limiting examples of fluidic elements include channels, ports of the channels, cavities, storage devices, reservoirs of the storage devices, reaction chambers, waste reservoirs, detection chambers, multipurpose chambers for reaction and detection, and the like. For example, the consumable reagent portion 210 may include one or more reagent wells or chambers storing reagents and may be part of or coupled to the fluidic network. The fluidic elements may be fluidically coupled to one another in a designated manner so that the system 100 is capable of performing sample preparation and/or analysis.

As used herein, the term "fluidically coupled" (or like term) refers to two spatial regions being connected together such that a liquid or gas may be directed between the two spatial regions. In some cases, the fluidic coupling permits a fluid to be directed back and forth between the two spatial regions. In other cases, the fluidic coupling is uni-directional such that there is only one direction of flow between the two spatial regions. For example, an assay reservoir may be fluidically coupled with a channel such that a liquid may be transported into the channel from the assay reservoir. However, in some implementations, it may not be possible to direct the fluid in the channel back to the assay reservoir. In particular implementations, the fluidic network may be configured to receive a biological material and direct the biological material through sample preparation and/or sample analysis. The fluidic network may direct the biological material and other reaction components to a waste reservoir.

Figure 2:
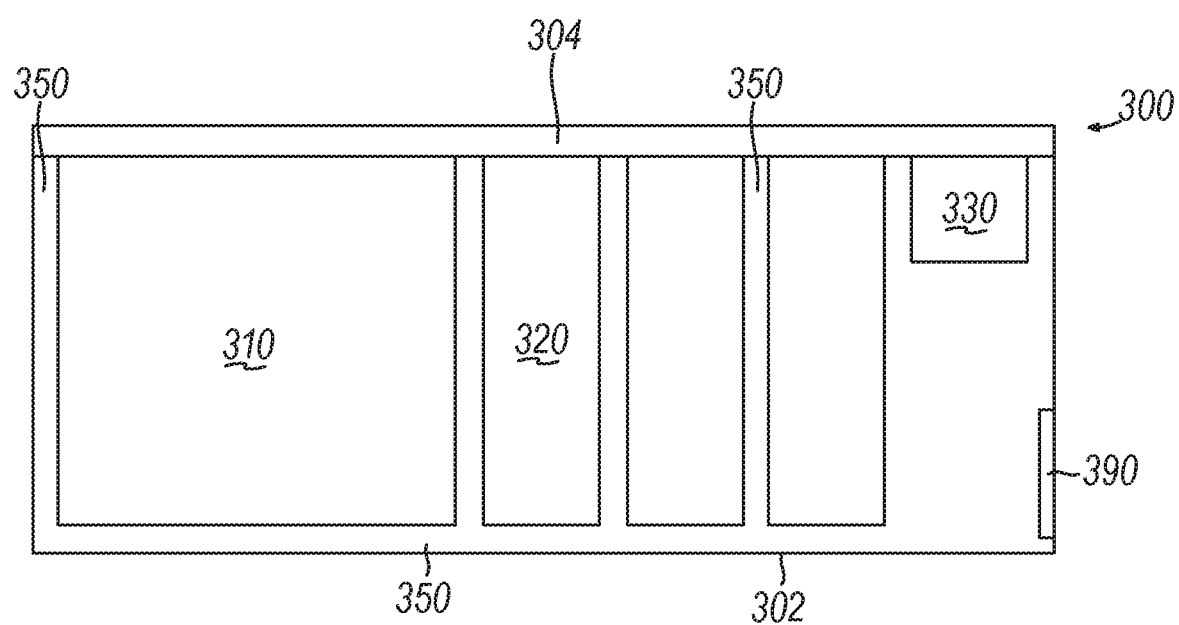
FIG. 2 depicts a block schematic cross-sectional view of an example of a consumable cartridge that may be utilized with the system of FIG. 1.

FIG. 2 depicts an implementation of a consumable cartridge 300. The consumable cartridge may be part of a combined removable cartridge, such as consumable reagent portion 210 of removable cartridge 200 of FIG. 1; or may be a separate reagent cartridge. The consumable cartridge 300 may include a housing 302 and a top 304. The housing 302 may comprise a non-conductive polymer or other material and be formed to make one or more reagent chambers 310, 320, 330. The reagent chambers 310, 320, 330 may be varying in size to accommodate varying volumes of reagents to be stored therein. For instance, a first chamber 310 may be larger than a second chamber 320, and the second chamber 320 may be larger than a third chamber 330. The first chamber 310 is sized to accommodate a larger volume of a particular reagent, such as a buffer reagent. The second chamber 320 may be sized to accommodate a smaller volume of reagent than the first chamber 310, such as a reagent chamber holding a cleaving reagent. The third chamber 330 may be sized to accommodate an even smaller volume of reagent than the first chamber 310 and the second chamber 320, such as a reagent chamber holding a fully functional nucleotide containing reagent.

In the illustrated implementation, the housing 302 has a plurality of housing walls or sides 350 forming the chambers 310, 320, 330 therein. In the illustrated implementation, the housing 302 forms a structure that is at least substantially unitary or monolithic. In alternative implementations, the housing 302 may be constructed by one or more sub-components that are combined to form the housing 302, such as independently formed compartments for chambers 310, 320, and 330.

The housing 302 may be sealed by the top 304 once reagents are provided into the respective chambers 310, 320, 330. The top 304 may comprise a conductive or non-conductive material. For instance, the top 304 may be an aluminum foil seal that is adhesively coupled to top surfaces of the housing 302 to seal the reagents within their respective chambers 310, 320, 330. In other implementations, the top 304 may be a plastic seal that is adhesively coupled to top surfaces of the housing 302 to seal the reagents within their respective chambers 310, 320, 330.

In some implementations, the housing 302 may also include an identifier 390. The identifier 390 may be a radio-frequency identification (RFID) transponder, a barcode, an identification chip, and/or other identifier. In some implementations, the identifier 390 may be embedded in the housing 302 or attached to an exterior surface. The identifier 390 may include data for a unique identifier for the consumable cartridge 300 and/or data for a type of the consumable cartridge 300. The data of the identifier 390 may be read by the base instrument 102 or a separate device configured for warming the consumable cartridge 300, as described herein.

In some implementations, the consumable cartridge 300 may include other components, such as valves, pumps, fluidic lines, ports, etc. In some implementations, the consumable cartridge 300 may be contained within a further exterior housing.

III. System Controller

The base instrument 102 may also include a system controller 120 that is configured to control operation of at least one of the removable cartridge 200 and/or the detection assembly 110. The system controller 120 may be implemented utilizing any combination of dedicated hardware circuitry, boards, DSPs, processors, etc. Alternatively, the system controller 120 may be implemented utilizing an off-the-shelf PC with a single processor or multiple processors, with the functional operations distributed between the processors. As a further option, the system controller 120 may be implemented utilizing a hybrid configuration in which certain modular functions are performed utilizing dedicated hardware, while the remaining modular functions are performed utilizing an off-the-shelf PC and the like.

The system controller 120 may include a plurality of circuitry modules that are configured to control operation of certain components of the base instrument 102 and/or the removable cartridge 200. The term "module" herein may refer to a hardware device configured to perform specific task(s). For instance, the circuitry modules may include a flow-control module that is configured to control flow of fluids through the fluidic network of the removable cartridge 200. The flow-control module may be operably coupled to valve actuators and/or s system pump. The flow-control module may selectively activate the valve actuators and/or the system pump to induce flow of fluid through one or more paths and/or to block flow of fluid through one or more paths.

The system controller 120 may also include a thermal-control module. The thermal-control module may control a thermocycler or other thermal component to provide and/or remove thermal energy from a sample-preparation region of the removable cartridge 200 and/or any other region of the removeable cartridge 200. In one particular example, a thermocycler may increase and/or decrease a temperature that is experienced by the biological material in accordance with a PCR protocol.

The system controller 120 may also include a detection module that is configured to control the detection assembly 110 to obtain data regarding the biological material. The detection module may control operation of the detection assembly 110 either through a direct wired connection or through the contact array if the detection assembly 110 is part of the removable cartridge 200. The detection module may control the detection assembly 110 to obtain data at predetermined times or for predetermined time periods. By way of example, the detection module may control the detection assembly 110 to capture an image of a reaction chamber of the flow cell receiving portion 220 of the removable cartridge when the biological material has a fluorophore attached thereto. In some implementations, a plurality of images may be obtained.

Optionally, the system controller 120 may include an analysis module that is configured to analyze the data to provide at least partial results to a user of the system 100. For example, the analysis module may analyze the imaging data provided by the detection assembly 110. The analysis may include identifying a sequence of nucleic acids of the biological material.

The system controller 120 and/or the circuitry modules described above may include one or more logic-based devices, including one or more microcontrollers, processors, reduced instruction set computers (RISC), application specific integrated circuits (ASICs), field programmable gate array (FPGAs), logic circuits, and any other circuitry capable of executing functions described herein. In an implementation, the system controller 120 and/or the circuitry modules execute a set of instructions that are stored in a computer- or machine-readable medium therein in order to perform one or more assay protocols and/or other operations. The set of instructions may be stored in the form of information sources or physical memory elements within the base instrument 102 and/or the removable cartridge 200. The protocols performed by the system 100 may be used to carry out, for example, machine-writing DNA or otherwise synthesizing DNA (e.g., converting binary data into a DNA sequence and then synthesizing DNA strands or other polynucleotides representing the binary data), quantitative analysis of DNA or RNA, protein analysis, DNA sequencing (e.g., sequencing-by-synthesis (SBS)), sample preparation, and/or preparation of fragment libraries for sequencing.

The set of instructions may include various commands that instruct the system 100 to perform specific operations such as the methods and processes of the various implementations described herein. The set of instructions may be in the form of a software program. As used herein, the terms "software" and "firmware" are interchangeable and include any computer program stored in memory for execution by a computer, including RAM memory, ROM memory, EPROM memory, EEPROM memory, and non-volatile RAM (NVRAM) memory. The above memory types are only examples and are thus not limiting as to the types of memory usable for storage of a computer program.

The software may be in various forms such as system software or application software. Further, the software may be in the form of a collection of separate programs, or a program module within a larger program or a portion of a program module. The software also may include modular programming in the form of object-oriented programming. After obtaining the detection data, the detection data may be automatically processed by the system 100, processed in response to user inputs, or processed in response to a request made by another processing machine (e.g., a remote request through a communication link).

The system controller 120 may be connected to the other components or sub-systems of the system 100 via communication links, which may be hardwired or wireless. The system controller 120 may also be communicatively connected to off-site systems or servers. The system controller 120 may receive user inputs or commands, from a user interface 130. The user interface 130 may include a keyboard, mouse, a touch-screen panel, and/or a voice recognition system, and the like.

The system controller 120 may serve to provide processing capabilities, such as storing, interpreting, and/or executing software instructions, as well as controlling the overall operation of the system 100. The system controller 120 may be configured and programmed to control data and/or power aspects of the various components. Although the system controller 120 is represented as a single structure in FIG. 1, it is understood that the system controller 120 may include multiple separate components (e.g., processors) that are distributed throughout the system 100 at different locations. In some implementations, one or more components may be integrated with the base instrument 102 and one or more components may be located remotely with respect to the base instrument 102.

IV. Flow Cell

Figure 3:
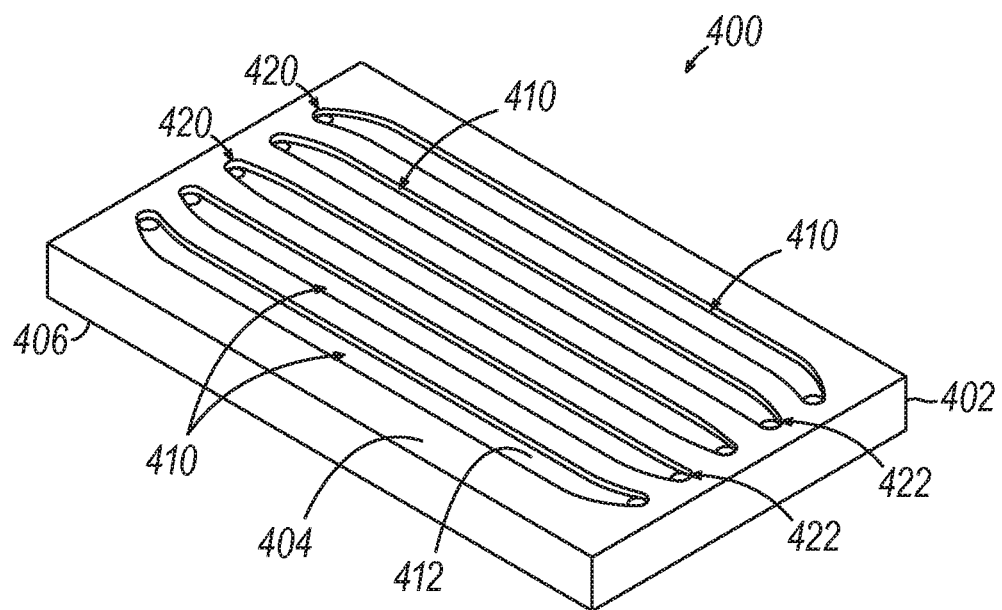
FIG. 3 depicts a perspective view of an example of a flow cell that may be utilized with the system of FIG. 1.
Figure 4:
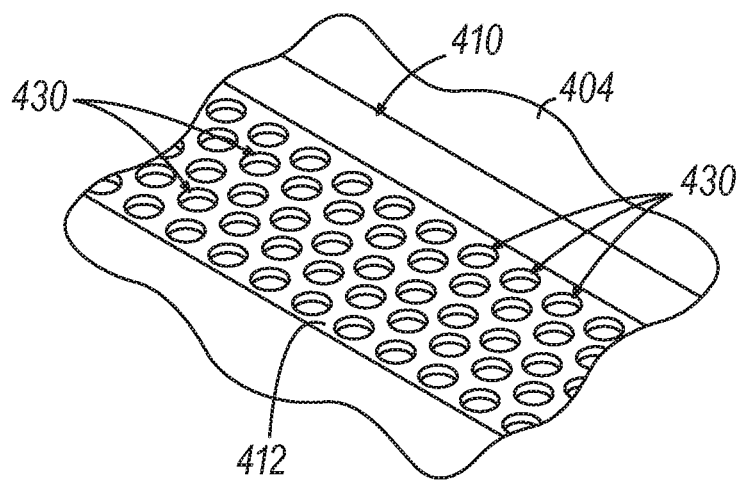
FIG. 4 depicts an enlarged perspective view of a channel of the flow cell of FIG. 3.

FIGS. 3-4 depict an example of a flow cell 400 that may be used with system 100. Flow cell of this example includes a body defining a plurality of elongate flow channels 410, which are recessed below an upper surface 404 of the body 402. The flow channels 410 are generally parallel with each other and extend along substantially the entire length of body 402. While five flow channels 410 are shown, a flow cell 400 may include any other suitable number of flow channels 410, including more or fewer than five flow channels 410. The flow cell 400 of this example also includes a set of inlet ports 420 and a set of outlet ports 422, with each port 420, 422 being associated with a corresponding flow channel 410. Thus, each inlet port 420 may be utilized to communicate fluids (e.g., reagents, etc.) to the corresponding channel 410; while each outlet port 422 may be utilized to communicate fluids from the corresponding flow channel 410.

In some versions, the flow cell 400 is directly integrated into the flow cell receiving portion 220 of the removable cartridge 200. In some other versions, the flow cell 400 is removably coupled with the flow cell receiving portion 220 of the removable cartridge 200. In versions where the flow cell 400 is either directly integrated into the flow cell receiving portion 220 or removably coupled with the flow cell receiving portion 220, the flow channels 410 of the flow cell 400 may receive fluids from the consumable reagent portion 210 via the inlet ports 420, which may be fluidly coupled with reagents stored in the consumable reagent portion 210. Of course, the flow channels 410 may be coupled with various other fluid sources or reservoirs, etc., via the ports 420, 422. As another illustrative variation, some versions of consumable cartridge 300 may be configured to removably receive or otherwise integrate the flow cell 400. In such versions, the flow channels 410 of the flow cell 400 may receive fluids from the reagent chambers 310, 320, 330 via the inlet ports 420. Other suitable ways in which the flow cell 400 may be incorporated into the system 100 will be apparent to those skilled in the art in view of the teachings herein.

FIG. 4 shows a flow channel 410 of the flow cell 400 in greater detail. As shown, the flow channel 410 includes a plurality of wells 430 formed in a base surface 412 of the flow channel 410. As will be described in greater detail below each well 430 is configured to contain DNA strands or other polynucleotides, such as machine-written polynucleotides. In some versions, each well 430 has a cylindraceous configuration, with a generally circular cross-sectional profile. In some other versions, each well 430 has a polygonal (e.g., hexagonal, octagonal, etc.) cross-sectional profile. Alternatively, wells 430 may have any other suitable configuration. It should also be understood that wells 430 may be arranged in any suitable pattern, including but not limited to a grid pattern.

Figure 5:
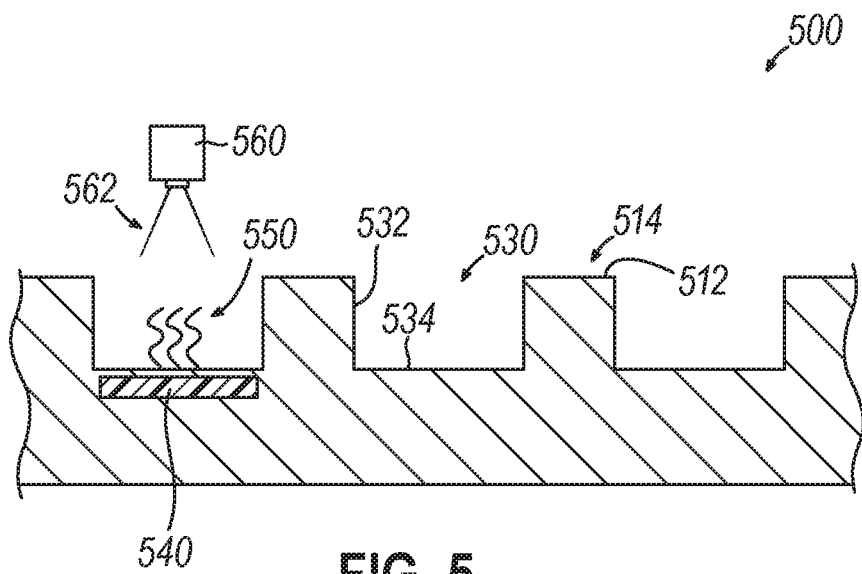
FIG. 5 depicts a block schematic cross-sectional view of an example of wells that may be incorporated into the channel of FIG. 4.

FIG. 5 shows a portion of a channel within a flow cell 500 that is an example of a variation of the flow cell 400. In other words, the channel depicted in FIG. 5 is a variation of the flow channel 410 of the flow cell 400. This flow cell 500 is operable to read polynucleotide strands 550 that are secured to the floor 534 of wells 530 in the flow cell 500. By way of example only, the floor 534 where polynucleotide strands 550 are secured may include a co-block polymer capped with azido. By way of further example only, such a polymer may comprise a poly(N-(5-azidoacetamidylpentyl)acrylamide-co-acrylamide) (PAZAM) coating provided in accordance with at least some of the teachings of U.S. Pat. No. 9,012,022, entitled "Polymer Coatings," issued Apr. 21, 2015, which is incorporated by reference herein in its entirety. Such a polymer may be incorporated into any of the various flow cells described herein.

In the present example, the wells 530 are separated by interstitial spaces 514 provided by the base surface 512 of the flow cell 500. Each well 530 has a sidewall 532 and a floor 534. The flow cell 500 in this example is operable to provide an image sensor 540 under each well 530. In some versions, each well 530 has at least one corresponding image sensor 540, with the image sensors 540 being fixed in position relative to the wells 530. Each image sensor 540 may comprise a CMOS image sensor, a CCD image sensor, or any other suitable kind of image sensor. By way of example only, each well 530 may have one associated image sensor 540 or a plurality of associated image sensors 540. As another variation, a single image sensor 540 may be associated with two or more wells 530. In some versions, one or more image sensors 540 move relative to the wells 530, such that a single image sensor 540 or single group of image sensors 540 may be moved relative to the wells 530. As yet another variation, the flow cell 500 may be movable in relation to the single image sensor 540 or single group of image sensors 540, which may be at least substantially fixed in position.

Each image sensor 540 may be directly incorporated into the flow cell 500. Alternatively, each image sensor 540 may be directly incorporated into a cartridge such as the removable cartridge 200, with the flow cell 500 being integrated into or otherwise coupled with the cartridge. As yet another illustrative variation, each image sensor 540 may be directly incorporated into the base instrument 102 (e.g., as part of the detection assembly 110 noted above). Regardless of where the image sensor(s) 540 is/are located, the image sensor(s) 540 may be integrated into a printed circuit that includes other components (e.g., control circuitry, etc.). In versions where the one or more image sensors 540 are not directly incorporated into the flow cell 500, the flow cell 500 may include optically transmissive features (e.g., windows, etc.) that allow the one or more image sensors 540 to capture fluorescence emitted by the one or more fluorophores associated with the polynucleotide strands 550 that are secured to the floors 534 of the wells 530 in the flow cell 500 as described in greater detail below. It should also be understood that various kinds of optical elements (e.g., lenses, optical waveguides, etc.) may be interposed between the floors 534 of the wells 530 and the corresponding image sensor(s) 540.

As also shown in FIG. 5, a light source 560 is operable to project light 562 into the well 530. In some versions, each well 530 has at least one corresponding light source 560, with the light sources 560 being fixed in position relative to the wells 530. By way of example only, each well 530 may have one associated light source 560 or a plurality of associated light sources 560. As another variation, a single light source 560 may be associated with two or more wells 530. In some other versions, one or more light sources 560 move relative to the wells 530, such that a single light source 560 or single group of light sources 560 may be moved relative to the wells 530. As yet another variation, the flow cell 500 may be movable in relation to the single light source 560 or single group of light sources 560, which may be substantially fixed in position. By way of example only, each light source 560 may include one or more lasers. In another example, the light source 560 may include one or more diodes.

Each light source 560 may be directly incorporated into the flow cell 500. Alternatively, each light source 560 may be directly incorporated into a cartridge such as the removable cartridge 200, with the flow cell 500 being integrated into or otherwise coupled with the cartridge. As yet another illustrative variation, each light source 560 may be directly incorporated into the base instrument 102 (e.g., as part of the detection assembly 110 noted above). In versions where the one or more light sources 560 are not directly incorporated into the flow cell 500, the flow cell 500 may include optically transmissive features (e.g., windows, etc.) that allow the wells 530 to receive the light emitted by the one or more light source 560, to thereby enable the light to reach the polynucleotide strands 550 that are secured to the floor 534 of the wells 530. It should also be understood that various kinds of optical elements (e.g., lenses, optical waveguides, etc.) may be interposed between the wells 530 and the corresponding light source(s) 560.

Figure 6:
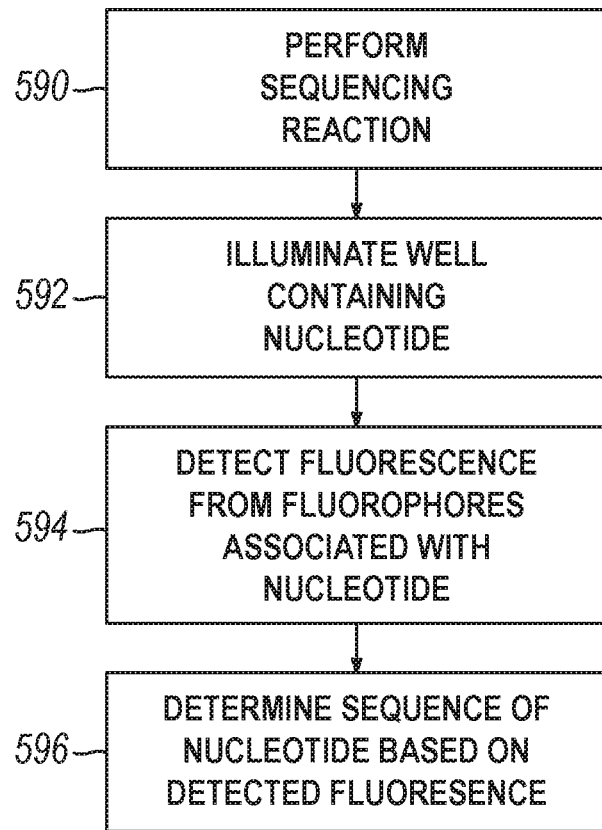
FIG. 6 depicts a flow chart of an example of a process for reading polynucleotides.

As described elsewhere herein and as is shown in block 590 of FIG. 6, a DNA reading process may begin with performing a sequencing reaction in the targeted well(s) 530 (e.g., in accordance with at least some of the teachings of U.S. Pat. No. 9,453,258, entitled "Methods and Compositions for Nucleic Acid Sequencing," issued Sep. 27, 2016, which is incorporated by reference herein in its entirety). Next, as shown in block 592 of FIG. 6, the light source(s) 560 is/are activated over the targeted well(s) 530 to thereby illuminate the targeted well(s) 530. The projected light 562 may cause a fluorophore associated with the polynucleotide strands 550 to fluoresce. Accordingly, as shown in block 594 of FIG. 6, the corresponding image sensor(s) 540 may detect the fluorescence emitted from the one or more fluorophores associated with the polynucleotide strands 550. The system controller 120 of the base instrument 102 may drive the light source(s) 560 to emit the light. The system controller 120 of the base instrument 102 may also process the image data obtained from the image sensor(s) 540, representing the fluorescent emission profiles from the polynucleotide strands 550 in the wells 530. Using this image data from the image sensor(s) 540, and as shown in block 596 of FIG. 6, the system controller 120 may determine the sequence of bases in each polynucleotide strand 550. By way of example only, this process and equipment may be utilized to map a genome or otherwise determine biological information associated with a naturally occurring organism, where DNA strands or other polynucleotides are obtained from or otherwise based on a naturally occurring organism. Alternatively, the above-described process and equipment may be utilized to obtain data stored in machine-written DNA as will be described in greater detail below.

By way of further example only, when carrying out the above-described procedure shown in FIG. 6, time space sequencing reactions may utilize one or more chemistries and imaging events or steps to differentiate between a plurality of analytes (e.g., four nucleotides) that are incorporated into a growing nucleic acid strand during a sequencing reaction; or alternatively, fewer than four different colors may be detected in a mixture having four different nucleotides while still resulting in the determination of the four different nucleotides (e.g., in a sequencing reaction). A pair of nucleotide types may be detected at the same wavelength, but distinguished based on a difference in intensity for one member of the pair compared to the other, or based on a change to one member of the pair (e.g., via chemical modification, photochemical modification, or physical modification) that causes apparent signal to appear or disappear compared to the signal detected for the other member of the pair.

V. Machine-Writing Biological Material

In some implementations, a system 100 such as the system 100 shown in FIG. 1 may be configured to synthesize biological materials (e.g. polynucleotide, such as DNA) to encode data that may later be retrieved through the performance of assays such as those described above. In some implementations, this type of encoding may be performed by assigning values to nucleotide bases (e.g., binary values, such as 0 or 1, ternary values such as 0, 1 or 2, etc.), converting the data to be encoded into a string of the relevant values (e.g., converting a textual message into a binary string using the ASCII encoding scheme), and then creating one or more polynucleotides made up of nucleotides having bases in a sequence corresponding to the string obtained by converting the data.

Figure 7:
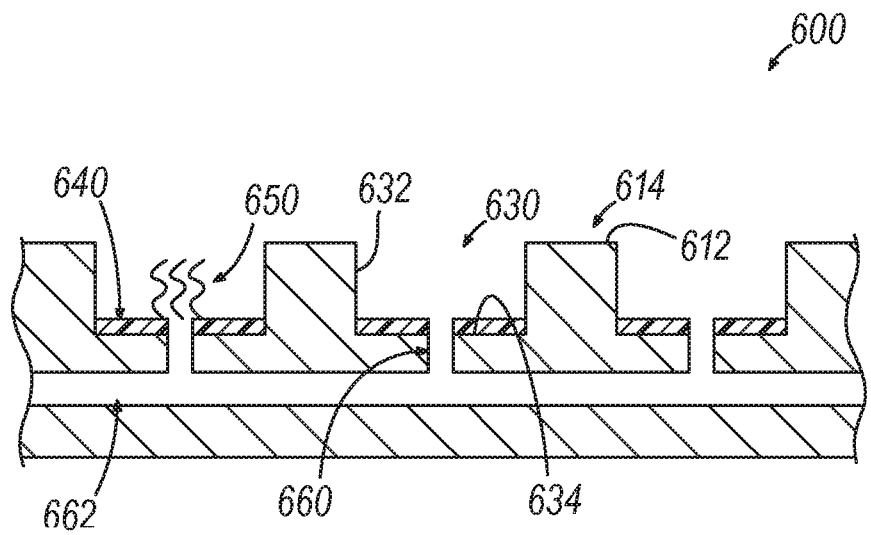
FIG. 7 depicts a block schematic cross-sectional view of another example of wells that may be incorporated into the channel of FIG. 4.

In some implementations, the creation of such polynucleotides may be performed using a version of the flow cell 400 having an array of wells 630 that are configured as shown in FIG. 7. FIG. 7 shows a portion of a channel within a flow cell 600 that is an example of a variation of the flow cell 400. In other words, the channel depicted in FIG. 7 is a variation of the flow channel 410 of the flow cell 400. In this example, each well 630 is recessed below a base surface 612 of the flow cell 600. The wells 630 are thus spaced apart from each other by interstitial spaces 614. By way of example only, the wells 630 may be arranged in a grid or any other suitable pattern along the base surface 612 of the flow cell 600. Each well 630 of this example includes a sidewall 632 and a floor 634. Each well 630 of this example further includes a respective electrode assembly 640 positioned on the floor 634 of the well 630. In some versions, each electrode assembly 640 includes just a single electrode element. In some other versions, each electrode assembly 640 includes a plurality of electrode elements or segments. The terms "electrode" and "electrode assembly" should be read herein as being interchangeable.

Base instrument 102 is operable to independently activate electrode assemblies 640, such that one or more electrode assemblies 640 may be in an activated state while one or more other electrode assemblies 640 are not in an activated state. In some versions, a CMOS device or other device is used to control electrode assemblies 640. Such a CMOS device may be integrated directly into the flow cell 600, may be integrated into a cartridge (e.g., cartridge 200) in which the flow cell 600 is incorporated, or may be integrated directly into the base instrument 102. As shown in FIG. 7, each electrode assembly 640 extends along the full width of floor 634, terminating at the sidewall 632 of the corresponding well 630. In other versions, each electrode assembly 640 may extend along only a portion of the floor 634. For instance, some versions of electrode assembly 640 may terminate interiorly relative to the sidewall 632. While each electrode assembly 540 is schematically depicted as a single element in FIG. 5, it should be understood that each electrode assembly 540 may in fact be formed by a plurality of discrete electrodes rather than just consisting of one single electrode.

As shown in FIG. 7, specific polynucleotide strands 650 may be created in individual wells 630 by activating the electrode assembly 640 of the relevant wells 630 to electrochemically generate acid that may deprotect the end group of the polynucleotide strand 650 in the well 630. By way of example only, polynucleotide strands 650 may be chemically attached to the surface at the bottom of the well 630 using linkers having chemistries such as silane chemistry on one end and DNA synthesis compatible chemistry (e.g., a short oligo for enzyme to bind to) on the other end.

To facilitate reagent exchange (e.g., transmission of a deblocking agent), each electrode assembly 640 and the floor 634 of each well 630 may include at least one opening 660 in this example. The openings 660 may be fluidly coupled with a flow channel 662 that extends underneath the wells 630, below the floors 634. To provide such an opening 660 through the electrode assembly 640, the electrode assembly 640 may be annular in shape, may be placed in quadrants, may be placed on the perimeter or sidewall 632 of the well 630, or may be placed or shaped in other suitable manners to avoid interference with reagent exchange and/or passage of light (e.g., as may be used in a sequencing process that involved detection of fluorescent emissions). In other implementations, reagents may be provided into the flow channel of the flow cell 600 without the openings 660.

It should be understood that the openings 660 may be optional and may be omitted in some versions. Similarly, the flow channel 662 may be optional and may be omitted in some versions.

Figure 9:
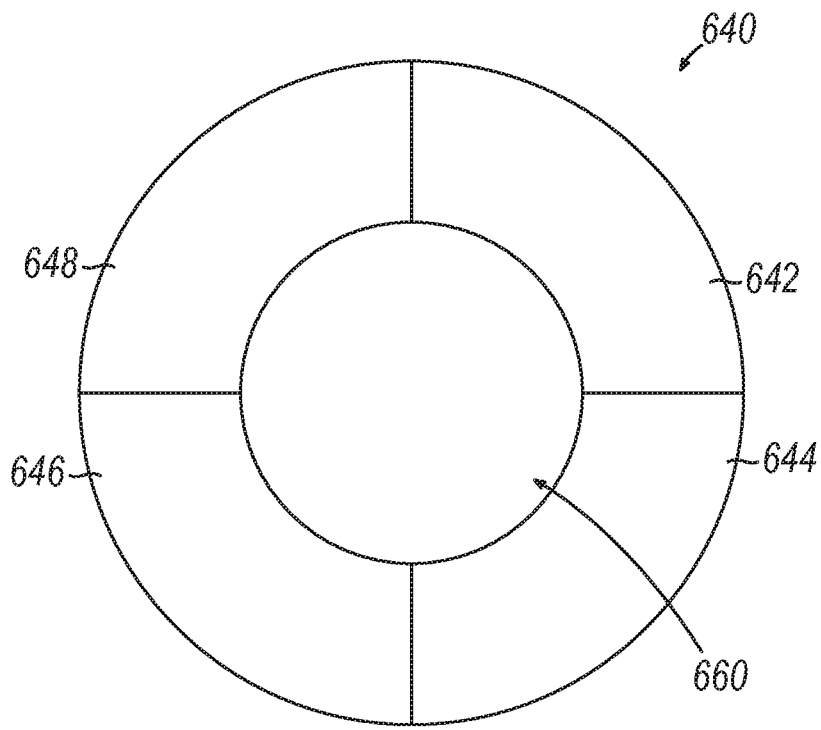
FIG. 9 depicts a top plan view of an example of an electrode assembly.

FIG. 9 shows an example of a form that electrode assembly 640 may take. In this example, electrode assembly 640 includes four discrete electrode segments 642, 644, 646, 648 that together define an annular shape. The electrode segments 642, 644, 646, 648 are thus configured as discrete yet adjacent quadrants of a ring. Each electrode segment 642, 644, 646, 648 may be configured to provide a predetermined charge that is uniquely associated with a particular nucleotide. For instance, electrode segment 642 may be configured to provide a charge that is uniquely associated with adenine; electrode segment 644 may be configured to provide a charge that is uniquely associated with cytosine; electrode segment 646 may be configured to provide a charge that is uniquely associated with guanine; and electrode segment 648 may be configured to provide a charge that is uniquely associated with thymine. When a mixture of those four nucleotides are flowed through the flow channel above the wells 630, activation of electrode segments 642, 644, 646, 648 may cause the corresponding nucleotides from that flow to adhere to the strand 650. Thus, when electrode segment 642 is activated, it may effect writing of adenine to the strand 650; when electrode segment 644 is activated, it may effect writing of cytosine to the strand 650; when electrode segment 646 is activated, it may effect writing of guanine to the strand 650; and when electrode segment 648 is activated, it may effect writing of thymine to the strand 650. This writing may be provided by the activated electrode segment 642, 644, 646, 648 hybridizing the inhibitor of the enzyme for the pixel associated with the activated electrode segment 642, 644, 646, 648. While electrode segments 642, 644, 646, 648 are shown as forming an annular shape in FIG. 9, it should be understood that any other suitable shape or shapes may be formed by electrode segments 642, 644, 646, 648. In still other implementations, a single electrode may be utilized for the electrode assembly 640 and the charge may be modulated to incorporate various nucleotides to be written to the DNA strand or other polynucleotide.

As another example, the electrode assembly 640 may be activated to provide a localized (e.g., localized within the well 630 in which the electrode assembly 640 is disposed), electrochemically generated change in pH; and/or electrochemically generate a moiety (e.g., a reducing or oxidizing reagent) locally to remove a block from a nucleotide. As yet another variation, different nucleotides may have different blocks; and those blocks may be photocleaved based on a wavelength of light communicated to the well 630 (e.g., light 562 projected from the light source 560). As still another variation, different nucleotides may have different blocks; and those blocks may be cleaved based on certain other conditions. For instance, one of the four blocks may be removed based on a combination of a reducing condition plus either high local pH or low local pH; another of the four blocks may be removed based on a combination of an oxidative condition plus either high local pH or low local pH; another of the four blocks may be removed based on a combination of light and a high local pH; and another of the four blocks may be removed based on a combination of light and a low local pH. Thus, four nucleotides may be incorporated at the same time, but with selective unblocking occurring in response to four different sets of conditions.

The electrode assembly 640 further defines the opening 660 at the center of the arrangement of the electrode segments 642, 644, 646, 648. As noted above, this opening 660 may provide a path for fluid communication between the flow channel 662 and the wells 630, thereby allowing reagents, etc. that are flowed through the flow channel 662 to reach the wells 630. As also noted above, some variations may omit the flow channel 662 and provide communication of reagents, etc. to the wells 630 in some other fashion (e.g., through passive diffusion, etc.). Regardless of whether fluid is communicated through the opening 660, the opening 660 may provide a path for optical transmission through the bottom of the well 630 during a read cycle, as described herein. In some versions, the opening 660 may be optional and may thus be omitted. In versions where the opening 660 is omitted, fluids may be communicated to the wells 630 via one or more flow channels that are above the wells 630 or otherwise positioned in relation to the wells 630. Moreover, the opening 660 may not be needed for providing a path for optical transmission through the bottom of the well 630 during a read cycle. For instance, as described below in relation to the flow cell 601, the electrode assembly 640 may comprise an optically transparent material (e.g., optically transparent conducting film (TCF), etc.), and the flow cell 600 itself may comprise an optically transparent material (e.g., glass), such that the electrode assembly 640 and the material forming the flow cell 600 may allow the fluorescence emitted from the one or more fluorophores associated with the machine-written polynucleotide strands 650 to reach an image sensor 540 that is under the well 630.

Figure 8:
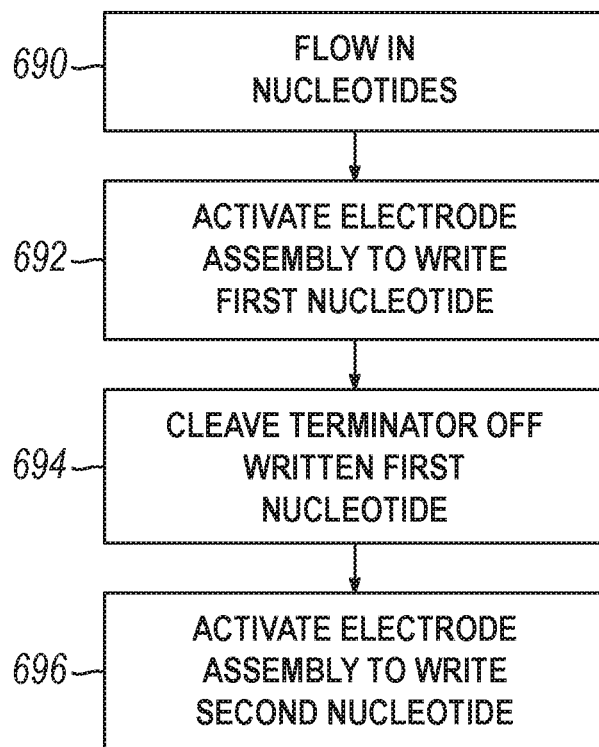
FIG. 8 depicts a flow chart of an example of a process for writing polynucleotides.

FIG. 8 shows an example of a process that may be utilized in the flow cell 600 to machine-write polynucleotides or other nucleotide sequences. At the beginning of the process, as shown in the first block 690 of FIG. 8, nucleotides may be flowed into the flow cell 600, over the wells 630. As shown in the next block 692 in FIG. 8, the electrode assembly 640 may then be activated to write a first nucleotide to a primer at the bottom of a targeted well 630. As shown in the next block 694 of FIG. 8, a terminator may then be cleaved off the first nucleotide that was just written in the targeted well 630. Various suitable ways in which a terminator may be cleaved off the first nucleotide will be apparent to those skilled in the art in view of the teachings herein. Once the terminator is cleaved off the first nucleotide, as shown in the next block 696 of FIG. 8, the electrode assembly 640 may be activated to write a second nucleotide to the first nucleotide. While not shown in FIG. 8, a terminator may be cleaved off the second nucleotide, then a third nucleotide may be written to the second nucleotide, and so on until the desired sequence of nucleotides has been written.

In some implementations, encoding of data via synthesis of biological materials such as DNA may be performed in other manners. For example, in some implementations, the flow cell 600 may lack the electrode assembly 640 altogether. For instance, deblock reagents may be selectively communicated from the flow channel 662 to the wells 630 through the openings 660. This may eliminate the need for electrode assemblies 640 to selectively activate nucleotides. As another example, an array of wells 630 may be exposed to a solution containing all nucleotide bases that may be used in encoding the data, and then individual nucleotides may be selectively activated for individual wells 630 by using light from a spatial light modulator (SLM). As another example, in some implementations individual bases may be assigned combined values (e.g., adenine may be used to encode the binary couplet 00, guanine may be used to encode the binary couplet 01, cytosine may be used to encode the binary couplet 10, and thymine may be used to encode the binary couplet 11) to increase the storage density of the polynucleotides being created. Other examples are also possible and will be immediately apparent to those skilled in the art in light of this disclosure. Accordingly, the above description of synthesizing biological materials such as DNA to encode data should be understood as being illustrative only; and should not be treated as limiting.

VI. Reading Machine-Written Biological Material

After polynucleotide strands 650 have been machine-written in one or more wells 630 of a flow cell 600, the polynucleotide strands 650 may be subsequently read to extract whatever data or other information was stored in the machine-written polynucleotide strands 650. Such a reading process may be carried out using an arrangement such as that shown in FIG. 5 and described above. In other words, one or more light sources 560 may be used to illuminate one or more fluorophores associated with the machine-written polynucleotide strands 650; and one or more image sensors 540 may be used to detect the fluorescent light emitted by the illuminated one or more fluorophores associated with the machine-written polynucleotide strands 650. The fluorescence profile of the light emitted by the illuminated one or more fluorophores associated with the machine-written polynucleotide strands 650 may be processed to determine the sequence of bases in the machine-written polynucleotide strands 650. This determined sequence of bases in the machine-written polynucleotide strands 650 may be processed to determine the data or other information that was stored in the machine-written polynucleotide strands 650.

In some versions, the machine-written polynucleotide strands 650 remain in the flow cell 600 containing wells 630 for a storage period. When it is desired to read the machine-written polynucleotide strands 650, the flow cell 600 may permit the machine-written polynucleotide strands 650 to be read directly from the flow cell. By way of example only, the flow cell 600 containing wells 630 may be received in a cartridge (e.g., cartridge 200) or base instrument 102 containing light sources 560 and/or image sensors 540, such that the machine-written polynucleotide strands 650 are read directly from the wells 630.

Figure 10:
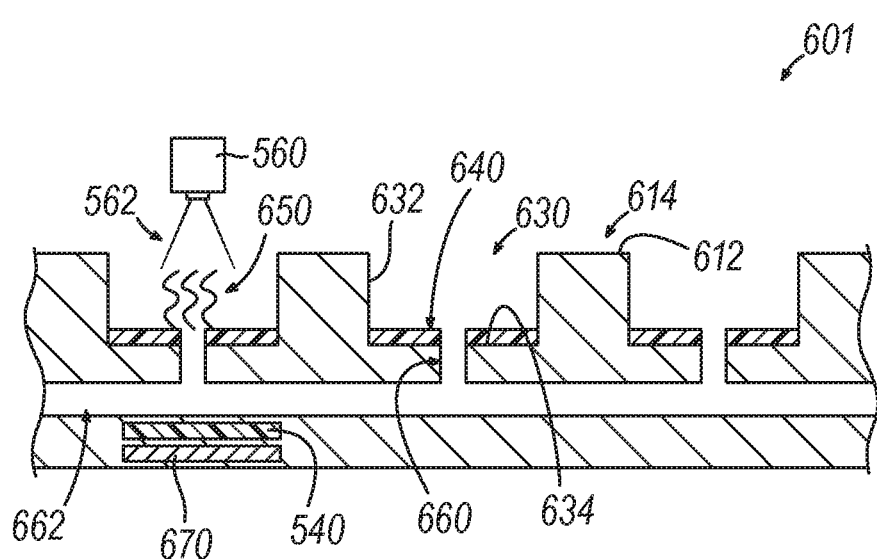
FIG. 10 depicts a block schematic cross-sectional view of another example of wells that may be incorporated into the channel of FIG. 4.

As another illustrative example, the flow cell containing wells 630 may directly incorporate one or both of light source(s) 560 or image sensor(s) 540. FIG. 10 shows an example of a flow cell 601 that includes wells 630 with electrode assemblies 640, one or more image sensors 540, and a control circuit 670. Like in the flow cell 500 depicted in FIG. 5, the flow cell 601 of this example is operable to receive light 562 projected from a light source 560. This projected light 562 may cause one or more fluorophores associated with the machine-written polynucleotide strands 650 to fluoresce; and the corresponding image sensor(s) 540 may capture the fluorescence emitted from the one or more fluorophores associated with the machine-written polynucleotide strands 650.

As noted above in the context of the flow cell 500, each well 650 of the flow cell 601 may include its own image sensor 540 and/or its own light source 560; or these components may be otherwise configured and arranged as described above. In the present example, the fluorescence emitted from the one or more fluorophores associated with the machine-written polynucleotide strands 650 may reach the image sensor 540 via the opening 660. In addition, or in the alternative, the electrode assembly 640 may comprise an optically transparent material (e.g., optically transparent conducting film (TCF), etc.), and the flow cell 601 itself may comprise an optically transparent material (e.g., glass), such that the electrode assembly 640 and the material forming the flow cell 601 may allow the fluorescence emitted from the one or more fluorophores associated with machine-written polynucleotide strands 650 to reach the image sensor 540. Moreover, various kinds of optical elements (e.g., lenses, optical waveguides, etc.) may be interposed between the wells 650 and the corresponding image sensor(s) to ensure that the image sensor 540 is only receiving fluorescence emitted from the one or more fluorophores associated with the machine-written polynucleotide strands 650 of the desired well(s) 630.

In the present example, the control circuit 670 is integrated directly into the flow cell 601. By way of example only, the control circuit 670 may comprise a CMOS chip and/or other printed circuit configurations/components. The control circuit 670 may be in communication with the image sensor(s) 540, the electrode assembly(ies) 640, and/or the light source 560. In this context, "in communication" means that the control circuit 670 is in electrical communication with image sensor(s) 540, the electrode assembly(ies) 640, and/or the light source 560. For instance, the control circuit 670 may be operable to receive and process signals from the image sensor(s) 540, with the signals representing images that are picked up by the image sensor(s) 540. "In communication" in this context may also include the control circuit 670 providing electrical power to the image sensor(s) 540, the electrode assembly(ies) 640, and/or the light source 560.

In some versions, each image sensor 540 has a corresponding control circuit 670. In some other versions, a control circuit 670 is coupled with several, if not all, of the image sensors in the flow cell 601. Various suitable components and configurations that may be used to achieve this will be apparent to those skilled in the art in view of the teachings herein. It should also be understood that the control circuit 670 may be integrated, in whole or in part, in a cartridge (e.g., removable cartridge 200) and/or in the base instrument 102, in addition to or in lieu of being integrated into the flow cell 601.

As still another illustrative example, regardless of whether a write-only flow cell like the flow cell 600 of FIG. 7 or a read-write flow cell like the flow cell 601 of FIG. 10 is used, the machine-written polynucleotide strands 650 may be transferred from wells 630 after being synthesized. This may occur shortly after the synthesis is complete, right before the machine-written polynucleotide strands 650 are to be read, or at any other suitable time. In such versions, the machine-written polynucleotide strands 650 may be transferred to a read-only flow cell like the flow cell 500 depicted in FIG. 5; and then be read in that read-only flow cell 500. Alternatively, any other suitable devices or processes may be used.

In some implementations, reading data encoded through the synthesis of biological materials may be achieved by determining the well(s) 630 storing the synthesized strand(s) 650 of interest and then sequencing those strands 650 using techniques such as those described previously (e.g., sequencing-by-synthesis). In some implementations, to facilitate reading data stored in nucleotide sequences, when data is stored, an index may be updated with information showing the well(s) 630 where the strand(s) 650 encoding that data was/were synthesized. For example, when an implementation of a system 100 configured to synthesize strands 650 capable of storing up to 256 bits of data is used to store a one megabit (1,048,576 bit) file, the system controller 120 may perform steps such as: 1) break the file into 4,096 256 bit segments; 2) identify a sequence of 4,096 wells 630 in the flow cell 600, 601 that were not currently being used to store data; 3) write the 4,096 segments to the 4,096 wells 430, 530; 4) update an index to indicate that the sequence starting with the first identified well 630 and ending at the last identified well 630 was being used to store the file. Subsequently, when a request to read the file was made, the index may be used to identify the well(s) 630 containing the relevant strand(s) 650, the strand(s) 650 from those wells 630 may be sequenced, and the sequences may be combined and converted into the appropriate encoding format (e.g., binary), and that combined and converted data may then be returned as a response to the read request.

In some implementations, reading of data previously encoded via synthesis of biological materials may be performed in other manners. For example, in some implementations, if a file corresponding to 4,096 wells 630 was to be written, rather than identifying 4,096 sequential wells 630 to write it to, a controller may identify 4,096 wells 630 and then update the index with multiple locations corresponding to the file in the event that those wells 630 did not form a continuous sequence. As another example, in some implementations, rather than identifying individual wells 630, a system controller 120 may group wells 630 together (e.g., into groups of 128 wells 630), thereby reducing the overhead associated with storing location data (i.e., by reducing the addressing requirements from one address per well 630 to one address per group of wells 630). As another example, in implementations that store data reflecting the location of wells 630 where DNA strands or other polynucleotides have been synthesized, that data may be stored in various ways, such as sequence identifiers (e.g., well 1, well 2, well 3, etc.) or coordinates (e.g., X and Y coordinates of a well's location in an array).

As another example, in some implementations, rather than reading strands 650 from the wells 630 in which they were synthesized, strands 650 may be read from other locations. For instance, strands 650 may be synthesized to include addresses, and then cleaved from the wells 630 and stored in a tube for later retrieval, during which the included address information may be used to identify the strands 650 corresponding to particular files. As another illustrative example, the strands 650 may be copied off the surface using polymerase and then eluted & stored in tube. Alternatively, the strands 650 may be copied on to a bead using biotinylated oligos hybridized to DNA strands or other polynucleotides and capturing extended products on streptavidin beads that are dispensed in the wells 630. Other examples are also possible and will be immediately apparent to those of skill in the art in light of this disclosure. Accordingly, the above description of retrieving data encoded through the synthesis of biological materials should be understood as being illustrative only; and should not be treated as limiting.

Implementations described herein may utilize a polymer coating for a surface of a flow cell, such as that described in U.S. Pat. No. 9,012,022, entitled "Polymer Coatings," issued Apr. 21, 2015, which is incorporated by reference herein in its entirety. Implementations described herein may utilize one or more labelled nucleotides having a detectable label and a cleavable linker, such as those described in U.S. Pat. No. 7,414,116, entitled "Labelled Nucleotide Strands," issued Aug. 19, 2008, which is incorporated by reference herein in its entirety. For instance, implementations described herein may utilize a cleavable linker that is cleavable with by contact with water-soluble phosphines or water-soluble transition metal-containing catalysts having a fluorophore as a detectable label. Implementations described herein may detect nucleotides of a polynucleotide using a two-channel detection method, such as that described in U.S. Pat. No. 9,453,258, entitled "Methods and Compositions for Nucleic Acid Sequencing," issued Sep. 27, 2016, which is incorporated by reference herein in its entirety. For instance, implementations described herein may utilize a fluorescent-based SBS method having a first nucleotide type detected in a first channel (e.g., dATP having a label that is detected in the first channel when excited by a first excitation wavelength), a second nucleotide type detected in a second channel (e.g., dCTP having a label that is detected in a second channel when excited by a second excitation wavelength), a third nucleotide type detected in both the first and second channel (e.g., dTTP having at least one label that is detected in both channels when excited by the first and/or second excitation wavelength), and a fourth nucleotide type that lacks a label that is not, or that is minimally, detected in either channel (e.g., dGTP having no label). Implementations of the cartridges and/or flow cells described herein may be constructed in accordance with one or more teachings described in U.S. Pat. No. 8,906,320, entitled "Biosensors for Biological or Chemical Analysis and Systems and Methods for Same," issued Dec. 9, 2014, which is incorporated by reference herein in its entirety; U.S. Pat. No. 9,512,422, entitled "Gel Patterned Surfaces," issued Dec. 6, 2016, which is incorporated by reference herein in its entirety; U.S. Pat. No. 10,254,225, entitled "Biosensors for Biological or Chemical Analysis and Methods of Manufacturing the Same," issued Apr. 9, 2019, which is incorporated by reference herein in its entirety; and/or U.S. Pub. No. 2018/0117587, entitled "Cartridge Assembly," published May 3, 2018, which is incorporated by reference herein in its entirety.

VII. Systems and Methods for Controlled Regions of Reading and Writing

One challenge associated with storage devices is allowing for simultaneous or near-simultaneous reading and writing of data, as some sequencing and synthesis operations with flow cells may require that the flow cell be conditioned and prepared (e.g., thermally conditioned to an appropriate temperature, chemically conditioned with proper reagents, etc.) for either writing of data, or reading of data, at a given time. For such conventional flow cells and systems, switching between a "write mode" and a "read mode" may require all operations to cease for a period of time while the wells are brought to a certain temperature, flushed of previously used reagents, receive new reagents, or receive other inputs. With such systems, it may not be possible to synthesize or write data to a first well of a flow cell, while also sequencing or reading data from a second well of the flow cell, as it may create a conflict of reagents or other conditioning inputs being provided to the flow cell.

Many modern data storage systems are assumed to have some capability to allow simultaneous reading and writing of data to a volume, both by users of such systems, and by other systems and devices that may communicate with such systems. Thus, an inability to simultaneously read and write data to a volume may be an inconvenience to users, such as where a user may like exchange information between volumes in a rack of storage devices so that one device may be removed and placed in storage (e.g., copying a first file from volume A to volume B, while also copying a second file from volume C to volume A), as it may create a scenario where the user is unable to remove the volume due to a number of queued actions that cannot be simultaneously performed. It may also be a technological problem for systems and devices in communication with the volume, as a software application may be programmed to constantly write data to a database or file system stored on a volume, while also regularly reading data from the same database or file system. Where such actions cannot be performed simultaneously, such a software application may encounter various unexpected behavior and errors, such as reduced hardware performance as local memories and caches are overwhelmed by queued operations, race conditions, or reduced software performance as needed inputs are not available at the time of an operation.

To address such issues, DNA storage devices and the associated systems and devices operable to read data, write data, or read and write data may implement one or more features such as selective activation of wells, simultaneous read-write caching, and multi volume management for simultaneous read-write operations using a DNA storage system. While examples described herein refer to a "DNA storage system," it should be understood that this is only one example of polynucleotide storage. The teachings herein may be readily applied to storage systems that utilize polynucleotides that are not necessarily in the form of DNA. The invention is thus not limited to using DNA as the only kind of polynucleotides for storage as described herein. Moreover, polynucleotides are only one example of biological material that may be used for storage as described herein.

A. Example DNA Storage System

When described herein, a system operable to read digital data encoded as DNA, or encode and write digital data to DNA, may be referred to as a system for DNA storage, or a DNA storage system. It should be understood that such a system may include various components and devices that may be assembled into a single piece of equipment (e.g., may be assembled and communicatively coupled within a case); or may be separate pieces of equipment that may be connected, arranged, or both in order to provide the described features.

Figure 21:
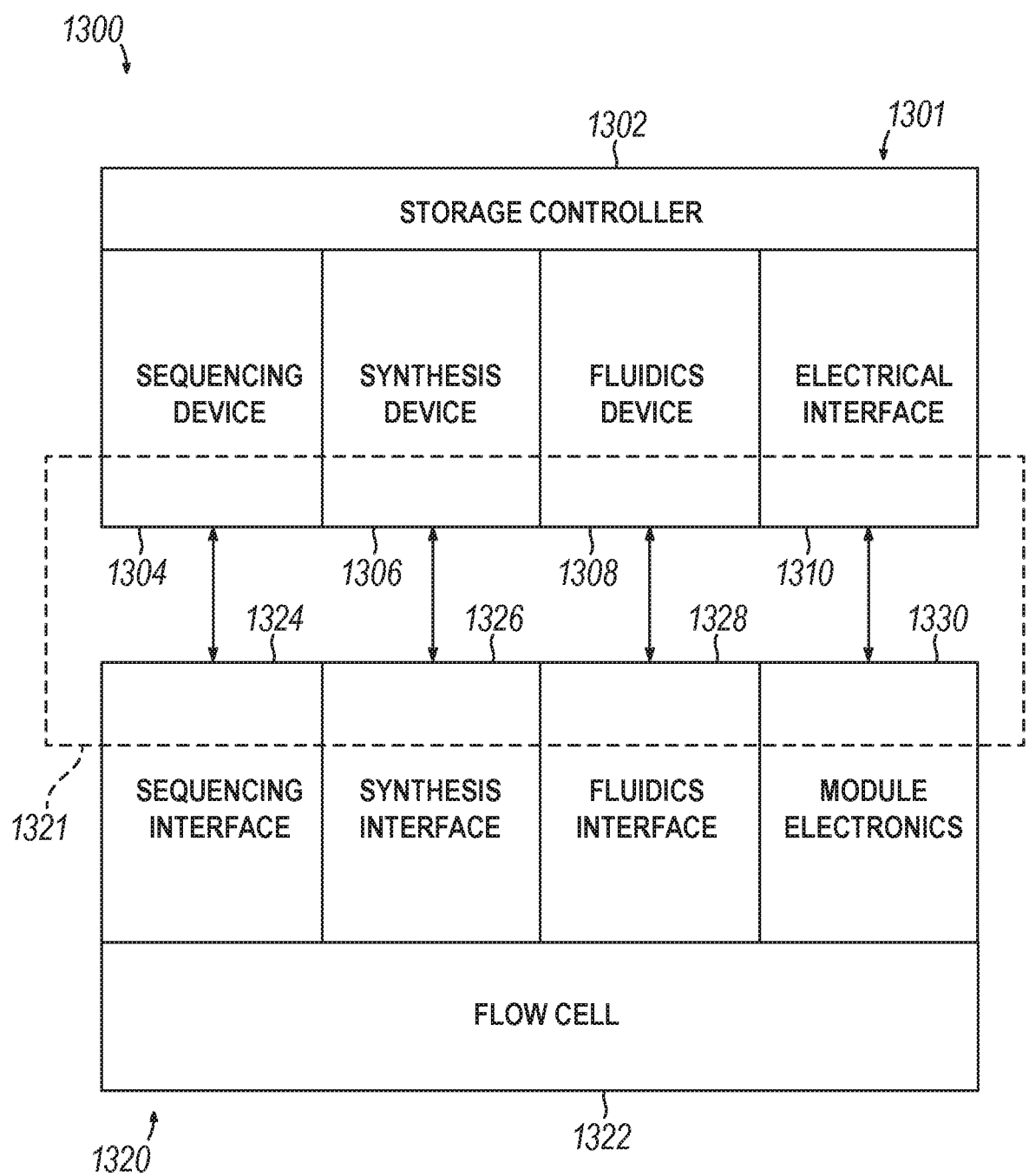
FIG. 21 depicts a schematic diagram of an example of a DNA storage system.

FIG. 21 shows a schematic diagram of an example of a DNA storage system 1300. The DNA storage system 1300 includes a set of instrumentation 1301 and a storage device 1320. The set of instrumentation 1301 may correspond to the base instrument 102 described above. The set of instrumentation 1301 may be assembled within a single piece of equipment, or may be one or more separate pieces of equipment arranged, connected, or both, in order to provide the described functionality. The set of instrumentation 1301 includes a storage controller 1302 that may be one or more processors and memories configured to store and execute instructions to operate the set of instrumentation 1301. The set of instrumentation 1301 also includes a sequencing device 1304, a synthesis device 1306, a fluidics device 1308, and an electrical interface 1310.

In some implementations, the storage controller 1302, the sequencing device 1304, the synthesis device 1306, the fluidics device 1308, and the electrical interface 1310 may be separate devices with one or more fluidic, electric, or mechanical interfaces therebetween. In other implementations, the storage controller 1302, the sequencing device 1304, the synthesis device 1306, the fluidics device 1308, and the electrical interface 1310 may be integrated into a single device with each of the sequencing device 1304, the synthesis device 1306, the fluidics device 1308, and the electrical interface 1310 forming a sub-component thereof.

The storage device 1320 may be permanently or removably coupled with the set of instrumentation 1301; and includes a flow cell 1322 having a plurality of wells. The storage device 1320 also includes a sequencing interface 1324, a synthesis interface 1326, a fluidics interface 1328, and a set of module electronics 1330. In some implementations, the flow cell 1322, the sequencing interface 1324, the synthesis interface 1326, the fluidics interface 1328, and the set of module electronics 1330 may be separate devices with one or more fluidic, electric, or mechanical interfaces therebetween. In other implementations, the flow cell 1322, the sequencing interface 1324, the synthesis interface 1326, the fluidics interface 1328, and the set of module electronics 1330 may be integrated into a single device with each of the flow cell 1322, the sequencing interface 1324, the synthesis interface 1326, the fluidics interface 1328, and the set of module electronics 1330 forming a sub-component thereof.

The sequencing device 1304 is operable to read data encoded and stored as DNA in one or more wells of the storage device 1320, and may include features such as imaging devices, optical sensors, lighting devices (e.g., LEDs, illuminators), and other devices that are usable to detect characteristics of DNA stored within a well (e.g., such as the process and devices described above in relation to SBS, where fluorescent labels or tags associated with individual nucleotides are detectable by an optical sensor). The sequencing device 1304 interacts with the flow cell 1322 via the sequencing interface 1324. The sequencing interface 1324 may be a glass cover or other interface surface configured to allow the sequencing device 1304 to interact with the flow channels 410. In an example where the sequencing device 1304 includes an optical sensor and light source usable to detect tagged nucleotides, the sequencing interface 1324 may be an optically transparent glass cover that covers the flow channels 410 and prevents leakage of fluids transported within while transmitting light in each direction. In some implementations, the sequencing interface 1324 may include one or more waveguides to selectively illuminate one or more portions of the flow cell 1322.

The synthesis device 1306 is operable to synthesize DNA having a particular arrangement of nucleotides within one or more wells of the flow cell 1322 of the storage device 1320. In other implementations, the synthesis device 1306 may synthesize DNA nucleotides on a particular surface of the flow cell 1322 without wells. The synthesis device 1306 includes a store of individual nucleotides or other biological material and an input delivery device operable to communicate input biological material to one or more wells of the flow cell 1322. In some implementations this may include a set of electrodes positioned proximately to the wells and operable to attract a particular nucleotide to a particular well, while the input delivery device provides a nucleotide carrier fluid, or a nucleotide writing reagent, to the flow channel 410 via the inlet port 420. In some implementations, this may include a nucleotide injection head that may be positioned proximately to a desired well and one or more nucleotides may be released in a desired order. The synthesis interface 1326 is configured to allow the synthesis device 1306 to interact with one or more wells, and so will vary depending upon the particular synthesis device 1306. In some implementations, the synthesis interface may be a conductive layer or coupling that receives electrical characteristics from an electrode and conducts them to an area proximate to a well. In some implementations, the synthesis interface 1326 may include some or all of the fluidics interface 1328, such as where the synthesis device 1306 provides a nucleotide carrier fluid during synthesis. In some implementations, the synthesis interface 1326 may be a porous membrane that allows nucleotides to pass into the flow channel when injected by a nucleotide injection head at a desired location. In some implementations, the synthesis interface 1326 may be formed from a flexible material, or may include a plurality of small valves, or may include other features that are configured to self-seal after a nucleotide injection head provides nucleotides.

The fluidics device 1308 may include any of the devices or features described herein in relation to fluidics, and may include a fluidics network, pumps, valves, and other components operable to provide a desired fluid type, at a desired volume and pressure, to one or more of the flow channels 410, or particular locations on the one or more flow channels 410. In some implementations, the fluidics device 1308 may include electro-wetting features operable to precisely direct desired volumes of fluid to desired locations, rather than flooding the flow channels 410 with fluid. The fluidics interface 1328 will vary based on a particular implementation of the fluidics device 1308, but may include fluidics networks within the storage device 1320, the inlet ports 420, the outlet ports 422, and other components.

Fluids provided with the fluidics device 1308 may include fluid reagents that are created and used in various processes performed with the sequencing device 1304 and the synthesis device 1306, and may also include non-functional fluids such as distilled water used to flush and clean one or more components of the DNA storage system 1300. Reagents used by the sequencing device 1304 may vary from those used by the synthesis device 1306, and each device may itself use one or more different reagents during different parts of synthesis and sequencing. When used herein, any of the varying reagents that may be supplied during sequencing operations may be referred to collectively as nucleotide reading reagents, while any of the varying reagents that may be supplied during synthesis operations may be referred to collectively as nucleotide writing reagents.

The electrical interface 1310 may include wired, conductive connections, or may include wireless transceiver devices (e.g., RFID, NFC, Bluetooth, optical transmitters, inductive charging devices) that are capable of exchanging power, data, or both with the module electronics 1330 of the storage device. This may include providing power and exchanging data with an electronic memory of the storage device 1320, providing power and exchanging data with one or more sensors of the storage device 1320, and enabling other electronic or data driven capabilities of the module electronics 1330, where present.

The DNA storage system 1300 may also include a module receiver 1321 that includes one or more features to couple and statically position the storage device 1320 relative to the set of instrumentation 1301 during use, where the storage device 1320 is a removable, cartridge type of storage device. In other implementations, the storage device 1320 may comprise a flow cell 1322 that interfaces with the components of the set of instrumentation 1301. The module receiver 1321 may include a slot in which the storage device 1320 may be seated, as well as guiding features (e.g., rails) and locking features to position the storage device 1320 with a high degree of precision and immobilization, so that one or more of the set of instrumentation 1301 are repeatably and automatically positioned to interact with their corresponding interfaces.

It should be understood that the DNA storage system 1300 is one example, and that many variations are possible and will be apparent to those skilled in the art in light of this disclosure. As an example, the set of instrumentation 1301 and the storage device 1320 may have fewer components, or more components, than shown. As another example, some implementations of the storage device 1320 may include components of the set of instrumentation 1301, such as where a plurality of electrodes of the sequencing device 1304 are integrated on or within the flow cell 1322 itself. In such cases, the portion of the sequencing device 1304 paired with the set of instrumentation 1301 may include conductive switching networks that allow electrical signals to be produced and transmitted to a desired electrode within the flow cell 1322.

B. Storage Device with Selective Activation of Wells

In some DNA sequencing systems, there is an "all or nothing" approach to sequencing DNA with a plurality of wells. As an example, a particular channel of a flow cell (e.g., such as the flow channel 410) may have thousands of individual wells, each containing at least one strand of DNA. In order to sequence and read encoded data from a single strand of DNA in that channel using a process such as sequencing by synthesis, the entire channel may be flooded with chemical reagents to prepare the stored DNA for matching with optically tagged nucleotides, illuminated with a light source to make optical tags visible, and imaged with an imaging device or optical sensor to capture the tags. As may be seen, even though encoded data may only be desired from a single well, DNA stored in thousands of other wells may be impacted by the process, which may contribute, over time, and over a number of read operations, to degradation or damage to stored DNA.

Figure 11A:
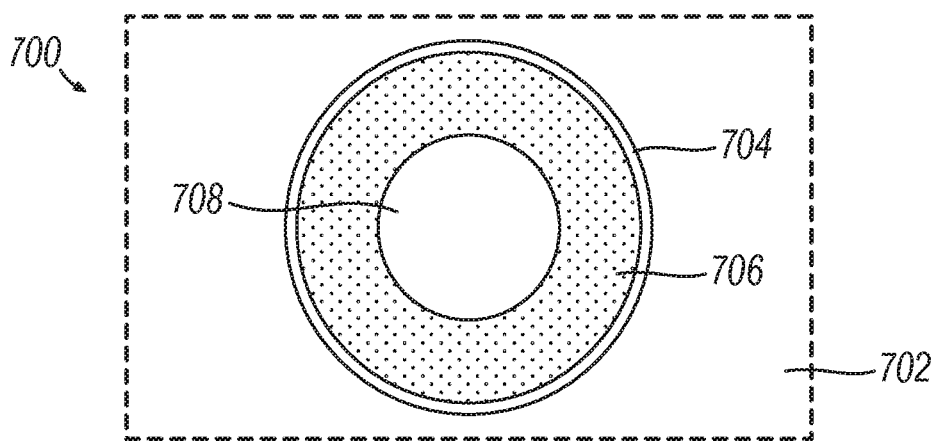
FIG. 11A depicts a top-down view of an example of a well that may be incorporated into the channel of FIG. 4.
Figure 11B:
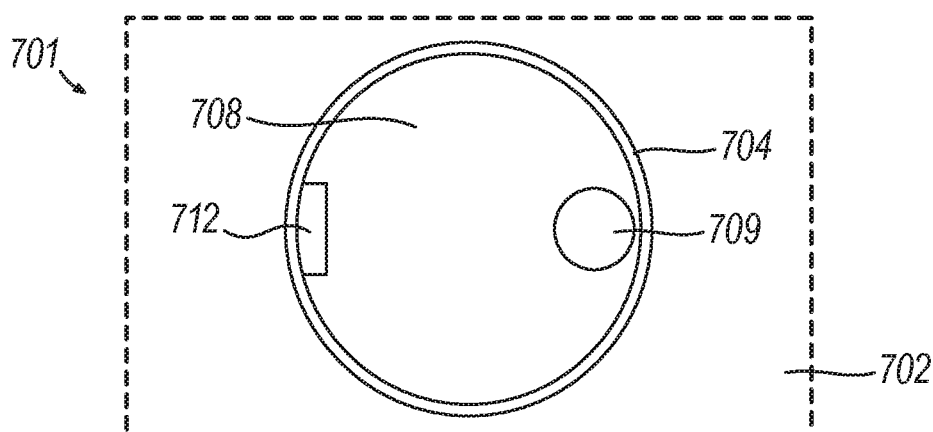
FIG. 11B depicts a top-down view of another example of a well that may be incorporated into the channel of FIG. 4.
Figure 11C:
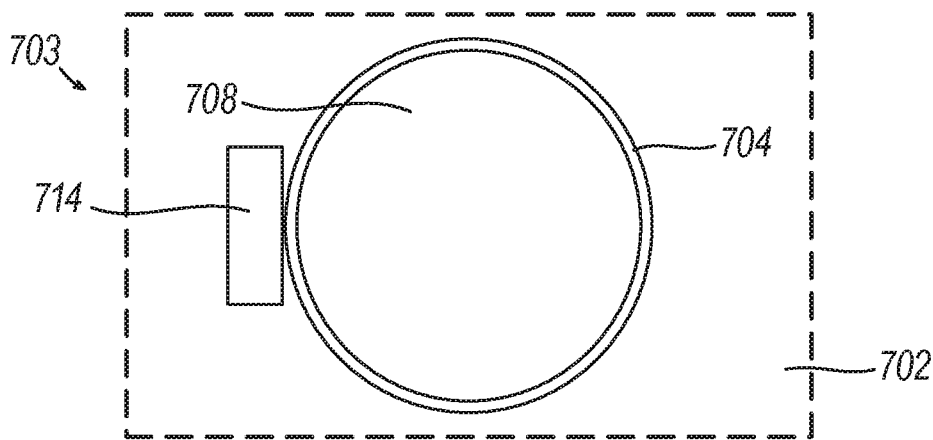
FIG. 11C depicts a top-down view of yet another example of a well that may be incorporated into the channel of FIG. 4.

FIG. 11A-11C depict top-down views of wells that may be implemented with a flow cell in order to address these aspects and others. FIG. 11A shows a single well 700 that may be positioned with a plurality of other wells on a surface 702 of a flow channel or other flow cell structure having a plurality of wells. The well 700 includes a sidewall 704 that defines an opening in the surface 702, and that descends into the structure of the flow cell. The well 700 also includes a ring electrode 706 positioned at the bottom of the well 700, having features similar to those described in the context of the electrode assembly 640, shown in FIGS. 9 and 10 In particular, the ring electrode 706 is operable in response to electrical signals to produce electrical characteristics such as current and voltage at the well 700 and within fluids proximate to the well. Due to its shape, the ring electrode 706 also allows for a port space 708 at the bottom of the well 700 that may be an optical port, a fluid port, or both. Where the port space 708 includes an optical port, the bottom of the well 700 may be constructed of glass or other optically transparent materials to allow for illumination, imaging, or both from below the well (e.g., through the closed side of the well). Where the port space 708 includes a fluid port, an opening may pass through the bottom of the well to the closed side of the well (e.g., opposite the open side of the well, and referred to as "closed" even when a fluid port is provided). While the ring electrode 706 is shown as a single monolithic electrode in FIG. 11A, it should be understood that the ring electrode 706 may in fact be formed by a plurality of individually addressable electrode segments (e.g., like the segments 642, 644, 646, 648 of the electrode assembly 640).

A fluid port may be useful to allow flushing and reagent exchange, as shown and described in FIG. 9, and may be provided as an alternative to, or in addition to a fluid path that flows over the surface 702. A fluid port may be connected to a fluidic network to allow fluid to be provided to flush used reagent from the flow channel (e.g., by expelling it through the open side of the well 700), or to provide suction to pull used reagent through the bottom of the well, either of which may be performed in conjunction with similar operations along the surface 702 (e.g., flushing fluid may be provided along the surface 700 while a fluid port is used to suction the flushing fluid and any remaining reagent through the bottom of each well). Implementations having both a fluid port and an optical port in the port space 708 may combine both functionalities by, for example, offsetting the fluid port to an edge of the port space 708 and using the remaining space of the port space 708 for unobstructed imaging and illumination of the well.

With a plurality of wells such as the well 700, each having the electrode ring 706, individual wells may selectively be "activated" or "deactivated" during sequencing or synthesis operations that may otherwise affect every well on the surface 702, even where reagents and other fluids are provided to the entirety of the surface 702. As an example, the electrode ring 705 may be operated to produce a current or voltage in one or more wells that is either attractive or repulsive to one or more nucleotides, enzymes, sequencing primers, polymerases, or other substances suspended in fluid at the surface 702, to increase the chance (e.g., as a result of an attractive electrical characteristic) that a desired substance will be pulled from fluid at the surface 702 to fluid within the well 700 itself, or to decrease the chance (e.g., as a result of a repulsive electrical characteristic) that undesired substances will flow from the surface 702 to within the well 700.

As another example, individual electrodes such as the electrode ring 706 may be activated on a per-well basis, as has been described, in conjunction with flooding the flow cell with a voltage sensitive functionalized fluid to locally influence pH of the fluid at the surface 702 and within the well 700, to aid in attracting or repulsing suspended nucleotides, or selectively activate nucleotides for binding by controlling the pH of the voltage sensitive functionalized fluid through fine control of voltages produced by the electrodes.

Used as described above, electrodes that are selectively controllable for each individual well allow for DNA to be sequenced and data to be read from a selected set of wells that are activated for sequencing, while preventing sequencing of wells that are deactivated for sequencing. The described functionality may similarly be applied to synthesis of DNA within wells, as a fluid including nucleotides of all types may be provided to the entire surface 702, and electrodes at individual wells may be activated to draw the next nucleotide needed for synthesizing into the well 700. As an example, where digital data being stored in a particular well has been encoded into a DNA format (e.g., a format that may be readily converted from and to binary, as described above) that describes an ordered sequence of nucleotides such as "AGCT", the electrode at that well may be operated by signals from the sequencing device 1304, the storage controller 1302, or both to produce an ordered sequence of currents, voltages, or other electrical characteristics to sequentially attract an A, G, C, and then T nucleotide into the well 700.

By being able to individually sequence or synthesize on a per well basis, indexes or other addressing information providing spatial locations of wells impacted by a particular read or write operation may be used to activate only those wells. Indexes or other addressing information providing spatial locations of wells impacted by a particular read or write operation may also be used to conserve reagents, conserve hardware usage, and conserve processor time that may normally be wasted during undesired sequencing or synthesis. Reagents containing suspended substances, such as nucleotides and enzymes, may also be conserved by controlling localization of substances by a combination of charged tags and stripping of enzymes from wells when they are not needed. Passive optical features may also be included in wells, including optical waveguides and polarization of materials to prevent or at least reduce cross-talk between wells, and confine illumination, whether for activation of nucleotides and other substances or to create fluorescence, and optical imaging to a desired well. By using electrodes on a per-well basis, as described above, it may be seen that movement of nucleotides and other substances to and from the well may be promoted or suppressed in order to control and create particularized desirable movements.

It should also be noted that the flexibility of the electrodes allows a single electrode associated with a well to promote desirable synthesis and writing of encoded data to a well while in a "write mode"; and to also promote desirable sequencing and reading of encoded data from the same well while in a "read mode". This flexibility may in turn allow for simultaneous reading and writing to different wells on the surface 702, such as where a particular well may be activated for writing to draw certain nucleotides and other substances from a multi-substance fluid for use in synthesis; while a different well may be activated for reading to draw certain nucleotides and other substances from the same multi-substance fluid for use in sequencing, while each suppressing the uptake of undesirable substances into their respective wells. Such functionality may be implemented as described above; and may also be implemented with one or more other features disclosed herein to aid in the simultaneous reading and writing of data to separate wells on the surface 702.

FIGS. 11B and 11C each show an alternate well implementation that provides the features described above in relation to the well 700. In FIG. 11B, a well 701 on the surface 702 does not include the electrode ring 706, and instead leaves more room for the port space 708 at the bottom of the well 701. The port space 708 may be an optical port, as described above, that allows illumination and imaging from the underside of the well 701. A fluid port 709 is also shown offset to the edge of the port space 708 as described above, to allow a larger area for unobstructed imaging through the optically transparent port space 708. An electrode 712 is mounted in the interior of the well 701, on the sidewall 704, where it may be operated to create desirable electrical conditions on a per-well basis, while also maximizing the size of the port space 708. While only one electrode 712 is shown in FIG. 11B, this well 701 may include more than one electrode 712. For instance, some variations of the well 701 may include four separate electrodes 712 at respective locations along the sidewall 704, with each electrode 712 being associated with a corresponding nucleotide base.

In FIG. 11C, a well 703 includes an electrode 714 mounted on a surface 702 at a perimeter of the well 703, just above the sidewall 704. The well 703 lacks the fluid port 709, though it may be implemented with the well 703 if desirable. The port space 708 of the well 703 is relatively large, and completely unobstructed, which may allow for the greatest level of optical exchange from beneath the well 703 (e.g., from the closed side of the well 703). As with prior examples, the electrode 714 may be operated to create desirable electrical conditions proximate to the well 703 on a per-well basis.

Each of the above described electrodes of FIG. 11A-11C may be mounted to the structure of the flow cell, with electrical connections embedded within the structure itself and routed to an underside of the structure (e.g., on the closed side of the wells, opposite the surface 702). These electrical connections may be coupled with an integrated circuit (IC) or complementary metal oxide semiconductor (CMOS) that is configured to route and control provision of electrical signals to desired electrodes, such as the control circuit 670 of FIG. 10. When used with the storage device 1320, such a control circuit may be integrated into the storage device 1320 and coupled to the underside face of the flow cell 1322, or may be part of the set of instrumentation 1301 that is precisely positioned against the underside of the flow cell 1322 when the storage device 1320 is coupled with the set of instrumentation 1301, such that each surface electrical lead of the control circuit is paired with a corresponding surface connection on the underside of the flow cell 1322, and each surface connection on the underside of the flow cell 1322 leads to an electrode for an individual well.

Figure 12A:
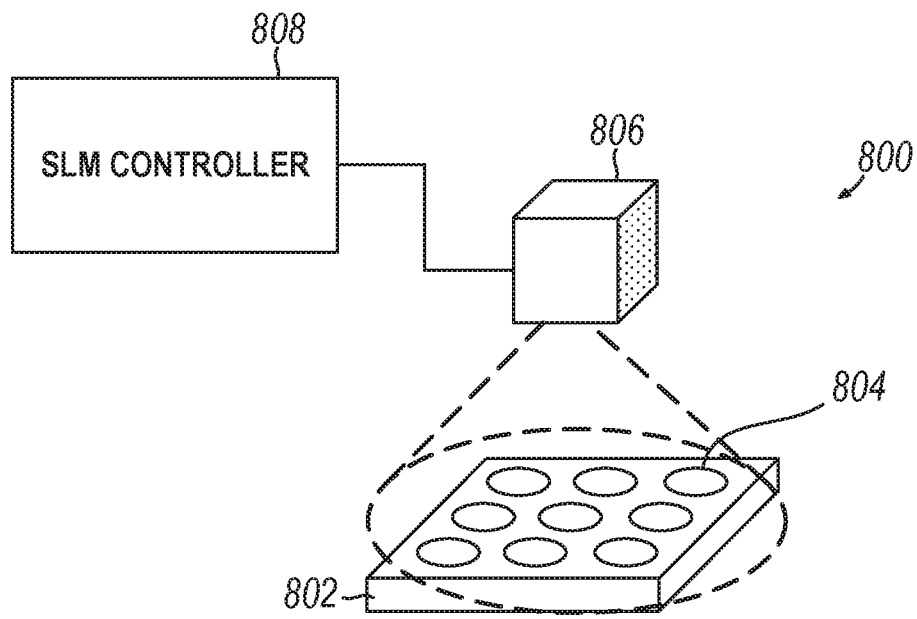
FIG. 12A depicts a schematic diagram of an example of a portion of a DNA storage system operable to, read, write, or read and write data to one or more wells.
Figure 12B:
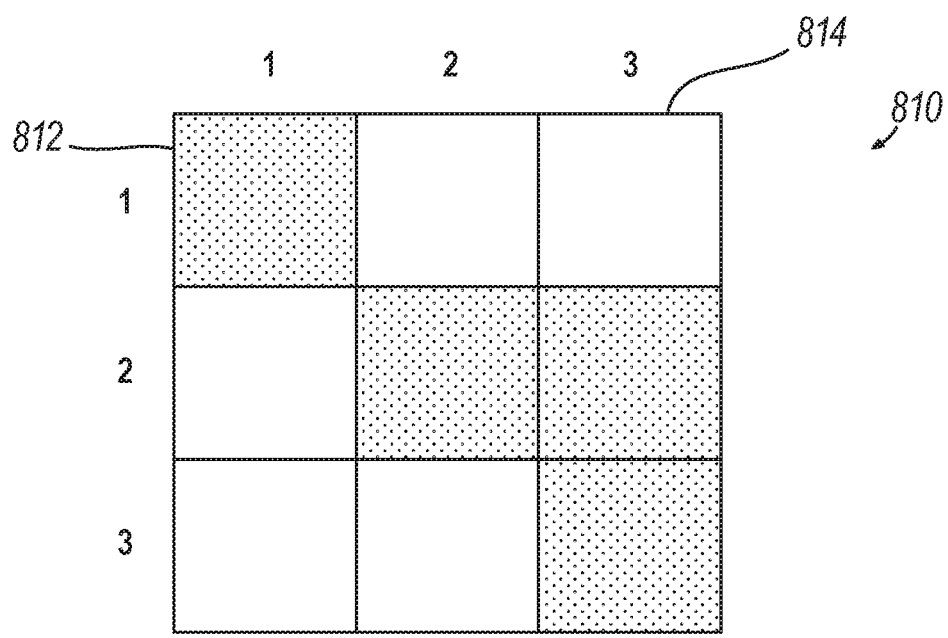
FIG. 12B depicts a schematic diagram illustrating an example of a light pattern projected by the DNA storage system of FIG. 12A onto a plurality of wells.

FIGS. 12A and 12B illustrate aspects of an alternative system for providing selective, per-well promotion and suppression of substance uptake from surrounding fluids. FIG. 12A shows a portion of a DNA storage system, such as the DNA storage system 1300, that is operable to read, write, or read and write data to one or more wells of the flow cell 1322 selectively and on a per-well basis. In that figure, a spatial light modulator (SLM) system 800 is shown that includes a spatial light projector (SLP) 806 (e.g., a light source paired with a digital micromirror device, a set of LEDs paired with an optically addressed set of liquid crystals, or another spatial light modulating device) and an SLM controller 808. The SLM system 800 is shown in relation to a flow cell 802, which may be similar to the flow cell 1322 and other examples of flow cells described herein. While the flow cell 802 is shown including a set of wells 804 that contains nine wells in a three-by-three grid, it should be understood that this is to aid in visualization of the system, and that the SLM system 800 may operate with flow cells having thousands of individual wells 804.

The SLM system 800 may be operated by one or more devices of the set of instrumentation 1301, such as the sequencing device 1304, the synthesis device 1306, or the storage controller 1302, in order to produce patterns of light onto the flow cell 802. The projected patterns of light include spatially encoded control signals that may be configured to interact with fluids and substances carried within fluids that are near or within wells 804 in order to promote or suppress movement of substances, as described above in relation to the electrodes of FIG. 11A-11C, to and from the wells 804.

The SLM controller 808 is coupled with the SLP 806 and provides control signals to the SLP 806 based upon instructions received from a device such as the storage controller 1302. Such instructions may be generated in response to requests for data to be read from the storage device 1320, for data to be written to the storage device 1320, or both. To provide examples, instructions provided to the SLM controller 808 from a device such as the storage controller 1302 may include identification of a first well 804 to be activated for writing of data (e.g., synthesis of DNA within the first well 804), identification of a second well 804 for reading of data (e.g., sequencing of DNA within the second well 804), or both, simultaneously. The SLM controller 808 may convert those instructions into control signals configured to cause the SLP 806 to project a spatial pattern of light onto the flow cell 802, corresponding to the identified wells 804 and the desired read or write operation for each well 804.

Spatially encoded light patterns provided by the SLP 806 may include, on a per-pixel basis where a plurality of pixels may correspond to each well 804 of the flow cell 802, the presence of absence of illumination; as well as variations on characteristics of illumination such as color, wavelength, frequency, magnitude or brightness, and others. Light projected into an individual well 804 may cause nucleotides, enzymes, or other substances within that well 804 to be modified in some way (e.g., cleaved, degraded, destroyed, attracted towards a light, repulsed from a light), or may cause localized changes in pH or other characteristics of the fluid to promote or suppress transport of substances to that well 804. In this manner, the SLM system 800 provides functionality similar to that described above in the context of the electrodes of FIG. 11A-11C, per-well activation or deactivation for sequencing, synthesis, or both simultaneously.

As a result, complex spatially encoded light patterns may be projected across a plurality of wells 804 simultaneously, with each well receiving a portion of the projection that is configured to cause desirable behavior of nearby fluids and substances for that well 804. FIG. 12B illustrates a simplified example of the above in relation to the flow cell 802. A spatially encoded projection 810 is shown, with 9 regions that correspond to the wells 804 in FIG. 12A. Regions that are depicted with a dotted pattern are receiving light that is configured to promote the transport of substances needed to read data from a nearby fluid to a well 804, while regions that are depicted as solid white are receiving no light, or are receiving light that is configured to suppress transport of substances in the nearby fluid to a well 804. A region 814 corresponds to a well 1-3 of the set of wells 804, while a region 812 corresponds to a well 1-1 of the set of wells 804.

As may be seen, the spatially encoded projection 810 provides light to the region 812 that is configured to promote a desired synthesis of DNA within well 1-1; and may be varied over time to promote the uptake and binding of particular desired nucleotides, in an ordered sequence, to build a desired polynucleotide. In parallel, the region 814 projected onto the well 1-3 suppresses uptake of one or more substances for the well 1-3, preventing reagents from being wasted on that well 1-3, or preventing DNA already stored within that well 1-3 from being undesirably affected by nearby fluid. As an alternative to the above example, where the solid white regions indicate light that is configured to promote reading of DNA from the corresponding well 804, the region 814 projected onto the well 1-3 may suppress uptake of substances from nearby fluid that relate to synthesis of DNA within well 1-1, while promoting uptake of substances required for sequencing of DNA within well 1-3.

In a simplest form, the alternating regions of the spatially encoded projections may be the presence of a light across the entire region, or the absence of light across the entire region. However, the SLM system 800 is also capable of projecting more complex patterns of light, such that the region 812 may be projected as hundreds or thousands of individually controllable pixels of light, each having their own characteristics and being individually projected onto the well 804, such that the SLM system 800 may both promote uptake of a certain nucleotide by the well 804, and may also direct the nucleotide to a desired location within the well 804 (e.g., centered within the well 804, offset to an edge of the well 804).

The SLP 806 may be positioned above the flow cell 1322 (e.g., on the open side of the wells 804) in order to project into the wells 804 from their open sides, via an interface such as an optically transparent glass sequencing interface 1324 above the wells 804, or may be positioned under the flow cell 1322 (e.g., on the closed side of the wells 804) in order to project into the wells 804 from their closed sides, via an optically transparent sequencing interface 1324 such as the port space 708 configured for optical transmission into the well 804.

Some implementations of the DNA storage system 1300 may include electrodes operable to provide per-well control and activation or deactivation of wells for desired procedures as described in FIG. 11A-11C, in combination with the SLM system 800. In this manner, a well may be activated for writing or reading of data by a combination of both produced electrical characteristics and projected light configured to provide a complementary or additive effect for promotion or suppression of uptake. As another example, a first set of wells may be activated for writing of data based upon produced electrical characteristics, while a second set of wells may be activated for reading of data based upon projected light. As another example, electrical characteristics and projected light may be used to perform write operations on separate wells; or read operations on separate wells. These combinations may be paired with a configuration of substance carrying fluids that allow for certain nucleotides or bases to be electrically released or transported (e.g., based upon interaction with current or voltage) while being unaffected by projected light, while other nucleotides or based are only reactive to projected light, and are not substantially affected by electrical characteristics.

Figure 13A:
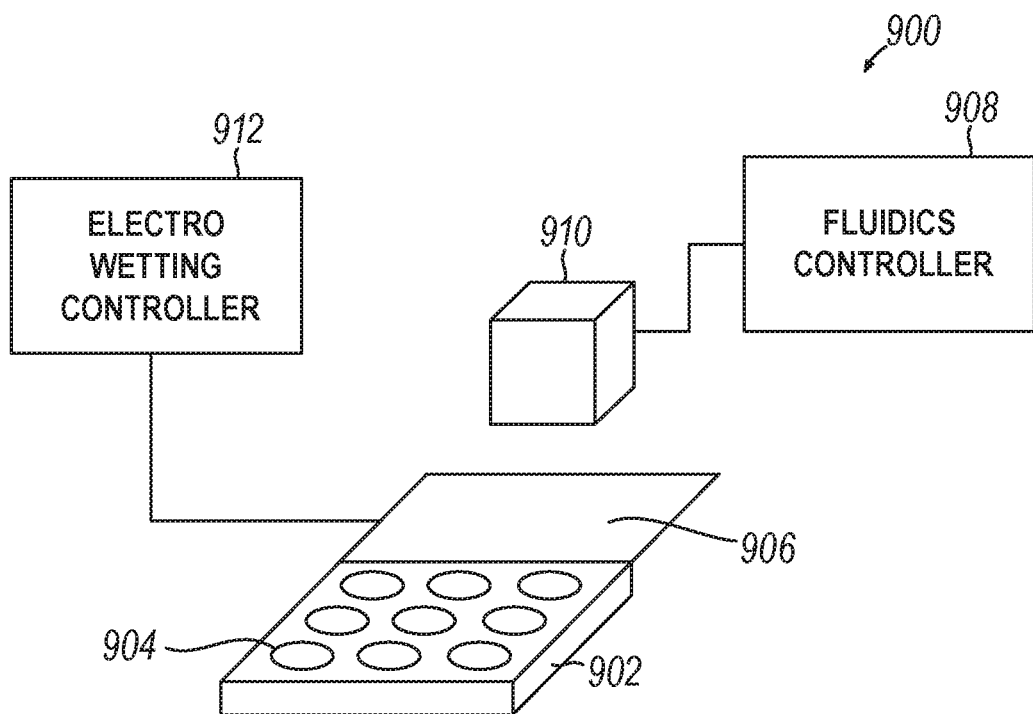
FIG. 13A depicts a schematic diagram of another example of a portion of a DNA storage system operable to read, write, or read and write data to one or more wells.

FIGS. 11A and 11B illustrate aspects of another example of a system that may provide per-well activation and deactivation, as has been described. FIG. 13A depicts a schematic diagram of a portion of a DNA storage system operable to read, write, or read and write data to one or more wells 904 on a per well 904 basis. An electro-wetting system 900 includes an electro-wetting controller 912 that is coupled with an electro-wetting surface 906. The electro-wetting surface 906 is overlaid upon a flow cell 902, with openings for a set of wells 904. The electro-wetting surface 906 may be coupled with the flow cell 902 on the top side (e.g., the open side of the wells). Also shown are a fluidics controller 908 and a fluid supply port 910, which may be components of the fluidics device 1308, and which are operable to control the flow of fluids to and from the flow cell 902 via the fluidics interface 1328.

The electro-wetting controller 912 is configured to provide electrical signals (e.g., current, voltage) to the electro-wetting surface 906 in order to produce varying electrical conditions at discrete locations across the electro-wetting surface 906. The electro-wetting controller 912 may receive instructions from a device such as the storage controller 1302 identifying a path along the electro-wetting surface 906, such as a path leading from the fluid supply port 910 to one or more of the wells 904, or a path between wells 904. The electro-wetting controller 912 may produce a sequence of electrical conditions (e.g., voltage patterns) on the electro-wetting surface 906 with a high degree of precision, both spatially (e.g., at a particular location) and electrically (e.g., a particular current, voltage, or frequency), based on these instructions. The fluidics controller 908 may receive corresponding instructions, indicating fluid types, amounts, compositions, and delivery sequences for fluid to the electro-wetting surface 906. Based on these instructions, the electro-wetting controller 912 and the fluidics controller 908 operate in parallel, managed by the storage controller 1302, or in communication with each other, in order to provide a precise amount and composition of fluid, such as a fluid droplet, to an input area of the electro-wetting surface 906, followed by a precise sequence of electrical characteristics along the electro-wetting surface 906 that are configured to transport the fluid droplet from the input area, to one or more of the wells 904.

In this manner, rather than flooding or immersing the entire surface of the flow cell 902 with fluid, individual droplets may be composed and delivered directly to a corresponding well 904 to enable writing or reading of data. This allows for selective reading and writing to individual wells 904 (e.g., described as "activating" and "deactivating" wells above in relation to electrode based and SLM implementations), as well as simultaneous read and write operations across the wells 904, without interference. The electro-wetting system 900 also conserves reagents, as it does not require flooding or immersion of multi-substance reagents that may include a number of nucleotides, enzymes, or other substances that are necessary for an operation in one well 904; but may be wasted or may interfere with an operation in another well 904. Instead, a fluid droplet that is substantially the same volume as the well 904, and that contains only the substances needed for an operation in that well 904, may be delivered directly to that well 904.

Figure 13B:
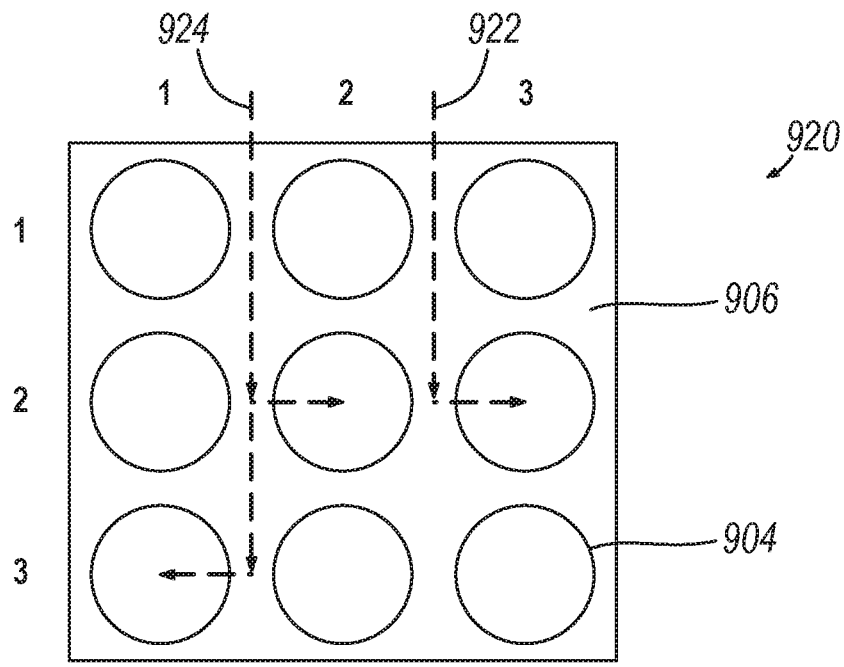
FIG. 13B depicts a schematic diagram illustrating an example of electro-wetting of a plurality of wells.

FIG. 13B illustrates an example of an electro-wetting process. A surface map 920 corresponds to the set of wells 904. As with prior examples, nine wells 904 are shown for simplicity, but it should be understood that the electro-wetting system 900 may support surfaces having thousands of wells 904, such as by introducing additional fluid supply ports 910 at discrete locations across the electro-wetting surface 906, in order to minimize travel distance for a particular droplet. A first path 922 is illustrated on the surface map 920 as a dotted line, traveling along interstitial spaces between wells 1-2 and 1-3, before reaching an interstitial space proximate to well 2-3, and being directed into that well 2-3. The first path 922 may be produced by a sequential set of electrical conditions (e.g., applied voltage changes) along the electro-wetting surface 906, configured to attract the droplet to a subsequent location, repulse the droplet from a current location, or both; and may also include pairs of electrical conditions that surround the first path 922 and direct the droplet back onto the path, somewhat similar to a set of "rails" which both guide the droplet and prevent deviation from the first path 922.

Similarly, a second path 924 travels along interstitial spaces between wells 904 until reaching well 2-2, where a droplet may be split into two, with one portion being directed into well 2-2, and a second portion continuing along to well 3-1. This path may be produced similarly to the first path 922, with an additional process of splitting the droplet when the path branches. This may be performed by, for example, creating electrical conditions along a midline of the droplet to divide it in two, paired with electrical "rails" or other conditions to direct each sub-droplet from the location of splitting to a subsequent location. The second path 924 may be useful where, for example, well 2-2 and well 3-1 are each being prepared to synthesize DNA, and so require the same or a very similar fluid composition.

The electro-wetting system 900 may be paired with other systems disclosed herein, such as the per-well electrodes of FIG. 11A-11C, the SLM system 800, or both. As an example, activation of electrodes may be paired with delivery of a droplet to filter out trace amounts of undesired substances that may be collected from the electro-wetting surface 906 during transit of a droplet. Alternately, droplets may travel across wells instead of or in addition to interstitial spaces, with electrodes of traversed wells being activated to prevent uptake. As another example, a droplet may contain a mix of substances, with separate subsets of the mix being intended for two separate wells. The mixed droplet may be transported to a first well, which may activate an electrode to extract its desired subset from the droplet, so that the droplet may be transported to the second well to deliver the remaining substances.

The SLM system 800 may be paired with the electro-wetting system 900 and may project patterned light onto wells that a droplet is traveling past in order to suppress accidental uptake of substances by those well as the droplet passes. Alternately, the SLM system 800 may project patterned light onto the interstitial spaces or other paths of the electro-wetting surface 906 that droplets travel on, in order to destroy or degrade remnant substances and prevent them from being absorbed by a subsequent bead.

In some implementations, the electro-wetting surface 900 may be a component of the storage device 1320; and may be integrated and coupled with the flow cell surface as shown in FIG. 13A. In other implementations, the electro-wetting surface 906 may be a component of the set of instrumentation 1301 (e.g., the sequencing device 1304 or the synthesis device 1306), and may be coupled against the surface of the flow cell 1322 as a result of the storage device 1320 being inserted or otherwise coupled with the set of instrumentation. As an example, where the storage device 1320 is inserted into the module receiver 1321, the electro-wetting surface 906 may slide into a slot or opening in the storage device 1320 and be automatically aligned with the wells of the flow cell 1322 as the storage device 1320 is locked into place, as has been described, such that discrete portions of the electro-wetting surface 906 may still be accurately addressed to individual wells.

Figure 14:
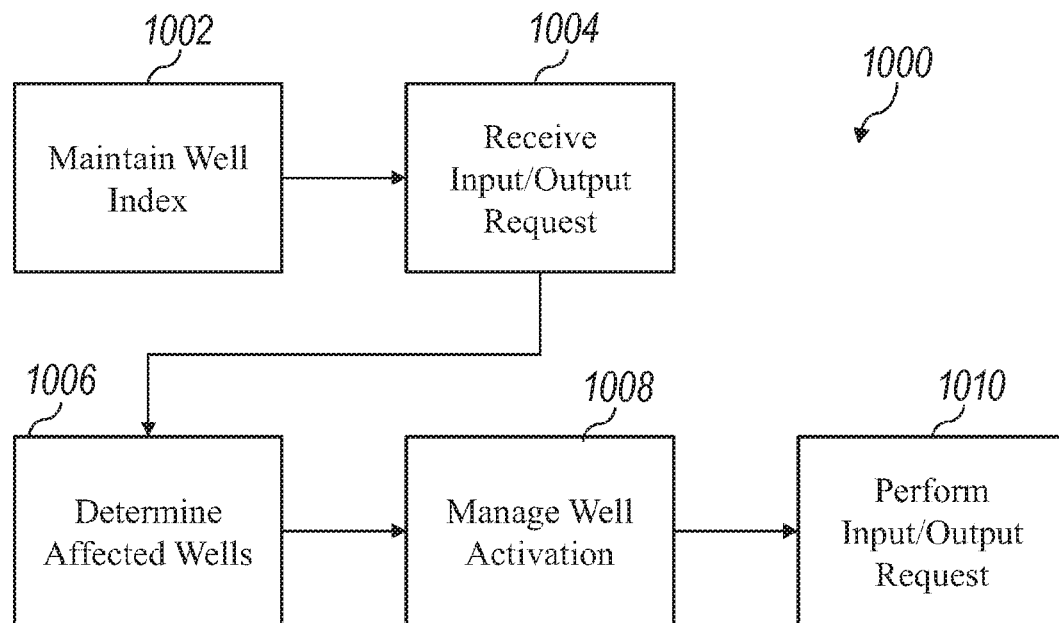
FIG. 14 depicts a flowchart of a process that may be performed to provide controlled regions of reading and writing to a plurality of wells.

Several implementations for providing selective activation and deactivation of wells, on a per-well basis, for reading and writing operations have been disclosed. FIG. 14 depicts a flowchart of a process 1000 that may be performed to utilize such systems and devices to provide controlled regions of reading and writing to a plurality of wells. An index of wells may be maintained (block 1002) by a device such as the storage controller 1302, and that may include details such as the status of each well of the flow cell 1322. Well status information may uniquely identify each well (e.g., by an ID number, a physical location on a surface of the flow cell 1322, or both), and indicate whether each well contains a polynucleotide, or is empty. Well status information may also include identifiers for information stored in that well, such as a list of files, a description of data, a unique write operation identifier, a time and date of write operation, or other similar information. Such information may also be stored as a separate file index that indicates one or more wells that each file is stored in by listing out the unique identifier for those wells, with the well index containing the unique identifier and the physical location or address of the well. The well index, file index, or both may be stored on a memory or drive accessible to the storage controller 1302; or may be stored on an electronic memory that is a component of the storage device 1320, as will be described in more detail below.

The DNA storage system 1300 may receive (block 1004) requests from users, or from other system and devices, for data to be written to or read from a storage device; and may store data associated with those requests until they may be completed. As a request is received (block 1004), the DNA storage system 1300 may determine (block 1006) one or more wells affected by the request. For a request to read data and provide output, this may include referencing the well index to determine the identity of wells which may be read from in order to generate a description of the machine-written polynucleotide contained therein; and convert the polynucleotide into digital data. For a request to write input to a storage device, this may include referencing the well index to identify one or more fully or partially empty wells that provide the required amount of storage based upon the input size; and assigning portions of the input to each well.

The DNA storage system 1300 may manage (block 1008) well activation for the affected wells, which may include any or all of the following: (1) activating the affected wells for reading of data or activating the affected wells for writing of data; (2) deactivating or otherwise protecting wells that are nearby or adjacent to affected wells (e.g., such as where the electro-wetting system 900 may provide droplets to a target well, and adjacent wells may be deactivated); and/or (3) deactivating every well that is not an affected well (e.g., such as where the entire surface of the flow cell receives a multi-substance fluid, and every non-affected well is deactivated to prevent undesired synthesis or sequencing). As has been described, well activation may include using systems and devices such as those shown in FIGS. 11A-11B to promote desired transport and binding of substances in a target well, to suppress undesired uptake of substances in untargeted wells, or both. While it may be more accurate, in some implementations, to say that a nucleotide or other substance is activated while the well itself remains unchanged, it should be understood that "activation" of a well is used herein to contemplate both changes to characteristics associated with the well (e.g., electrical characteristics of the area near the well), as well as changes to substances near the well (e.g., activation of nucleotides in response to voltage or photonic energy).

The DNA storage system may perform 1010 the input and output requests by sequencing or synthesizing DNA in the respectively activated wells, using methods such as those described herein, which may include providing various reagent fluids to some or all of the wells, providing ordered sequences of nucleotides to wells, illuminating and imaging wells, and others. As has been described, data to be written to a well may be encoded into a DNA format (e.g., where nucleotide bases correspond to binary data, such as where each individual nucleotide corresponds to a different binary couplet), which is used to determine the sequence of nucleotides written to a well. Data that is read from a well will be in the DNA format initially, and will describe an ordered sequence of nucleotides, which may be converted back into binary data using corresponding decoding rules.

B. Caching Methods for Simultaneous Reading and Writing

In addition to benefitting from features that allow for simultaneous reading and writing of data to a storage device, systems such as the DNA storage system 1300 may also benefit from DNA storage specific approaches to caching that may simulate simultaneous reading and writing of data, such that users or other systems and devices that depend upon the DNA storage system 1300 are not impacted by occasional delays in the ability of the DNA storage system 1300 to write data to the storage device 1320. Some implementations of these caching strategies may also minimize the likelihood of future read-write conflicts.

While the set of instrumentation 1301 may include various system-level caching features (e.g., such as a processor, memory, or motherboard cache built into the storage controller 1302 and configured to automatically cache data relating to basic operations of the processor), it may be advantageous to provide a cache memory, such as an electronic memory, that is associated with the storage device 1320 rather than the set of instrumentation 1301. As an example, where data is being written to the storage device 1320 and a user initiates dismounting of the volume from the set of instrumentation 1301 of the DNA storage system 1300 before writing to the flow cell 1322 may be completed, unwritten data may be stored on the electronic memory, and will travel with the storage device 1320 until such a time that it may be written to the flow cell 1322. As another example, where an index of wells is maintained (block 1002) such as described in FIG. 14, it may be useful to maintain that index on an electronic memory that travels with the storage device 1320, instead of, or in addition to, storing the index in a cloud storage, or on a permanent storage volume of the set of instrumentation 1301 of the DNA storage system 1300. In this manner, if the storage device 1320 is transported and mounted with a set of instrumentation 1301 of a different DNA storage system 1300, the well index is immediately available, rather than requiring information be obtained from the cloud storage volume, or from a previously coupled set of instrumentation 1301 of the DNA storage system 1300.

Figure 15:
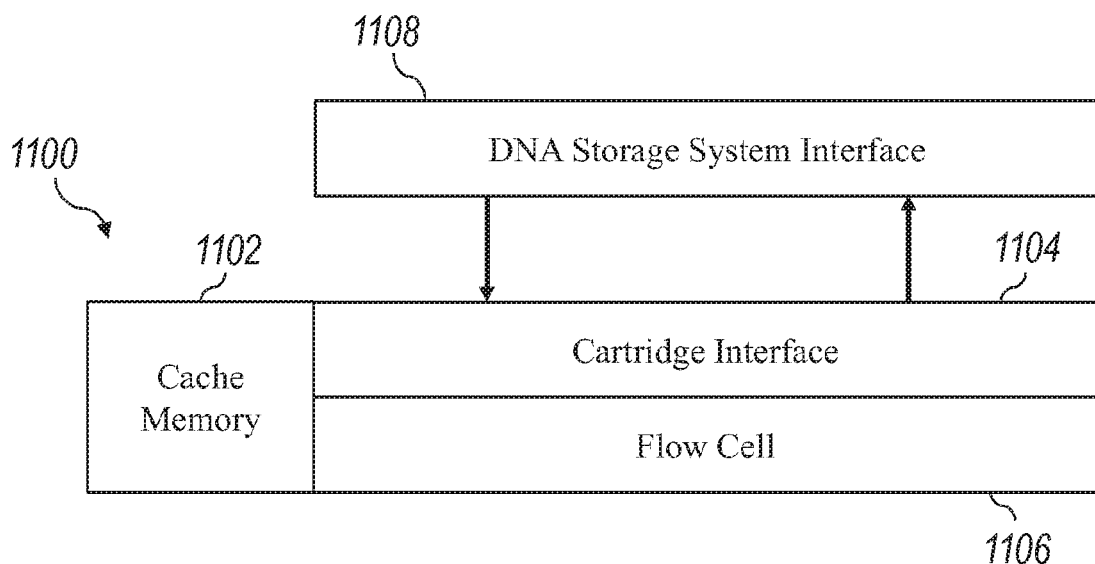
FIG. 15 depicts a schematic diagram illustrating an example of a storage device usable with a DNA storage system.

FIG. 15 depicts a schematic diagram illustrating an example of a storage device 1100 usable with a DNA storage system such as the DNA storage system 1300. The storage device 1100 includes a cartridge interface 1104 (e.g., the sequencing interface 1324, the synthesis interface 1326, etc.) configured to couple the storage device 1100 with a DNA storage system interface 1108 (e.g., the set of instrumentation 1301, the electrical interface 1310). The storage device 1100 also includes a flow cell 1106 on which data may be stored and written as polynucleotides. A cache memory 1102 is included in the storage device 1100, and may be part of the module electronics 1330, such that it is coupled with the electrical interface 1310 when the storage device 1320 is placed or mounted in the DNA storage system 1300. The electrical interface 1310 both powers the cache memory 1102 and allows for exchange of data between the cache memory 1102 and the storage controller 1302 or other devices. In some implementations, the cache memory 1102 may be a non-volatile, electronic solid-state memory configured to be physically connected for data transfer. In some implementations, the cache memory 1102 may be configured for wireless data transfer when coupled to the DNA storage system 1300. In some implementations, the cache memory 1102 may include several memories, such as a large solid-state memory intended for storage of data, and a smaller wireless memory intended for storing small amounts of identifying information (e.g., such as an RFID memory that contains a unique identifier associated with the storage device 1320).

Figure 16:
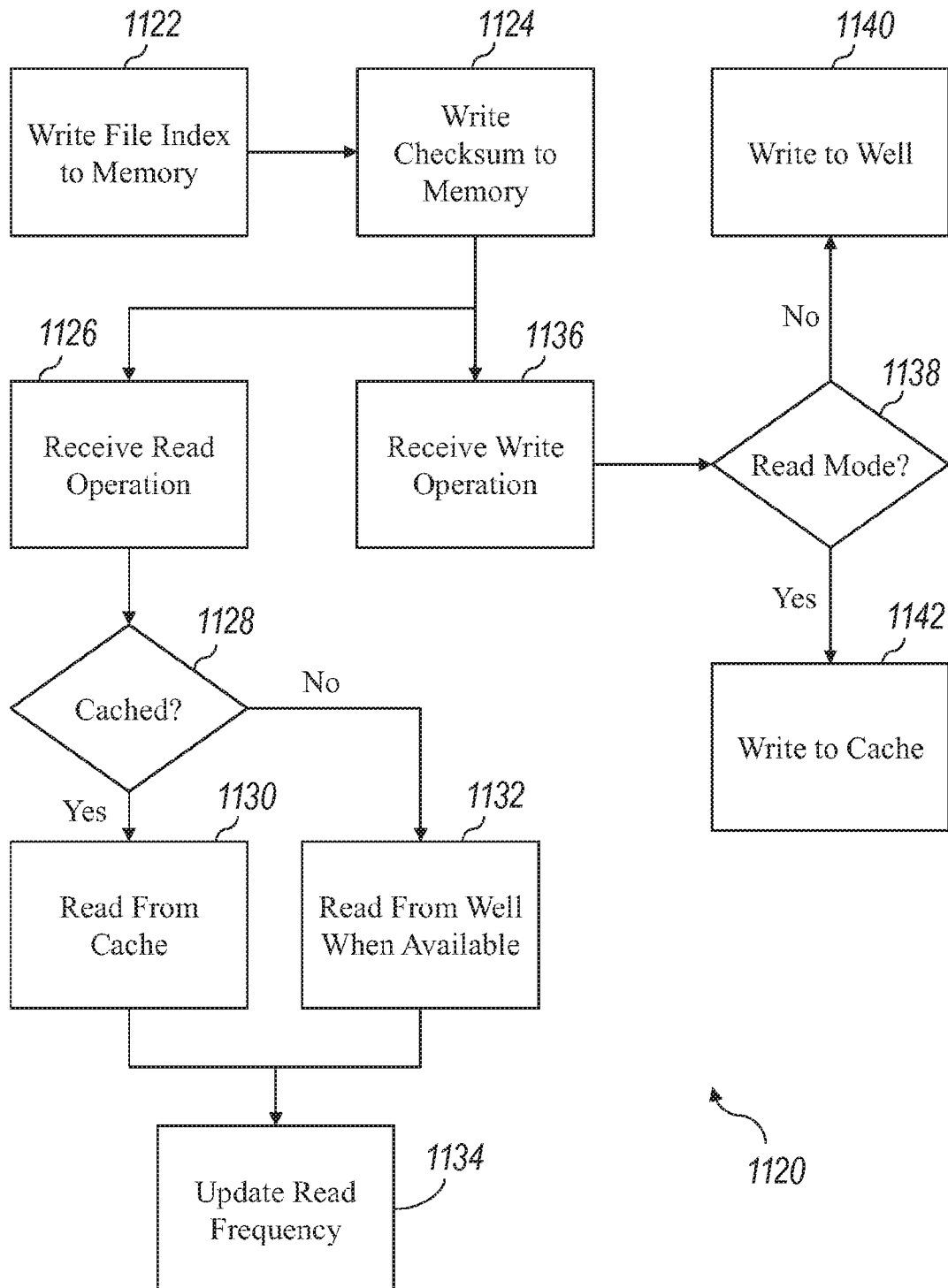
FIG. 16 depicts a flowchart of a process that may be performed to provide caching of read and write operations to the storage device of FIG. 15.

In addition to advantages of the cache memory 1102 already described, particular caching strategies may be implemented for the DNA storage system 1300 where the cache memory 1102 is available. As an example, FIG. 16 depicts a flowchart of a process 1120 that may be performed to provide caching of read and write operations to the storage device 1100. As data is written to the storage device 1100 with the DNA storage system 1300, additional data may be written to the cache memory 1102. This may include writing (block 1122) a file index to the cache memory 1102, which may describe the contents of a plurality of wells, and locations of particular files or data, whether stored in the plurality of wells, stored on the cache memory 1102, or both. Such information may be used to enable later access to and retrieval of requested data. Checksum data for individual files or bundles of data may also be written (block 1124) to the cache memory 1102 and may be associated with the file index.

Storing an index, a list of checksums, or both for files and data on the cache memory 1102 may enable faster reading and writing of data in the future, as compared to storing such data on the flow cell 1106, and requiring it to be sequenced before the drive contents are accessible, and frequently synthesized to reflect changes; or storing such data on a cloud storage or server, which may require network connectivity and permissions for accessing such data before the drive contents are accessible. Storing such data on the cache memory 1102 in addition to storing it on the flow cell 1106 itself, or on a network accessible volume, provides an additional advantage of redundant storage of such data, as the loss of file tables and indexes may result in either the complete loss of data stored on the flow cell 1106, or a greatly increased cost in time and resources to rebuild the file indexes based upon well-by-well examination.

While the storage device 1100 is coupled with the DNA storage system 1300, the system may receive (block 1126) read operations, and may receive (block 1136) write operations, from users, or from systems and devices in communication with the DNA storage system 1300. As has been discussed, in some cases it may not be possible to allow for simultaneous reading and writing of data to separate wells of the flow cell 1106. This may be due to limitations of the DNA storage system 1300, or limitations on the storage device 1100. As an example, some implementations of the DNA storage system 1300 may lack selective, or per-well activation for reading and writing of data, such as described in the context of FIGS. 9-12; and instead sequence and synthesis data in bulk operations that may impact every well of the flow cell 1106. In such implementations, the storage device 1100 may be considered to have two mutually exclusive modes-a read mode and a write mode.

While such implementations may particularly benefit from the disclosed caching strategies, it should be understood that even implementations that support simultaneous reading and writing may encounter various scenarios where they are effectively in a read mode or write mode, such as where well activation features are limited to a certain number of simultaneous operations within a time period (e.g., the electro-wetting system 900 may be limited to the number of wells it may activate within a given time period, and a number of data read requests may result in subsequent data write requests being queued for a period of time).

Where a read operation is received (block 1126), the DNA storage system 1300 may examine the file index to both locate the requested data and determine whether it is currently stored (block 1128) on the cache memory 1102. Requested data may be available on the cache memory 1102 in different scenarios. As an example, where data is written to the storage device 1100, and then requested shortly after, it may still be stored in the cache memory 1102. As another example, where data was recently read from the flow cell 1106 based upon a request, it may be stored in the cache memory 1102 until overwritten. As another example, the DNA storage system 1300 may be configured to flag certain data that is stored on the flow cell 1106 to be also maintained in the cache memory 1102 when possible, due to a manual configuration by a user, or based upon an automatic determination by the DNA storage system 1300 based upon the frequency of read requests for such data.

Where the requested data is available from the cache memory 1102, the DNA storage system 1300 will read (block 1130) the data from the cache memory 1102 to service the request, which may allow the storage device 1100 to be maintained in a write mode, while simultaneously allowing data to be read (though from the cache memory 1102 and not from the flow cell 1106). Where the requested data is not stored in the cache memory 1102, the DNA storage system may read (block 1132) the data from the flow cell 1106 when such functionality is available (e.g., when the storage device 1100 is in read mode, or when a read operation is otherwise available). Where the storage device 1100 is in write mode and actively writing data to the flow cell 1106, it may not be advantageous to prioritize switching back to read mode, due to the time and reagent cost in switching between modes and conditioning wells. However, where data that is queued to be written is of a size that may be stored on the cache memory 1102, it may be advantageous to switch to read mode and allow the requested data to be read (block 1132) from the well, while input data is stored on the cache memory 1102. In such a case, a user or other system or device that has requested data be written and read perceives that such actions are being performed simultaneously, since output data is being read from the flow cell 1106 while input data is being written to the cache memory 1102.

After each read operation, the file index on the cache memory 1102 or another data set may be updated (block 1134) to reflect the read frequency for recently requested data, with such data sets being useful for future determinations for data that should be cycled into the cache memory 1102 due to frequency of use (e.g., data that may be requested every single data) or patterns of use (e.g., data that is requested every Friday may be cycled into the cache memory 1102 on Thursday at a low priority such that it is completed during a period of time where there may be reduced requests for reading and writing of data).

With continued reference to FIG. 16, where a write operation is received (block 1136), the DNA storage system 1300 may determine (block 1138) whether the storage device 1100 is currently in read mode. Where the storage device 1100 is currently in read mode, the input data associated with the write operation may be written (block 1142) to the cache memory 1102 and flagged for writing to the flow cell 1106 when available. Where the storage device is already in write mode, the input data may be written (block 1140) to one or more wells of the flow cell 1106.

The disclosed caching methods may also be influenced by a caching strategy that gives preference to staying in a current mode (e.g., read mode or write mode) over other considerations, such that all queued read operations may be performed before switching to a write mode, regardless of the order of arrival of the requests; and may even maintain a read mode for a brief period of time past completion of the last read request in order to allow for other read requests to arrive and be serviced before switching modes. In addition to reducing the overall number of mode switches performed in a given period of time, such a strategy reduces the risk of cross contamination of read-specific reagents with write-specific reagents, which may otherwise occur more frequently as a result of more frequent switching of modes.

C. Multi-Volume Management Methods for Simultaneous Reading and Writing

A system such as the DNA storage system 1300 may also benefit from DNA storage specific approaches to multi volume management that may allow for simultaneous reading and writing of data, redundant storage of data, error checking of data, and improved reading and writing speeds for data. For example, in some implementations, when data is written to a location (e.g., a well in a flow cell), a mirrored copy may also be automatically be written to a second location (e.g., a second well in the same flow cell, or a well in a different flow cell). In some such implementations, the existence of one or more mirrored copies may be used to improve system performance such as by supporting parallel operations. For example, in some implementations, a DNA storage device may comprise two flow cells (e.g., two flow cells 601), a first of which is used for read operations, and a second of which is used for write operations. In such a scenario, if two different users wanted to concurrently read from, and write to, data stored in a particular location, the user making the read request may be fulfilled by sequencing the copy of the data stored in the first flow cell 601; while at the same time the write request was fulfilled by writing a new polynucleotide into the appropriate location in the second flow cell 601. Subsequently, when the requests had been processed (e.g., during a low activity period) the first flow cell 601 may be resynchronized with the second flow cell 601, thereby ensuring that whatever data had been written to the second flow cell 601 may be read using the first flow cell 601 whenever the next read request was issued.

As another example, in some implementations, when data is to be written, in addition to writing that data, a system may be implemented to write both that data as well as a redundancy value that may be used to recreate a portion of the data in the even it was lost. To illustrate, consider Table 1 below, which provides an example of such a redundancy value as may be generated for data stored in the form of four polynucleotides each of which stores four bits of data.

TABLE 1

Example approach to storing data with a redundancy sequence that allows a portion of the data to be recreated in the event it is lost.

| Data Sequence 1 | Data Sequence 2 | Data Sequence 3 | Data Sequence 4 | Redundancy Sequence | |
|---|---|---|---|---|---|
| 1 | 1 | 1 | 1 | XOR | 0 |
| 1 | 1 | 1 | 0 | XOR | 1 |
| 1 | 1 | 0 | 0 | XOR | 0 |
| 1 | 0 | 0 | 0 | XOR | 1 |

In some implementations, 16 bits of data may be broken up into four four-bit sequences, and a fifth four-bit sequence may be created by applying the logical XOR operator to the bits from the first four sequences. These five sequences may then be stored in five polynucleotides in five different locations in a DNA storage device. Then, in the event the data in one of the locations was found to be corrupted and/or inadvertently misread during a sequencing operation, that data may be recreated by applying the XOR operator to the remaining four sequences and storing encoding the result as a new polynucleotide in the location that previously held the corrupted data.

During a reading and/or writing process, "phasing" and/or "pre-phasing" may occur and introduce an error into the resulting written or read sequence. "Phasing" refers to an instance when a reversible terminator for a first incorporated nucleotide is inadvertently removed, such as by an interaction with remnant reagents that have not been flushed out of the flow cell, and a second nucleotide is incorporated. During a writing process, this may result in two nucleotides being written for a particular DNA sequence instead of a single nucleotide. During a reading process, this may result in the fluorophore associated with the first nucleotide not being detected, thereby offsetting the read-out sequence by skipping over one nucleotide. "Pre-phasing" refers to an instance when a nucleotide is not incorporated. During a writing process, this may result in no nucleotide being written to the sequence. During a reading process, this may result in no fluorophore associated with a nucleotide for the sequence being detected or the prior fluorophore associated with the prior nucleotide being detected again, thereby offsetting the read-out sequence by lagging behind or double reading one nucleotide. The use of a redundancy sequence may detect errors in one or both of the writing and/or reading processes.

Figure 17A:
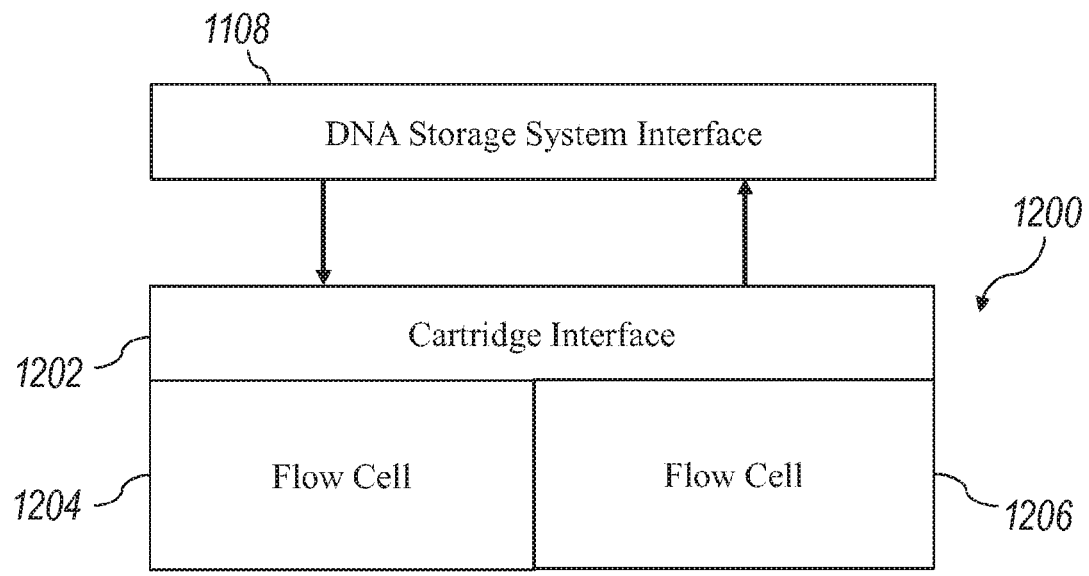
FIG. 17A depicts a schematic diagram of another example of a storage device usable with a DNA storage system.

FIGS. 17A an 17B depict schematic diagrams of storage device configurations to allow for multi-volume management for DNA storage. FIG. 17A shows a storage device 1200, that may be coupled with the DNA storage system interface 1108 (e.g., as described in the context of the storage device 1100). The storage device 1200 includes a cartridge interface 1202, having similar features and capabilities as described in relation to the cartridge interface 1104, and two distinct flow cells 1204, 1206 having similar features and capabilities as other flow cells described herein. While referred to as flow cells, it should also be understood that the first flow cell 1204 and the second flow cell 1206 may instead be distinct channels, such as two separate channels from the flow channels 410, which may be independently managed from a fluidics, sequencing, and synthesis perspective.

Figure 17B:
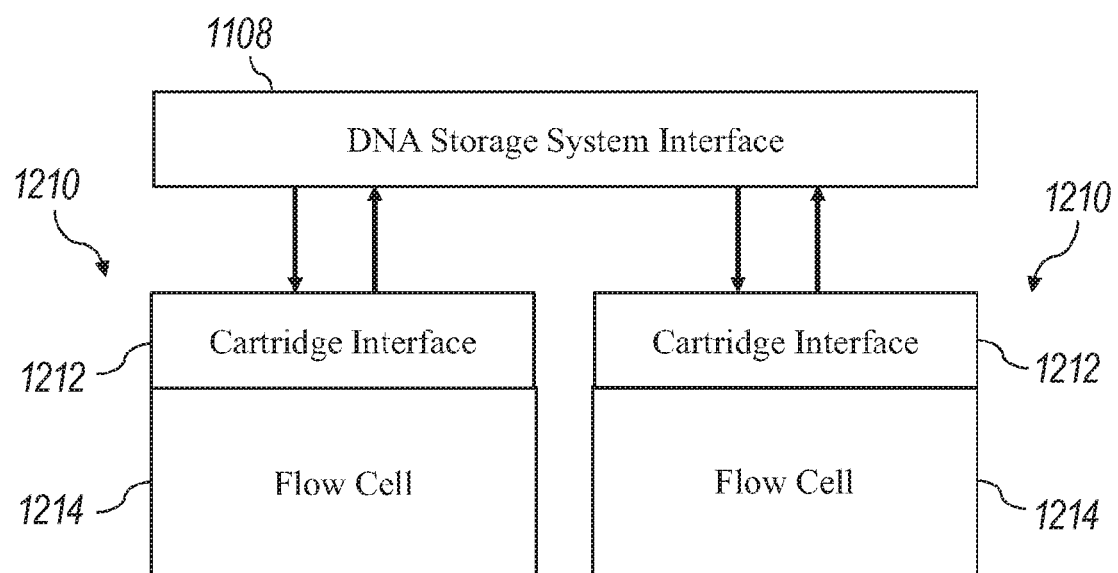
FIG. 17B depicts a schematic diagram of a configuration of a plurality of storage devices usable with a DNA storage system.

FIG. 17B shows a configuration for storage devices similar to that shown in FIG. 17A but having two distinct storage devices 1210. Each storage device 1210 of this example has a cartridge interface 1212 having similar features and capabilities as described in relation to the cartridge interface 1104. Each storage device 1210 of this example also has a flow cell 1214 having similar features and capabilities as other flow cells described herein. Each of the two distinct storage devices 1210 is coupled with the DNA storage system interface 1108, which itself may be modified slightly to simultaneously couple with the two distinct storage devices 1210. For instance, the DNA storage system interface 1108 may double or otherwise provide additional capabilities for each of the set of instrumentation 1301; or position the two storage devices 1210 proximately to each other, and configure the set of instrumentation 1301 such that they may float between modules, such as in the case of an illumination and optical sensing device that may be moved between modules. Alternatively, the DNA storage system interface 1108 may provide a set of instrumentation 1301 that simultaneously interacts with each module, such as in the case of a fluidics device that may provide fluids to each module via the fluidics network.

Figure 18:
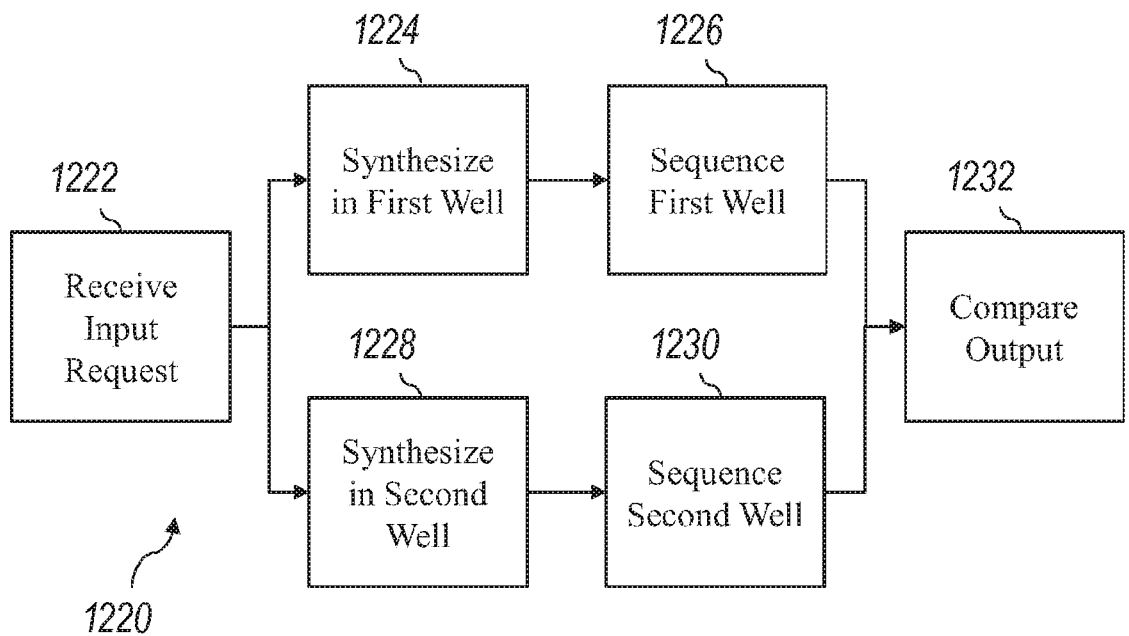
FIG. 18 depicts a flowchart of a process that may be performed to provide redundant data writing and reading with a storage device.

FIG. 18 depicts a flowchart of a process 1220 that may be performed to provide redundant data writing and reading operations with a storage device such as the storage device 1200, or the storage devices 1210. When an input request is received (block 1222), providing input data that should be written to wells of a flow cell, the DNA storage system 1300 may, in parallel or in close sequence depending upon its capabilities, synthesize (block 1224) and store the input data in a first well; and synthesize (block 1228) and store the input data in a second well. While FIG. 18 describes a first well and a second well, it should be understood that data may advantageously be performed across three or more wells. The redundancy of the first well and second well may be used for error checking, such as by sequencing one or both of the polynucleotides of the first well and/or second well to determine if phasing or pre-phasing occurred during a read and/or write process. Assuming there were no errors in synthesis, identical copies of polynucleotides corresponding to the input data in the first well and the second well. This provides various advantages, depending upon the nature of the first well and the second well.

As an example, with reference to the storage device 1200, the first well may be located in the first flow cell 1204, while the second well may be located in the second flow cell 1206. In such a case, the written data is redundantly stored across two separate volumes, which is desirable for data integrity and minimizing risk of data loss. Additionally, since the data is cloned across two distinct flow cells, the DNA storage system 1300 may also simultaneously read and write data to the volume, by, for example, maintaining the first flow cell 1204 in write mode at all times, while switching the second flow cell 1206 into a read mode as requests for output data are received. Both of these advantages also apply where the first well is in the flow cell 1214 of one of the storage devices 1210 and the second well is in the flow cell 1214 of the other storage device 1210.

Even where another storage device (e.g., the storage device 1100) is used, and the first well and second well are each located in the flow cell 1106, there are some advantages to cloning data cross individual wells in the same flow cell. In addition to providing data redundancy to reduce the risk of data loss to a well malfunction, or unexpected degradation of DNA within one well, cloning the written data may provide additional error checking capabilities, regardless of where the two wells are located. As an example, where the input data is written to separate wells as shown in FIG. 18, it may then be read back from the two separate wells by sequencing (block 1226) and reading the data from the first well, and sequencing (block 1230) and reading the data from the second well. A comparison (block 1232) of the output that is read from each well, either of the full file or data sets, or a checksum of the output, will indicate whether the polynucleotide written to one cell was either erroneously synthesized, erroneously read, or has subsequently degraded for some reason.

In some implementations, the synthesizing of a polynucleotide in the second well may be done based on the synthesizing of the polynucleotide in the first well. That is, clonal amplification of the polynucleotide written in the first well may be performed and one or more cloned polynucleotides may be stored in second well and/or in a fluidic storage chamber. Sequencing of the clonally amplified polynucleotides within the first well may be performed to determine the sequence of nucleotides in the first well. The sequence of nucleotides in the first well may be compared to the instructed written polynucleotide to determine if any phasing or pre-phasing errors occurred during the write process. If an error occurred, the one or more cloned polynucleotides stored in second well and/or in a fluidic storage chamber may be discarded as corrupt and the write process may occur again. If no errors occurred, then the one or more cloned polynucleotides stored in second well and/or in a fluidic storage chamber may be cloned and stored in the first well and/or one or more other wells to provide two or more identical polynucleotides described herein.

Some implementations that perform cloned writing of data as shown in FIG. 18, and that also include the SLM system 800, with the first well and the second well contained within the same flow cell, may benefit from the SLM system's 800 capabilities to project encoded spatial light across the flow cell surface. In such a scenario, the flow cell may already be receiving the required reagents to synthesize and write data to the first well, meaning that the second well may also typically be receiving the same reagents. In that scenario, the SLM system 800 may also be projecting patterned light onto the first well to complete synthesis, and since the second well is on the same flow cell, and within the potential projection footprint of the SLM system 800, it may require little additional resources in terms of reagent or processor time to duplicate the pattern projected onto the first well, such that the same pattern is also projected onto the second well.

In yet another implementation of the process of FIG. 18, a single well may be used as both the first well and the second well, such that two identical polynucleotides may be created in a single well. In addition to providing redundancy against degradation of a single strand, the two separate strands may be built from optically tagged or marked nucleotides and immediately illuminated and imaged upon completion, within the same well, in order to determine if one of the strands was corrupted during writing. One or more of the disclosed implementations may also include attaching additional nucleotides onto a machine written polynucleotide representing information such as hash values or checksums of nucleotide sequences within the strand, spacer values indicating the end of a particular sequence of data and/or separating a hash value from a subsequent nucleotide sequence. As has been described, such information may be written to the polynucleotide, stored as an index in a separate storage medium (e.g., the cache memory 1102), or both, and may be used to aid in verifying the data integrity of the stored data.

As an example of the above, where a set of input data is encoded into a sequence AATTCCGG, an example of creating a corresponding hash value may include assigning arbitrary values to each distinct nucleotide (e.g., A=1, T=2, C=3, G=4) and then mathematically combining the sequence of values into a single value (e.g., through one or more of addition, multiplication, or other mathematical operations). Additional values may also be combined into the hash, such as a value indicating the length of the sequence (e.g., in the above example, 8). Continuing the above example, a resultant hash value will depend upon the mathematical operations applied to produce the hash value.

As an example, a resultant hash value may be 28 (e.g., a result of addition of the sequence values and the sequence length), 4608 (e.g., a result of multiplication of the sequence values and the sequence length), or 132 (e.g., as a result of alternating addition and multiplication of the sequence values, followed by addition of the sequence length). Differing approaches will provide hash values having variable numbers of possible inputs, which may be used to verify the sequence of input nucleotides with varying levels of confidence. As an example, using a quaternary mapping of A=0, T=1, C=2, and G=3, sequences corresponding to the above examples of hash values may be TGO for 28, TACAAAA for 4608, and CATA for 132.

In implementations where a spacer value is included in a sequence, the spacer value may be paired with a hash value or other post-sequence or pre-sequence information, and may include an arbitrary sequence of nucleotides such as TTTTTTT, which may be unlikely to occur in normal encoding of input data, and which may be processed as a spacer value rather than encoded data when decoding sequenced data.

Figure 19:
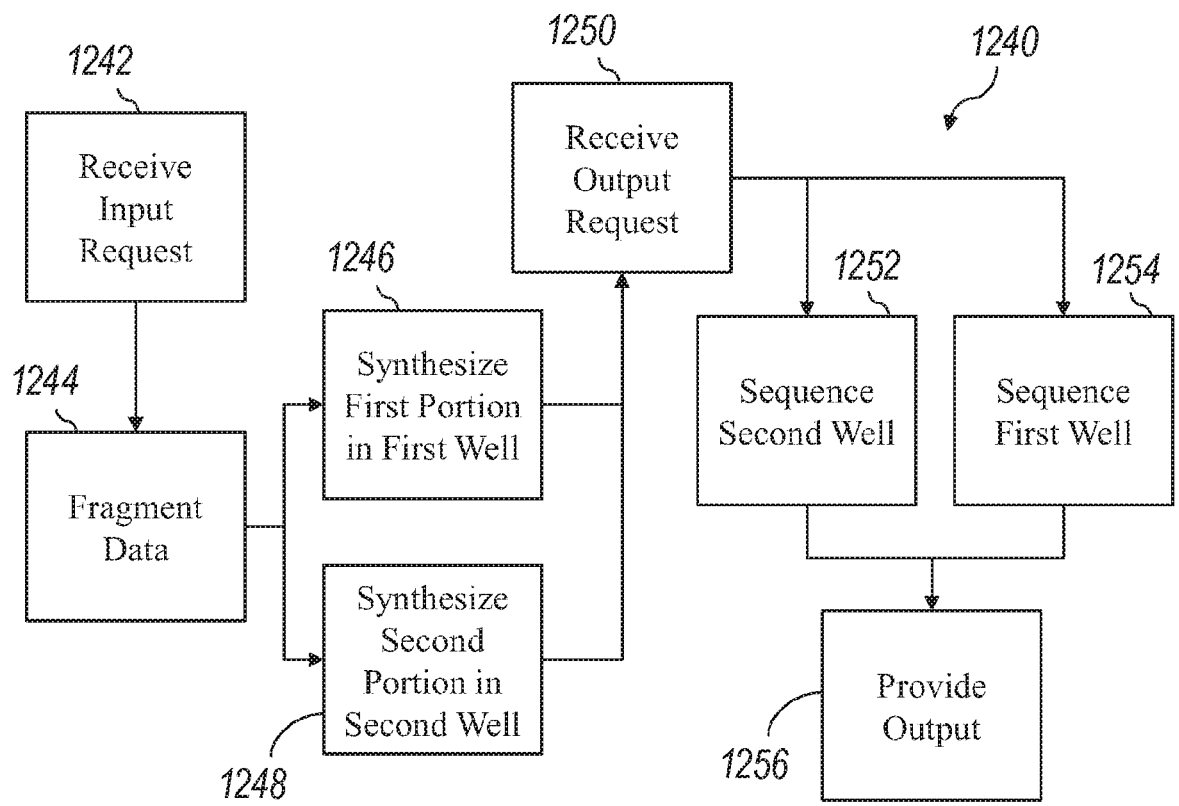
FIG. 19 depicts a flowchart of a process that may be performed to provide high speed data writing and reading with a storage device.

FIG. 19 depicts a flowchart of a process 1240 that may be performed to provide high speed data writing and reading with a storage device. The process of FIG. 19 may be performed using the storage device 1200, the storage devices 1210, or another storage device that supports per-well activation for synthesis and sequencing. When an input request is received (block 1242), the DNA storage system 1300 may fragment (block 1244) the data associated with the input request into multiple portions (e.g., two or more). Rather than writing the entire input into a single well, the system may synthesize and write the first portion into a first well (block 1246) and, in parallel, synthesize and write the second portion into a second well (block 1248). Where the first well and the second well may be separately synthesized in this manner without impacting the write speed of the other, the result is that the input data may be completely written to DNA storage about twice as fast, relative to writing the entire input to a single well. Similarly, when an output request is received (block 1250), the DNA storage system 1300 may sequence (block 1252) and read the second portion from the second well and, in parallel, sequence (block 1254) and read the first portion from the first well. The two portions may then be reassembled, and the complete output may be provided (block 1256). In this case also, the output data may be read from DNA storage at about twice the speed, relative to reading the data from a single well.

Figure 20:
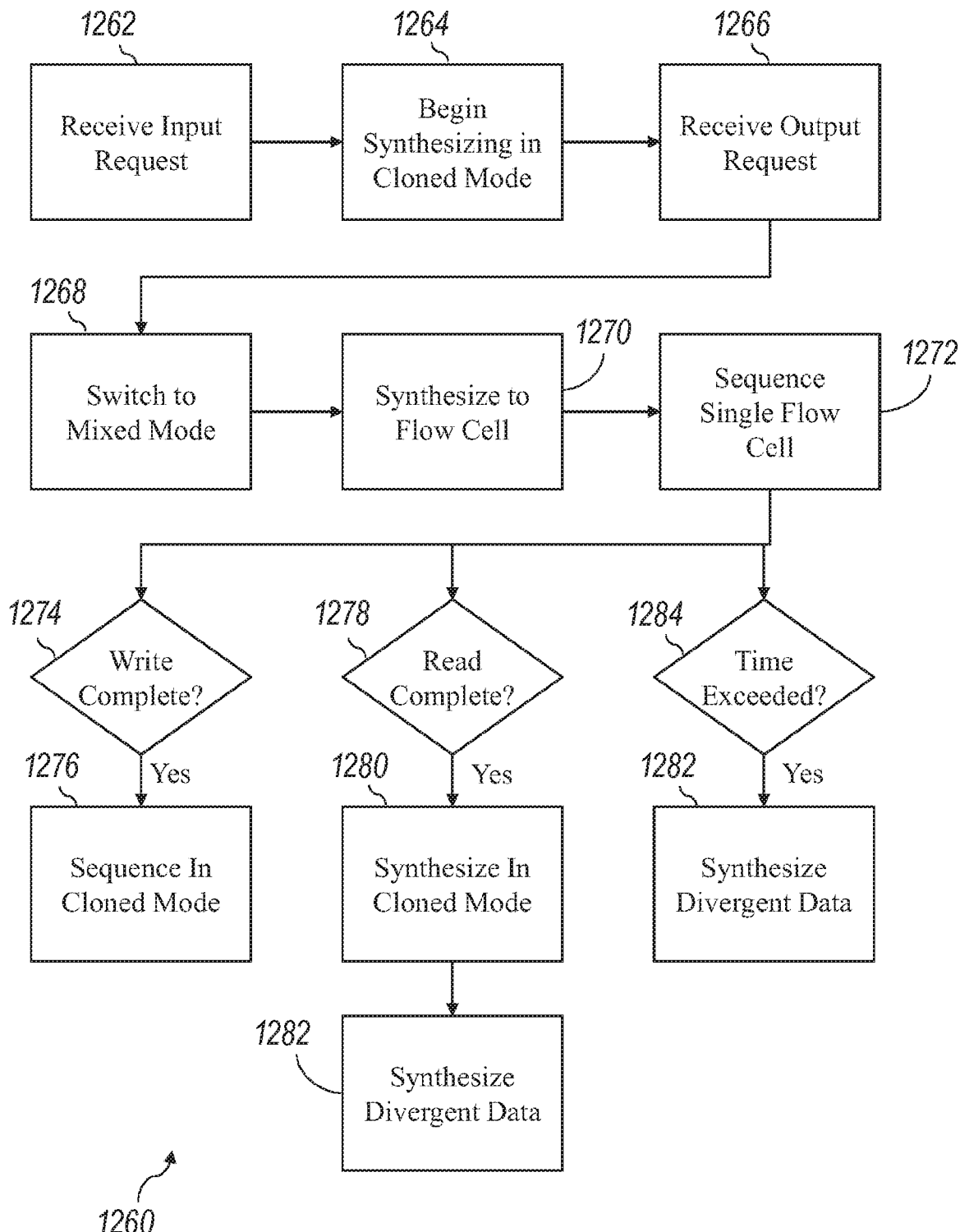
FIG. 20 depicts a flowchart of a process that may be performed to provide simultaneous reading and writing with a plurality of storage devices.

The multi-volume configurations disclosed herein may also be implemented to provide simultaneous reading and writing functionality, even in the absence of per-well activation features. As an example, FIG. 20 depicts a flowchart of a process 1260 that may be performed to provide simultaneous reading and writing where a plurality of separate volumes (e.g., flow cells) are available, such as the storage device 1200, and the storage devices 1210. When an input request is received (block 1262) by the DNA storage system 1300, the system will default to synthesizing (block 1264) and writing data to each volume in a cloned mode, such that separate wells on each separate volume (e.g., the first flow cell 1204 and the second flow cell 1206) contain identical polynucleotides after synthesis, absent any unexpected synthesis errors.

If a request for output to be read from the storage device 1200 is received (block 1266), the DNA storage system 1300 will switch (block 1268) to managing the plurality of volumes in a mixed mode, where synthesis (block 1270) continues uninterrupted on a first volume (e.g., the first flow cell 1204), but sequencing (block 1272) begins to read the requested output from the second volume (e.g., the second flow cell 1206). The DNA storage system 1300 may continue in mixed mode for a period of time, during which input may be continuously written to the first volume, while output may be continuously read from the second volume, so long as the requested data was present on the second volume prior to switching to mixed mode. Over time, the states of the first volume and the second volume will gradually diverge, as the first volume will increasingly contain data that is not cloned to the second volume.

To address this divergence, the DNA storage system 1300 may evaluate several factors to determine when to return to cloned mode. As an example, where all queued input requests are completed, and there are no pending operations for data to be synthesized and written (block 1274) to the first volume, the system may begin to sequence (block 1276) and read data from the plurality of volumes in cloned mode. In this manner, if an output request is received for data that is present within the divergent portion of data stored by the first volume, and that is not yet stored by the second volume, it may be read from the first volume without interruption. It should be noted that, with respective to the divergent data, a common file index or well index may be shared by the plurality of volumes and maintained to indicate availability of wells across the plurality of volumes. In other words, while it is not necessary that data written to a well that is positioned at coordinate X-Y on the first volume also be written to a well that is positioned at coordinate X-Y on the second volume, the aggregate data stored by each volume when they are full should be identical. In cases where it is desirable to enforce volume-to-volume correspondence of well positions, the shared filed and well indexes may be used to enforce such behavior.

As another example, where all queued output requests are completed, and there are no pending operations for data to be sequenced and read (block 1278) from the second volume, the system may return to synthesizing (block 1280) and writing data to the plurality of volumes in cloned mode, disregarding the divergent portion of data for the time being. At a later time, when there are minimal demands on the plurality of volumes, the DNA storage system 1300 may synthesize (block 1282) and write the divergent data onto the second volume, in order to return it to a true cloned stated of the first volume. In some implementations, synthesis (block 1282) of the divergent data may be performed based upon a read of the divergent data from the first volume, followed by a write to the second volume.

In some implementations, synthesis (block 1282) may be performed by performing in-situ cloning (e.g., clonal amplification) of the polynucleotides of the divergent data within the wells of the first volume that they are stored within, followed by transporting the cloned strands directly into corresponding wells of the second volume and binding them there, as has been described. In such an implementation, transport of the cloned strands between volumes may be enabled by a fluidics connection between each well in the first volume, and each corresponding well in the second volume, such that a flow of fluid may be used to transport the cloned strand directly from a well of the first volume, via the fluidic connection, to a corresponding well of the second volume.

As another example, the DNA storage system 1300 may be configured with a time threshold indicating an allowable period of time, or an allowable divergence of data. When the time or other threshold is exceeded (block 1284), as a result of extended periods of time in mixed mode or large volume of writing while in mixed mode, the DNA storage system 1300 may disable reading of data from the plurality of volumes for a period of time, and begin to synthesize (block 1282) and write the divergent data onto the second volume until caught up.

While the process of FIG. 20 has been described in the context of two volumes, it should be understood that three or more volumes may provide significant advantages in terms of maintaining redundancy of data, while also reducing the likelihood of excessive divergence of data for a particular volume. As an example, with three or more volumes being managed according to FIG. 20, a second and third volume may alternate between read and write modes in order to both reduce the amount of divergent data for any single drive, and to make more recently written data available to be read. As an example, if a third volume switches to read mode three hours after a second volume switched to read mode, in order to allow the second volume to switch back to write mode with the first volume, the immediate result may be that the second volumes divergent data may be capped at three hours' worth of written input, and that the third volume may have three additional hours of written input available to be read from the third volume, as compared to the available data on the second volume.

VIII. Data Error Risk Mitigation

In some implementations, a system configured to encode data in the form of, and read data from, nucleotide sequences such as machine-written DNA may include features to mitigate the risk of errors in the data that may result from phasing and/or pre-phasing during the writing and/or reading process. For example, in some implementations, when reading data previously written as a sequence of nucleotides, a system may compare the data read from the nucleotide sequence with a quality control value stored in non-nucleotide memory, and then use that comparison as a basis for determining if the nucleotide sequence (or the well storing the nucleotide sequence, in an implementation in which sequences are stored in a well as addressable elements) should be treated as having corrupted data. In implementations where this type of comparison takes place, it may be performed in a variety of manners. For example, in some implementations, comparison of a nucleotide sequence may be performed by calculating a value based on the nucleotide sequence as read (e.g., a checksum, a hash value, or some other type of error detection value) and then comparing that value with a value that had previously been calculated and stored in the non-nucleotide memory at the time the data that should have been encoded in the nucleotide sequence was written. Similarly, in some implementations, when a nucleotide sequence is written to a DNA storage device, the data that should be encoded in that sequence may be stored in non-nucleotide memory, and the comparison may be a direct comparison of data read from the nucleotide sequence with the data stored in the non-nucleotide memory. Combined approaches may also be used in some implementations.

Figure 22:
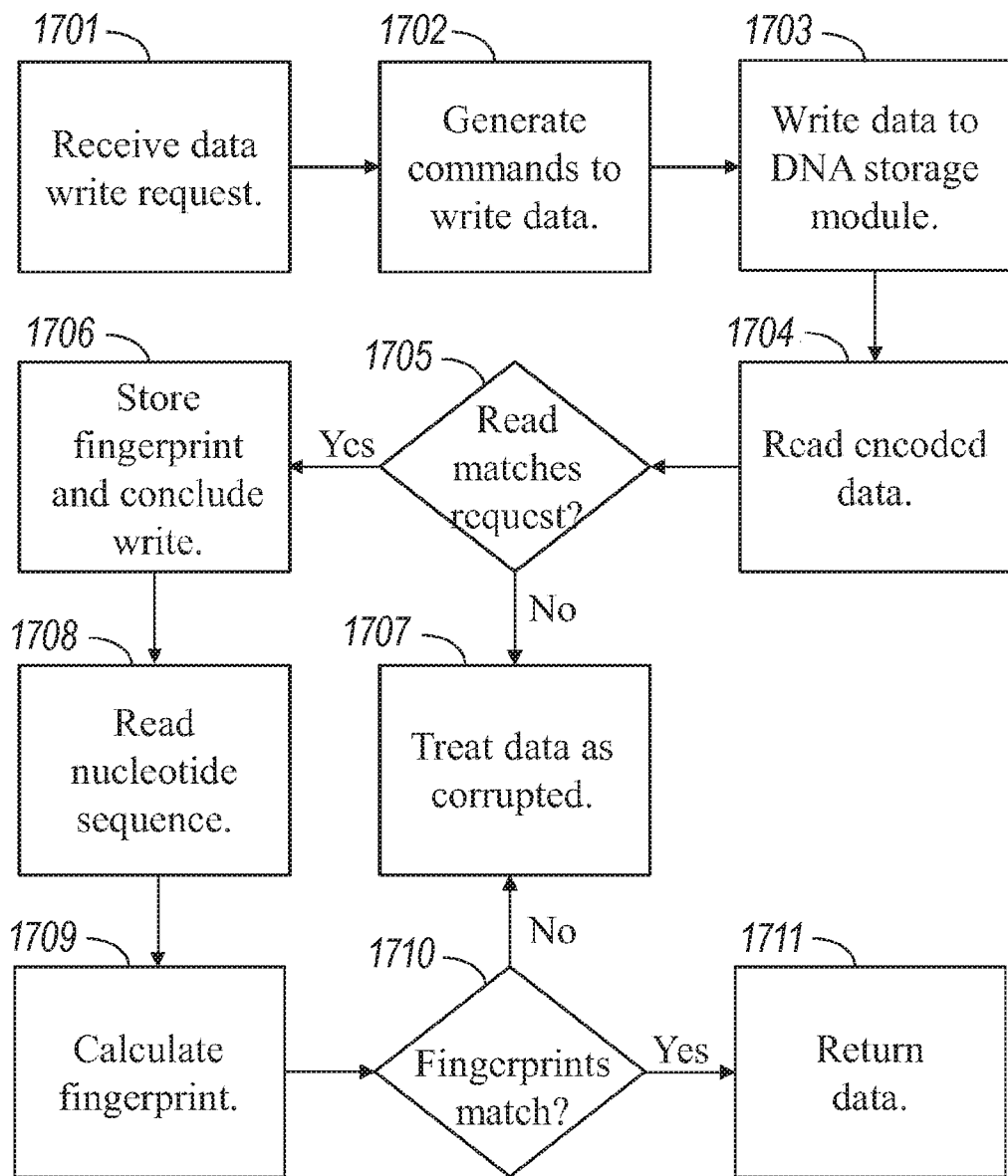
FIG. 22 is a depiction of processes of reading and writing data that may be performed in some implementations.

In some implementations, combinations of risk mitigation approaches such as described in the preceding paragraph may also be used. To illustrate, consider FIG. 22, which depicts processes of reading and writing data that may be performed in some implementations. Initially, a method such as shown in FIG. 22 may include receiving a data write request, as shown in block 1701 of FIG. 22. This may be, for example, a request submitted by a user via a user interface 130 to store a file in a DNA storage device, or an automatically generated request to store data generated as the output of a process, as an internal backup, or for other purposes. After receiving a data write request (block 1701), the method may include generating one or more commands to write the data, as shown in block 1702 of FIG. 22. This may include, for example, determining how the data to be written should be represented given the nature of the DNA storage device (e.g., the length of nucleotide sequences that may feasibly be written, the encoding scheme used for the data, etc.), determining the specific location(s) in the DNA storage device where the nucleotide sequences encoding the data should be synthesized, and generating the commands for synthesizing those sequences (e.g., commands for activating electrodes corresponding to specific wells 630 in a flow cell 600, 601 causing bases to be added to the strands in those wells 630 as appropriate). These commands may then be executed to write the data to the DNA storage device, as shown in block 1703 of FIG. 22.

In some implementations, after data is written (block 1703) to a DNA storage device, it may be automatically read (i.e., the polynucleotide(s) in which the data is written may be sequenced, either directly or by copying the polynucleotide(s) and sequencing the copy/copies), as shown in block 1704 of FIG. 22. The read data may then be compared with the data that was the subject of the original write request, as shown in block 1705 of FIG. 22. For example, in some implementations, when a write request is received (block 1701), the data to be written will automatically be maintained in the system's non-nucleotide memory (e.g., in RAM of the system controller 120) until a confirmation of successful write is received. In these types of implementations, the comparison (block 1705) of the data read from the DNA storage device with the data that was the subject of the original request may be performed by doing a bit level comparison of the data from the write request that was stored in the system's non-nucleotide memory with the data read by sequencing the information written to the DNA storage device.

In an implementation performing a process such as shown in FIG. 22, if data read (block 1704) from the DNA storage device matches the data in the system's non-nucleotide memory, then a fingerprint of the data may be stored and the write operation may be concluded, as shown in block 1706 of FIG. 22. In some implementations, storing a fingerprint of the data may include calculating a checksum, a cyclic redundancy check value, a hash value, or other similar types of values that may be used to detect changes in encoded data, then storing that value in non-volatile memory such as a magnetic disk drive, solid state memory, optical disc, or other type of memory element. In some implementations, a fingerprint may also information about how data was encoded rather than the data itself. For example, if a nucleotide sequence was made of the bases A, C, T and G, then a fingerprint may be made up of the number of instances of A, the number of instances of C, the number of instances of T and the number of instances of G in the sequence, rather than reflecting the data encoded using those bases. Other variations (e.g., a fingerprint showing parity of the number of each type of base included in the sequence, a fingerprint based on both data and how the data is encoded) are also possible; and may be used in various implementations. In some implementations, the fingerprint may be appended to the end of the DNA sequence. Concluding the write operation may include sending a message to the source of the write request indicating that the data had been successfully written. Additionally, in some implementations, concluding the write operation may involve purging the data that was included in the write request from one or more locations in memory so that those locations may be used for storing other information (e.g., new data that may be included in future write requests).

In some implementations, if data read (block 1704) from the DNA storage device does not match the data in the system's non-nucleotide memory, the data may be treated as having been corrupted (e.g., not properly written), as shown in block 1707 of FIG. 22. In some implementations this treatment of the data as corrupted may trigger various error handling processes. For example, in some implementations if data read (block 1704) from the DNA storage device does not match the data in the system's non-nucleotide memory, then a process such as shown in FIG. 22 may return to writing (block 1703) the data to the DNA storage device, so that the data may be recorded despite whatever issues had caused the earlier error. As another approach, in some implementations, if data read (block 1704) from the DNA storage device does not match data in the system's non-nucleotide memory, then the location with the non-matching data may be identified as "bad" (e.g., a corrupted data flag in an index may be flipped for that location) and the correct data may subsequently (e.g., during a future low-utilization period) be written to the corrupted data's location. As another approach, in some implementations, if data read (block 1704) from the DNA storage device does not match data in the system's non-nucleotide memory, an error message (e.g., a function return code) may be generated indicating that the write had encountered a problem that may require remediation by some other aspect of the system or the user (e.g., an error code may be generated identifying the location of the "corrupted" data as a location where hardware troubleshooting, such as replacement of electrodes 640, may be appropriate). Combined approaches may also be used in some implementations. For example, in some implementations if data read (block 1704) from the DNA storage device does not match data in the system's non-nucleotide memory, the writing (block 1703) of data to the DNA storage device may be retried and an error message may be generated so that the user may be made aware of an incipient problem that he or she may want to address before it develops into an unrecoverable failure. Other approaches will be immediately apparent to, and may be implemented without undue experimentation by, those of ordinary skill in the art as well, and may be utilized in other implementations. Accordingly, the description of how an implementation performing a method such as shown in FIG. 22 may treat data as corrupted (block 1707), and how such an implementation may potentially respond to such corruption, should be understood as being illustrative only, and should not be treated as limiting.

In some implementations, a system 100 may read a nucleotide sequence, such as by sequencing it as described previously, as shown in block 1708 of FIG. 22. This may be done, for example, in response to a read request (e.g., a request to retrieve a previously stored file), as part of a data quality check (e.g., in some implementations, data stored in a DNA storage device may be periodically read to identify if it had degraded while in storage), or for other suitable reasons. In some implementations, after a nucleotide sequence is read (block 1708), it may be subjected to additional risk mitigation steps, such as calculating a fingerprint based on the data that was read, as shown in block 1709 of FIG. 22. This fingerprint may then be compared to another fingerprint it may be expected to correspond to (e.g., a fingerprint created and stored (block 1706) automatically as part of the write process) to determine if the retrieved data should be treated as corrupted and/or if an error in the reading process occurred, as shown in block 1710 of FIG. 22. In some implementations, if there was a match, then the retrieved data may be returned (e.g., sent as a return value to a process that had issued a read request), as shown in block 1711 of FIG. 22. Alternatively, in some implementations, the read data may not be returned, and instead some kind of code may be provided (e.g., a code indicating that no error had been found, if the data was read (block 1708) as part of a data quality check). Similarly, if the comparison (block 1710) found that the fingerprints did not match, then the data may be treated as corrupted (block 1707) and, in some implementations, various error handling processes such as described previously may be initiated.

In some implementations, other types of risk mitigation measures may be taken, and/or there may be variations on how risk mitigation measures such as those described above may be put into practice. For example, in some implementations, when data is written to a location (e.g., a well in a flow cell), a mirrored copy may also be automatically be written to a second location (e.g., a second well in the same flow cell, or a well in a different flow cell). In some such implementations, the existence of one or more mirrored copies may be used to improve system performance such as by supporting parallel operations. For example, in some implementations, a DNA storage device may comprise two flow cells (e.g., two flow cells 601), a first of which is used for read operations, and a second of which is used for write operations. In such a scenario, if two different users wanted to concurrently read from, and write to, data stored in a particular location, the user making the read request may be fulfilled by sequencing the copy of the data stored in the first flow cell 601; while at the same time the write request was fulfilled by writing a new polynucleotide into the appropriate location in the second flow cell 601. Subsequently, when the requests had been processed (e.g., during a low activity period) the first flow cell 601 may be resynchronized with the second flow cell 601, thereby ensuring that whatever data had been written to the second flow cell 601 may be read using the first flow cell 601 whenever the next read request was issued.

As another example, in some implementations, when data is to be written, in addition to writing that data, a system may be implemented to write both that data as well as a redundancy value that may be used to recreate a portion of the data in the event it was lost. To illustrate, consider Table 2 below, which provides an example of such a redundancy value as may be generated for data stored in the form of four polynucleotide, each of which stores four bits of data.

TABLE 2

Example of approach to storing data with a redundancy sequence that allows a portion of the data to be recreated in the event it is lost.

| Data Sequence 1 | Data Sequence 2 | Data Sequence 3 | Data Sequence 4 | Redundancy Sequence |
|---|---|---|---|---|
| 1 | 1 | 1 | 1 | XOR 0 |
| 1 | 1 | 1 | 0 | XOR 1 |
| 1 | 1 | 0 | 0 | XOR 0 |
| 1 | 0 | 0 | 0 | XOR 1 |

In some implementations, 16 bits of data may be broken up into four four-bit sequences, and a fifth four-bit sequence may be created by applying the logical XOR operator to the bits from the first four sequences. These five sequences may then be stored in five polynucleotides in five different locations in a DNA storage device. Then, in the event the data in one of the locations was found to be corrupted, that data may be recreated by applying the XOR operator to the remaining four sequences and encoding/storing the result as a new polynucleotide in the location that previously held the corrupted data.

Additionally, in some implementations, when a polynucleotide is encoded to store data in a DNA storage device, in addition to storing the data, the polynucleotide may be synthesized to include error detection data such as fingerprints of the type described previously. For example, in some implementations, when a polynucleotide is synthesized, a parity bit may be calculated based on the data the polynucleotide is synthesized to encode, and a methylated (or non-methylated) base may be added to the polynucleotide to represent that parity bit. Similarly, in some implementations, other types of information preserving modifications (i.e., modifications that do not interfere with a base being read, but which also allow a modified base to be distinguished from a non-modified base), such as additions of synthetic bases or of sequences encoding parity or other error checking information, may also or alternatively be used. In some implementations in which this type of error correcting data is included in polynucleotides, this type of data may potentially be used to identify and remediate errors. For example, in some implementations, when each polynucleotide is stored a mirrored copy may be stored in another location. Then, when a polynucleotide is read, both the polynucleotide and its mirrored copy may be read and compared with each other. If this comparison indicates that the polynucleotide and its mirrored copy were not identical, then the checksums may be recalculated and whichever strand had a recalculated checksum that matched its methylation may be treated as correct and the other strand may be treated as corrupted and replaced (e.g., as part of an error handling routine such as those described previously).

As another example, in some implementations, to identify if data should be treated as corrupted, the sequence to be tested may be examined to determine if it may bind to one of a plurality of error checking polynucleotides. For example, in an example where a nucleotide sequence concludes with a fingerprint portion, when the sequence is read a new fingerprint may be calculated based on the data read from the sequence. An error checking strand may then be synthesized that encoded the fingerprint in reverse order and, if the fingerprint on the end of the original nucleotide sequence did not bind to the newly synthesized fingerprint strand, this may be treated as indicating that the data had been corrupted and should be replaced.

When sequencing on a CMOS sequencing chip, it may be useful to employ various image correction techniques such as image optical or spectral cross talk between different pixels and the correction process may vary from one chip to another. Correction methods may employ spatially controlled on-flow cell training data with diversity for base calling training of data, particularly for optical systems, where optical cross talk introduces error that requires internal calibration. For example, smaller pitch flow cells may have distortion near each well, which may be masked using known sequence. The correction methods may include an on-board QC system based on writing a predetermined sequence for different DNA reading systems. The predetermined sequence may be contained or adjacent to a well and may provide correction factors for base calling. The methods provide individual well cross talk correction (creating known-truth or a truth table). Known sequences may be placed at predetermined spaces on a flow cell for synchronizing the sequencer and/or for possible random access. The methods may allow for in-field calibration.

IX. Miscellaneous

All of the references, including patents, patent applications, and articles, are explicitly incorporated by reference herein in their entirety.

The foregoing description is provided to enable a person skilled in the art to practice the various configurations described herein. While the subject technology has been particularly described with reference to the various figures and configurations, it should be understood that these are for illustration purposes only and should not be taken as limiting the scope of the subject technology.

As used herein, an element or step recited in the singular and proceeded with the word "a" or "an" should be understood as not excluding plural of said elements or steps, unless such exclusion is explicitly stated. Furthermore, references to "one implementation" are not intended to be interpreted as excluding the existence of additional implementations that also incorporate the recited features. Moreover, unless explicitly stated to the contrary, implementations "comprising" or "having" an element or a plurality of elements having a particular property may include additional elements whether or not they have that property.

The terms "substantially" and "about" used throughout this Specification are used to describe and account for small fluctuations, such as due to variations in processing. For example, they may refer to less than or equal to ±5%, such as less than or equal to ±2%, such as less than or equal to +1%, such as less than or equal to ±0.5%, such as less than or equal to ±0.2%, such as less than or equal to ±0.1%, such as less than or equal to 0.05%.

There may be many other ways to implement the subject technology. Various functions and elements described herein may be partitioned differently from those shown without departing from the scope of the subject technology. Various modifications to these implementations may be readily apparent to those skilled in the art, and generic principles defined herein may be applied to other implementations. Thus, many changes and modifications may be made to the subject technology, by one having ordinary skill in the art, without departing from the scope of the subject technology. For instance, different numbers of a given module or unit may be employed, a different type or types of a given module or unit may be employed, a given module or unit may be added, or a given module or unit may be omitted.

Underlined and/or italicized headings and subheadings are used for convenience only, do not limit the subject technology, and are not referred to in connection with the interpretation of the description of the subject technology. All structural and functional equivalents to the elements of the various implementations described throughout this disclosure that are known or later come to be known to those of ordinary skill in the art are expressly incorporated herein by reference and intended to be encompassed by the subject technology. Moreover, nothing disclosed herein is intended to be dedicated to the public regardless of whether such disclosure is explicitly recited in the above description.

It should be appreciated that all combinations of the foregoing concepts and additional concepts discussed in greater detail below (provided such concepts are not mutually inconsistent) are contemplated as being part of the inventive subject matter disclosed herein. In particular, all combinations of claimed subject matter appearing at the end of this disclosure are contemplated as being part of the inventive subject matter disclosed herein.

What is claimed is:

1. A system for non-volatile storage comprising:
    a storage controller comprising a processor and a memory;
    a storage device comprising:
        a flow cell comprising a plurality of wells with open sides accessible from a first surface of the flow cell, wherein the wells are adapted to contain polynucleotides, each well comprising a plurality of electrodes, each electrode of the plurality of electrodes being associated with a corresponding nucleotide,
        a fluidics interface, the fluidics interface being configured to provide a path for communication of fluid from a fluidics device to the flow cell, and
        a sequencing interface, the sequencing interface being configured to provide a path for communication of light between a sequencing device and the flow cell;
    a fluidics device to provide one or more fluids to the first surface of the flow cell, wherein the one or more fluids comprise a nucleotide writing reagent and a nucleotide reading reagent, the nucleotide writing reagent being configured to write nucleotides to the wells of the flow cell during a synthesis process, the nucleotide reading reagent being configured to provide reading of nucleotides in the wells of the flow cell during a sequencing process;
    a sequencing device to sequence polynucleotides within the plurality of wells via the sequencing interface and determine nucleotides; and
    the memory of the storage controller comprising a cache memory, the cache memory comprising a non-nucleotide memory to store data that is queued to be encoded into a set of nucleotides and synthesized, using the nucleotide writing reagent, into polynucleotides in the plurality of wells;
    the storage controller being programmed to:
        cause the non-nucleotide memory to store the data that is queued to be encoded into the set of nucleotides, identify a sequence of nucleotides representing the data that is queued to be encoded into the set of nucleotides, cause the fluidics device to communicate the nucleotide writing reagent to the storage device, and cause activation of the plurality of electrodes, to thereby encode data in the plurality of wells by synthesizing the set of nucleotides in the plurality of wells in response to a combination of the communicated nucleotide writing reagent and the activated electrodes, the synthesized set of nucleotides having the identified sequence of nucleotides representing the data, the synthesized set of nucleotides forming at least part of the polynucleotides in the plurality of wells.

2. The system of claim 1, wherein the cache memory stores one or more of:

a set of file indexes describing the name and location of data stored as polynucleotides within the plurality of wells, and a set of checksum values usable to verify the integrity of data stored as polynucleotides within the plurality of wells.

3. The system of claim 1, wherein the storage controller:

receives a set of input data to be written to the storage device, via a nucleotide writing reagent provided to the flow cell by the fluidics device, as polynucleotides in the plurality of wells, receives a request for output data to be read by the sequencing device from polynucleotides stored in the plurality of wells, determines whether the storage device is in a write-mode or a read-mode based upon whether it has most recently received the nucleotide writing reagent or the nucleotide reading reagent from the fluidics device, where the storage device is in the write-mode, writes the set of input data prior to reading the output data, and where the storage device is in the read-mode, stores the set of input data on the cache memory and reads the output data prior to writing the set of input data.

4. The system of claim 1, wherein the storage controller:

operates the sequencing device to sequence a subset of the plurality of wells and produce a set of nucleotides describing the polynucleotides stored in the subset of the plurality of wells, converts the set of nucleotides into a set of digital data, stores the set of digital data in the cache memory, and provides the set of digital data from the cache memory in response to subsequent requests.

5. The system of claim 1, cause the non-nucleotide memory to store a file index, the file index indicating contents of the encoded data in the plurality of wells and locations of the encoded data in the plurality of wells.

6. The system of claim 1, the memory storing instructions for the processor to perform a method comprising:

generating one or more commands to write specified data to a polynucleotide associated with a particular location in the storage device, reading the polynucleotide, performing a comparison, wherein the comparison compares the polynucleotide stored in the storage device with a particular quality control value stored in a non-nucleotide memory, and based on the comparison, determining if the particular location in the storage device is to be treated as having corrupted data.

7. The system of claim 6, the method further comprising:

reading the polynucleotide, performing the comparison, and determining if the particular location in the storage device is to be treated as having corrupted data automatically based on receiving a command to write to the storage device.

8. The system of claim 6, the method further comprising:

determining that the particular location in the storage device is to be treated as having corrupted data, and based on determining that the particular location in the storage device is to be treated as having corrupted data, writing a new polynucleotide encoding uncorrupted data to the particular location in the storage device.

9. The system of claim 6, the polynucleotide comprising a check portion, the check portion representing a parity bit to provide error detection in the data represented by the sequence of nucleotides in the set of nucleotides synthesized in the plurality of wells; and the method further comprising generating the check portion, in the set of nucleotides synthesized in the plurality of wells, based on the specified data.

10. The system of claim 6, the particular quality control value being the specified data; and the comparison comprising checking if there are any differences between data stored in the polynucleotide and the specified data.

11. The system of claim 6, the method further comprising:

determining that the particular location in the storage device should not be treated as having corrupted data, and based on determining that the particular location in the storage device should not be treated as having corrupted data, deleting the particular quality control value stored in the non-nucleotide memory.

12. A system for non-volatile storage comprising:

a nucleotide memory storage device comprising:

a flow cell comprising a plurality of wells with open sides accessible from a first surface of the flow cell, wherein the wells are adapted to contain polynucleotides, a fluidics interface, the fluidics interface being configured to provide a path for communication of fluid from a fluidics device to the flow cell, and a sequencing interface, the sequencing interface being configured to provide a path for communication of light between a sequencing device and the flow cell;

a fluidics device to provide one or more fluids to the first surface of the flow cell, the one or more fluids including:

a nucleotide writing reagent to write nucleotides to the wells of the flow cell during a synthesis process, and a nucleotide reading reagent to provide reading of nucleotides in the wells of the flow cell during a sequencing process;

a sequencing device to sequence polynucleotides within the plurality of wells via the sequencing interface and determine nucleotides during the sequencing process;

a light source; and a non-nucleotide cache memory to store data that is queued to be encoded into a set of nucleotides and synthesized, using the nucleotide writing reagent, into polynucleotides in the plurality of wells;

a controller programmed to:

cause the non-nucleotide memory to store the data that is queued to be encoded into the set of nucleotides, cause the fluidics device to communicate the nucleotide writing reagent to the nucleotide memory storage device, and cause activation of the light source to activate selected nucleotides, to thereby synthesize polynucleotides in the plurality of wells via light, the synthesized polynucleotides including the set of nucleotides, the set of nucleotides synthesized in the plurality of wells via light having a sequence of nucleotides representing the encoded data.

\* \* \* \* \*

UNITED STATES PATENT AND TRADEMARK OFFICE
CERTIFICATE OF CORRECTION

PATENT NO. : 12,201,985 B2  
APPLICATION NO. : 18/103625  
DATED : January 21, 2025  
INVENTOR(S) : Merek Siu et al.

Page 1 of 1

It is certified that error appears in the above-identified patent and that said Letters Patent is hereby corrected as shown below:

In the Claims

In Column 67, Line 51 (approx.), Claim 5, below "The system of claim 1," insert -- the storage controller being further programmed to: --, therefor.

Signed and Sealed this  
First Day of April, 2025

Coke Morgan Stewart  
*Acting Director of the United States Patent and Trademark Office*